(12) United States Patent
Diaz-Fernández et al.

(10) Patent No.: US 9,193,738 B2
(45) Date of Patent: Nov. 24, 2015

(54) SUBSTITUTED PYRANO AND FURANOQUINOLINES, THEIR PREPARATION AND USE AS MEDICAMENTS

(71) Applicant: LABORATORIOS DEL DR. ESTEVE S.A., Barcelona (ES)

(72) Inventors: José-Luis Diaz-Fernández, Barcelona (ES); Ute Christmann, Tarragona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/374,081

(22) PCT Filed: Jan. 24, 2013

(86) PCT No.: PCT/EP2013/051328
§ 371 (c)(1),
(2) Date: Jul. 23, 2014

(87) PCT Pub. No.: WO2013/110698
PCT Pub. Date: Aug. 1, 2013

(65) Prior Publication Data
US 2015/0031692 A1    Jan. 29, 2015

(30) Foreign Application Priority Data
Jan. 24, 2012    (EP) .................................... 12382020

(51) Int. Cl.
| | | |
|---|---|---|
| *C07D 455/04* | (2006.01) | |
| *C07D 491/00* | (2006.01) | |
| *C07D 491/052* | (2006.01) | |
| *C07D 491/04* | (2006.01) | |
| *C07D 491/048* | (2006.01) | |

(52) U.S. Cl.
CPC .......... *C07D 491/052* (2013.01); *C07D 491/04* (2013.01); *C07D 491/048* (2013.01)

(58) Field of Classification Search
CPC ................................................. C07D 491/044
USPC .................................................... 546/80, 89
See application file for complete search history.

(56) References Cited

U.S. PATENT DOCUMENTS 3,631,050 A * 12/1971 Elslager et al. .................. 546/89
2007/0203167 A1    8/2007 Schiemann

FOREIGN PATENT DOCUMENTS

| EP | 1634873 | 3/2006 |
|---|---|---|
| EP | 1847542 | 10/2007 |
| WO | WO 2005/063736 | 7/2005 |
| WO | WO 2007/098961 | 9/2007 |
| WO | WO 2009/071657 | 6/2009 |

OTHER PUBLICATIONS

Rai et al. Synthetic Communications (2009), 39(12), 2125-2136.*
Venkatesh et al., J. Pharm. Sci. 89, 145-54 (2000).*
Wolff, Burgers medicinal Chemistry and Drug Discovery, vol. 1, Principles and Practice, John Wiley & sons, New York, 1997.*
West (Solid-State Chemistry and Its Applications, 1984, John Wiley & Sons).*
Alcaide, et al., Chem. Eur. J., 2003, 9, 3415-3426.
Bowen, Pharmaceutica Acta Helvetiae, 2000, 74, 211-218.
DeHaven-Hudkins, et al., Eur. J. Pharmacol., 1992, 227, 371-378.
Extended European Search Report for EP 12362020.1 dated Mar. 30, 2012.
Hanner, et al., Proc. Natl. Acad. Sci., 1996, 93, 8072-8077.
Kaiser, et al., Neurotransmissions, 1991, 7, 1-5
Kamble, et al., Synlett, 2007, 1379-1382.
Katritzky, et al., Journal of Organic Chemistry, 1997, 62, 8210-8214.
Merskey, et al., IASP, Classification of Chronic Pain, 2nd Edition, IASP Press (2002), 210.
More, et al., Synlett, 2006, 9, 1399-1403.
Quirion, et al., Trends Pharmacol. Sci., 1992, 13, 85-86.
Rai, et al., Synthetic Communications, 2009, 39, 2125-2136.
Ramesh, et al., Synthetic Communications, 2006, 36, 1431-1436.
Ronsisvalle, et al., Pure Appl. Chem., 2001, 73, 1499-1509.
Schläger, et al., Bioorganic & Medicinal Chemistry, 2008, 16, 2992-3001.
Snyder, et al., J. Neuropsychiatry 1989, 1, 7-15.
Walker, et al., Pharmacological Reviews, 1990, 42, 355-402.
Xia, et al., Synlett, 2005, 15, 2357-2361.
Zhang, et al., Nuclear Medicine and Biology, 2002, 29, 469-476.
Zhou, et al., European Journal of Organic Chemistry, 2007, 31, 5265-5269.
Zubkov, et al., Russian Journal of Organic Chemistry, 2007, 43, 1202-1208.

* cited by examiner

*Primary Examiner* — Nizal Chandrakumar
(74) *Attorney, Agent, or Firm* — Hueschen and Sage

(57) ABSTRACT

The present invention relates to new substituted pyrano and furanoquinolines having a great affinity for sigma receptors, especially sigma-1 receptors, as well as to the process for the preparation thereof, to compositions comprising them, and to their use as medicaments.

10 Claims, No Drawings

SUBSTITUTED PYRANO AND FURANOQUINOLINES, THEIR PREPARATION AND USE AS MEDICAMENTS

FIELD OF THE INVENTION

The present invention relates to new substituted pyrano and furanoquinolines having a great affinity for sigma receptors, especially sigma-1 receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

"The sigma receptor's" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic.

Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Different sigma receptor ligands have been reported.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009071657 also reports tricyclic triazolic compounds having good activity towards sigma receptors.

Although, some pyrano and furanoquinolines have been disclosed in the prior art, for instance, by Schiemann K. et al [WO200506735; Bioorganic & Medicinal Chemistry letters (2010), 20(5):1491-1495], Zhou Z. et al. [European Journal of Organic Chemistry (2007), (31):5265-5269], More S. V. et al [Synlett (2006), (9):1399-1403] or Katritzky A. R. et al [Journal of Organic Chemistry (1997), 62(23):8210-8214]

none of these references discloses the pyrano and furanoquinolines of the present invention. In addition none of these references suggest that pyrano and furanoquinolines can be active towards sigma receptors.

Nevertheless, there is still a need to find compounds having pharmacological activity towards the sigma receptor, being both effective and selective, and having good "drugability" properties, i.e. good pharmaceutical properties related to administration, distribution, metabolism and excretion.

SUMMARY OF THE INVENTION

The present invention discloses novel compounds with great affinity to sigma receptors which might be used for the treatment of sigma related disorders or diseases.

Specifically, it is an object of the present invention novel pyrano and furanoquinolines of general formula (I):

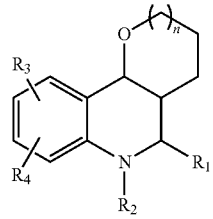

(I)

Another object of the invention is the different processes for preparation of compounds of general formula (I).

Another object of the invention refers to the use of such compounds of general formula (I) for the treatment or prophylaxis of sigma receptor mediated diseases or conditions, especially sigma-1 mediated diseases or conditions. Within the group of diseases or conditions mediated by sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are very good and are especially effective for the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to a compound of general formula (I):

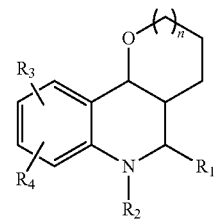

(I)

where
$R_1$ is a saturated or unsaturated $C_{3-9}$ cycloalkyl optionally at least monosubstituted, optionally at least containing one heteroatom as a ring member selected from N, O or S, which may be condensed with an optionally at least monosubstituted mono or polycyclic ring system;

$R_2$ is selected from the group consisting of hydrogen; a branched or unbranched, saturated or unsaturated, optionally at least mono-substituted, aliphatic radical $C_{1-10}$ or —$CH_2R_5$;

$R_3$ and $R_4$ are independently selected from the group consisting of hydrogen; —$NO_2$; —$CF_3$; —OH; —SH; —$NR_5R_6$; —CN; a branched or unbranched, saturated or unsaturated, optionally at least mono-substituted, aliphatic radical $C_{1-10}$; a saturated or unsaturated $C_{3-9}$ cycloalkyl optionally at least monosubstituted, optionally at least containing one heteroatom as a ring member selected from N, O or S which may be condensed with an optionally at least monosubstituted mono or polycyclic ring system; a substituted or unsubstituted aryl; —NHC(O)NHR$_7$; —NHC(S)NHR$_7$; —C(O)OR$_8$; —OR$_9$; —NR$_{10}$C(O)R$_{11}$; —SR$_{12}$; —C(O)NR$_{13}$R$_{14}$; —SO$_2$NR$_{15}$R$_{16}$ or halogen $R_5$ to $R_{12}$ are independently selected from hydrogen; a branched or unbranched, saturated or unsaturated, optionally at least mono-substituted, aliphatic radical $C_{1-10}$; substituted or unsubstituted aryl; substituted or unsubstituted $C_{3-9}$ cycloalkyl optionally at least containing one heteroatom as a ring member selected from N, O or S which may be condensed with an optionally at least monosubstituted mono or polycyclic ring system; or substituted or unsubstituted heteroaryl which may be condensed with an optionally at least monosubstituted mono or polycyclic ring system;

$R_{13}$ to $R_{16}$ are independently selected from hydrogen; a branched or unbranched, saturated or unsaturated, optionally at least mono-substituted, aliphatic radical $C_{1-10}$; substituted or unsubstituted aryl; substituted or unsubstituted $C_{3-9}$ cycloalkyl optionally at least containing one heteroatom as a ring member selected from N, O or S which may be condensed with an optionally at least monosubstituted mono or polycyclic ring system; substituted or unsubstituted heteroaryl which may be condensed with an optionally at least monosubstituted mono or polycyclic ring system;

or $R_{13}$ to $R_{16}$ together with the bridging nitrogen form a $C_{3-9}$ cycloalkyl optionally containing at least one additional heteroatom as a ring member selected from N, O or S; n is 0 or 1;

with the proviso that at least one of $R_3$ or $R_4$ is always different from hydrogen and with the proviso that when $R_1$ is cyclohexyl, unsubstituted tetrahydrofurane or substituted pyrrolidine, if $R_3$ or $R_4$ are in position 8 when n=0 or in position 9 when n=1, they are not tert-butyl, or a pharmaceutically acceptable salt, isomer, prodrug or solvate thereof.

"Halogen" or "halo" as referred in the present invention represent fluorine, chlorine, bromine or iodine.

Aliphatic radicals $C_{1-10}$, as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include but are not restricted to methyl, ethyl, vinyl(ethenyl), ethinyl, propyl, n-propyl, isopropyl, allyl(2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, isopentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-6}$ alkyl group, cycloalkyl $C_{3-9}$ group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R" whereby R' and optionally R" for each substituent independently represents a linear or branched $C_{1-6}$-alkyl group.

Alkyl radicals, as referred to in the present invention, are saturated aliphatic radicals. They may be linear or branched and are optionally substituted. $C_{1-6}$ alkyl as expressed in the present invention means an alkyl radical of 1, 2, 3, 4, 5 or 6 carbon atoms.

Cycloalkyl radical $C_{3-9}$, as referred to in the present invention, are understood as meaning saturated and unsaturated (but not aromatic), cyclic hydrocarbons, which can optionally be unsubstituted, mono- or polysubstituted. In these radicals, for example C3-4-cycloalkyl represents C3- or C4-cycloalkyl, C3-5-cycloalkyl represents C3-, C4- or C5-cycloalkyl, etc. With respect to cycloalkyl, the term also includes saturated cycloalkyls in which optionally at least one carbon atom may be replaced by a heteroatom, preferably S, N or O. However, mono- or polyunsaturated, preferably monounsaturated, cycloalkyls without a heteroatom in the ring also in particular fall under the term cycloalkyl as long as the cycloalkyl is not an aromatic system. Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, noradamantyl, pyrroline, pyrrolidine, pyrrolidineone, pyrazoline, pyrazolinone, oxopyrazolinone, aziridine, azetidine, tetrahydropyrrole, oxirane, oxetane, dioxetane, tetrahydropyrane, tetrahydrofurane, tetrahydro-2H-thiopyran, dioxane, dioxolane, oxathiolane, oxazolidine, thiirane, thietane, thiolane, thiane, thiazolidine, piperidine, piperazine, morpholine or azepane. Cycloalkyl radicals $C_{3-9}$, as defined in the present invention, are optionally mono- or polysubstituted by substitutents independently selected from a $C_{1-6}$ alkyl group, a linear or branched $C_{1-6}$ alkoxy group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —NHR', —NR'R" whereby R' and optionally R" for each substituent independently represents a linear or branched $C_{1-6}$-alkyl group.

An aryl radical, as referred to in the present invention, is understood as meaning ring systems with at least one aromatic ring but without heteroatoms even in only one of the rings. These aryl radicals may optionally be mono- or polysubstituted by substitutents independently selected from a $C_{1-6}$ alkyl group, a linear or branched $C_{1-6}$ alkoxy group, an optionally at least mono-substituted phenyl group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —N(C=O) OR', —NHR', —NR'R" whereby R' and optionally R" for each substituent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

A heteroaryl radical, is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-6}$ alkyl group, a linear or branched $C_{1-6}$ alkoxy group, F, Cl, I, Br, CF$_3$, CH$_2$F, CHF$_2$, CN, OH, SH, NH$_2$, oxo, (C=O)R', SR', SOR', SO$_2$R', NHR', NR'R" whereby R' and optionally R" for each substitutent independently represents a linear or branched $C_{1-6}$ alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidzole, carbazole and quinazoline.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

Cyclyl groups/radicals or cyclic systems, as defined in the present invention, comprise any saturated, unsaturated or aromatic carbocyclic ring systems which contain optionally at least one heteroatom as ring member and which are optionally at least mono-substituted. Cyclyl groups or cyclic systems preferably comprise aryl, heteroaryl, cyclyl, heterocyclyl and/or spiro ring systems.

Heterocyclyl groups/radicals or heterocyclic systems, as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, C, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$-alkoxy.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular preferred embodiment of the invention $R_1$ is cyclopropyl, adamantyl or a group with the following formula:

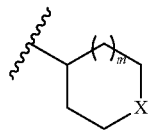

where X represents a —$CH_2$—, —O—, —$NR_{17}$— or —S— and m=0 or 1, being $R_{17}$ a $C_{1-6}$ alkyl, a benzyl or a hydrogen.

In another preferred embodiment of the invention $R_2$ is hydrogen or a $C_{1-6}$ alkyl.

In another preferred embodiment of the invention $R_3$ and $R_4$ are independently selected from the group consisting of hydrogen; halogen; —$NO_2$; —$CF_3$; —OH; —SH; —$NR_5R_6$; —CN; a substituted or unsubstituted, branched or unbranched $C_{1-6}$ alkyl; —NHC(O)$NHR_7$; —C(O)$OR_8$; —$OR_9$; —$SR_{12}$; —$SO_2NR_{15}R_{16}$ or a group selected from:

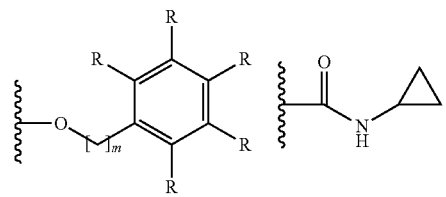

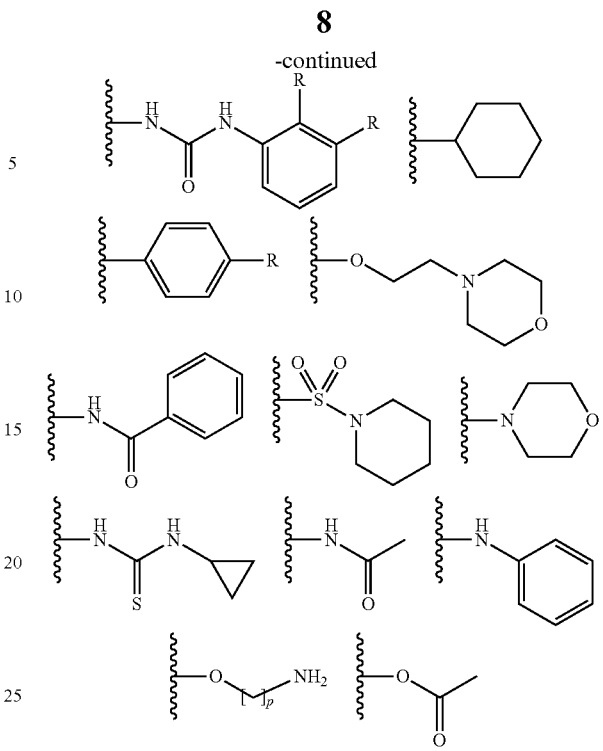

where R independently represents a hydrogen; substituted or unsubstituted, branched or unbranched $C_{1-6}$alkyl, an —OH or a halogen and where m=0 or 1 and p=3 or 4.

The preferred embodiment of the invention comprises compounds of formula (I) where $R_1$ is cyclopropyl; adamantyl; or the following group:

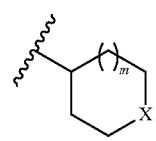

where X represents a —$CH_2$—, —O—, —NH—, —$NR_{17}$— or —S— and m=0 or 1 being $R_{17}$ a $C_{1-6}$ alkyl or a hydrogen; $R_2$ is hydrogen or $C_{1-6}$ alkyl;
$R_3$ and $R_4$ are independently selected from the group consisting of hydrogen; halogen; —$NO_2$; —$CF_3$; —OH; —SH; —$NR_5R_6$; —CN; a substituted or unsubstituted, branched or unbranched $C_{1-6}$alkyl; —NHC(O)$NHR_7$; —C(O)$OR_8$; —$OR_9$; —$SR_{12}$; —$SO_2NR_{15}R_{16}$ or a group selected from:

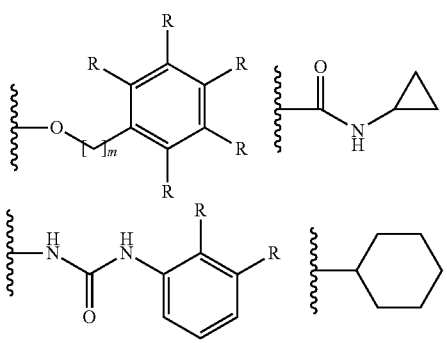

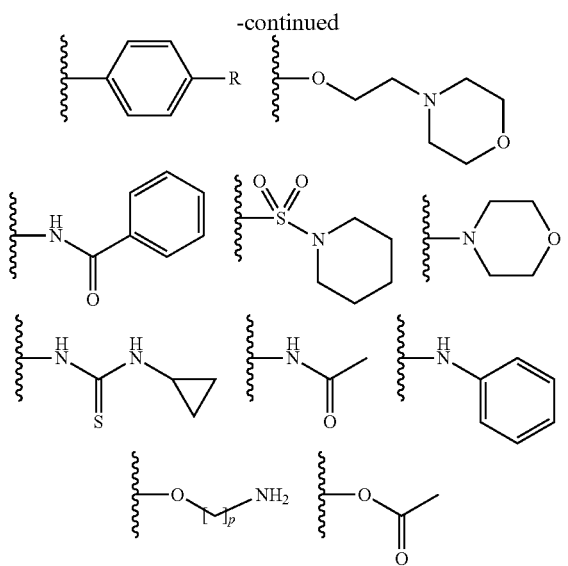

where R independently represents a hydrogen; substituted or unsubstituted, branched or unbranched $C_{1-6}$alkyl; an —OH or a halogen and where m=0 or 1 and p=3 or 4.

The compounds of the invention are preferably in neutral form, the form of a base or acid, in the form of a salt, preferably a physiologically acceptable salt, in the form of a solvate or of a polymorph and/or in the form of in the form of its racemate, pure stereoisomers, especially enantiomers or diastereomers or in the form of mixtures of stereoisomers, especially enantiomers or diastereomers, and/or in any mixing ratio. Compounds of formula (I) can be in the cis-isomer or in trans-isomer form accordingly to:

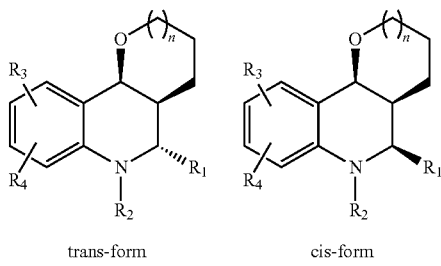

trans-form        cis-form

A preferred embodiment is represented by compound of general formula (I) in the cis-isomer form.

In preferred variants of the invention, the sigma ligands of formula (I) is selected from:

(4aSR*,5RS*,10bSR*)-9-(3-chlorophenoxy)-5-cyclohexyl-3,4,4a,5,6,10b-hexahydro-2H-pyrano[3,2-c]quinoline hydrochloride;

(4aSR*,5SR*,10bSR*)-9-(3-chlorophenoxy)-5-cyclohexyl-3,4,4a,5,6,10b-hexahydro-2H-pyrano[3,2-c]quinoline hydrochloride;

1-(3-chloro-2-methylphenyl)-3-((4aSR*,5SR*,10bSR*)-5-cyclohexyl-3,4,4a,5,6,10b-hexahydro-2H-pyrano[3,2-c]quinolin-9-yl)urea hydrochloride;

N-((4aSR*,5SR*,10bSR*)-5-cyclohexyl-3,4,4a,5,6,10b-hexahydro-2H-pyrano[3,2-c]quinolin-9-yl)pentanamide hydrochloride;

(4aSR*,5SR*,10bSR*)-5-cyclohexyl-N-cyclopropyl-3,4,4a,5,6,10b-hexahydro-2H-pyrano[3,2-c]quinoline-9-carboxamide hydrochloride;

(4aSR*,5RS*,10bSR*)-5-(1-benzylpiperidin-4-yl)-9-(isopentyloxy)-3,4,4a,5,6,10b-hexahydro-2H-pyrano[3,2-c]quinoline hydrochloride;

(4aSR*,5RS*,10bSR*)-5-cyclohexyl-3,4,4a,5,6,10b-hexahydro-2H-pyrano[3,2-c]quinolin-10-amine;

(4aSR*,5RS*,10bSR*)-5-cyclohexyl-9-(trifluoromethoxy)-3,4,4a,5,6,10b-hexahydro-2H-pyrano[3,2-c]quinoline;

(4aSR*,5SR*,10bSR*)-5-cyclohexyl-8-ethyl-3,4,4a,5,6,10b-hexahydro-2H-pyrano[3,2-c]quinoline;

(4aSR*,5SR*,10bSR*)-ethyl 5-cyclohexyl-3,4,4a,5,6,10b-hexahydro-2H-pyrano[3,2-c]quinoline-9-carboxylate hydrochloride;

(4aSR*,5RS*,10bSR*)-5-cyclohexyl-3,4,4a,5,6,10b-hexahydro-2H-pyrano[3,2-c]quinolin-9-ol;

(4aSR*,5RS*,10bSR*)-5-cyclohexyl-10-nitro-3,4,4a,5,6,10b-hexahydro-2H-pyrano[3,2-c]quinoline;

(4aSR*,5RS*,10bSR*)-9-tert-butyl-5-cyclopropyl-3,4,4a,5,6,10b-hexahydro-2H-pyrano[3,2-c]quinoline;

(4aSR*,5RS*,10bSR*)-9-tert-butyl-5-cyclohexyl-3,4,4a,5,6,10b-hexahydro-2H-pyrano[3,2-c]quinoline;

(4aSR*,5RS*,10bSR*)-5-cyclohexyl-9-methoxy-3,4,4a,5,6,10b-hexahydro-2H-pyrano[3,2-c]quinoline;

(4aSR*,5RS*,10bSR*)-9-butoxy-5-cyclohexyl-3,4,4a,5,6,10b-hexahydro-2H-pyrano[3,2-c]quinoline hydrochloride;

(4aSR*,5SR*,10bSR*)-9-butoxy-5-cyclohexyl-3,4,4a,5,6,10b-hexahydro-2H-pyrano[3,2-c]quinoline hydrochloride;

(4aSR*,5RS*,10bSR*)-5-cyclopentyl-9-(trifluoromethoxy)-3,4,4a,5,6,10b-hexahydro-2H-pyrano[3,2-c]quinoline hydrochloride;

(4aSR*,5RS*,10bSR*)-5-cyclohexyl-9-(trifluoromethylthio)-3,4,4a,5,6,10b-hexahydro-2H-pyrano[3,2-c]quinoline hydrochloride;

(4aSR*,5RS*,10bSR*)-5-cyclohexyl-9-methyl-3,4,4a,5,6,10b-hexahydro-2H-pyrano[3,2-c]quinoline hydrochloride;

(4aSR*,5RS*,10bSR*)-5-cyclohexyl-9-fluoro-3,4,4a,5,6,10b-hexahydro-2H-pyrano[3,2-c]quinoline hydrochloride;

(4aSR*,5RS*,10bSR*)-5-cyclohexyl-9-isopropyl-3,4,4a,5,6,10b-hexahydro-2H-pyrano[3,2-c]quinoline hydrochloride;

(4aSR*,5RS*,10bSR*)-5-cyclohexyl-7-(trifluoromethoxy)-3,4,4a,5,6,10b-hexahydro-2H-pyrano[3,2-c]quinoline hydrochloride;

(4aSR*,5RS*,10bSR*)-9-butyl-5-cyclohexyl-3,4,4a,5,6,10b-hexahydro-2H-pyrano[3,2-c]quinoline hydrochloride;

(4aSR*,5RS*,10bSR*)-5,9-dicyclohexyl-3,4,4a,5,6,10b-hexahydro-2H-pyrano[3,2-c]quinoline hydrochloride;

(4aSR*,5RS*,10bSR*)-5-cyclohexyl-9-phenoxy-3,4,4a,5,6,10b-hexahydro-2H-pyrano[3,2-c]quinoline hydrochloride;

(4aSR*,5SR*,10bSR*)-5-cyclohexyl-9-(isopentyloxy)-3,4,4a,5,6,10b-hexahydro-2H-pyrano[3,2-c]quinoline hydrochloride;

(4aSR*,5SR*,10bSR*)-5-cyclohexyl-9-(isopentyloxy)-3,4,4a,5,6,10b-hexahydro-2H-pyrano[3,2-c]quinoline hydrochloride;

(3aSR*,4RS*,9bSR*)-8-butoxy-4-cyclohexyl-2,3,3a,4,5,9b-hexahydrofuro[3,2-c]quinoline hydrochloride;

(4aSR*,5RS*,10bSR*)-5-cyclohexyl-9-propoxy-3,4,4a,5,6,10b-hexahydro-2H-pyrano[3,2-c]quinoline hydrochloride;

(3aSR*,4RS*,9bSR*)-4-cyclohexyl-8-propoxy-2,3,3a,4,5,9b-hexahydrofuro[3,2-c]quinoline hydrochloride;

(3aSR*,4RS*,9bSR*)-4-cyclohexyl-8-(isopentyloxy)-2,3,3a,4,5,9b-hexahydrofuro[3,2-c]quinoline hydrochloride;
(3aSR*,4RS*,9bSR*)-propyl 4-cyclohexyl-2,3,3a,4,5,9b-hexahydrofuro[3,2-c]quinoline-8-carboxylate hydrochloride;
(3aSR*,4SR*,9bSR*)-propyl 4-cyclohexyl-2,3,3a,4,5,9b-hexahydrofuro[3,2-c]quinoline-8-carboxylate hydrochloride;
(4aSR*,5RS*,10bSR*)-5-cyclohexyl-9-phenyl-3,4,4a,5,6,10b-hexahydro-2H-pyrano[3,2-c]quinoline hydrochloride;
(3aSR*,4RS*,9bSR*)-4-cyclohexyl-8-(trifluoromethoxy)-2,3,3a,4,5,9b-hexahydrofuro[3,2-c]quinoline hydrochloride;
N-((4aSR*,5RS*,10bSR*)-5-cyclohexyl-3,4,4a,5,6,10b-hexahydro-2H-pyrano[3,2-c]quinolin-9-yl)acetamide hydrochloride;
N-((3aSR*,4RS*,9bSR*)-4-cyclohexyl-2,3,3a,4,5,9b-hexahydrofuro[3,2-c]quinolin-8-yl)acetamide hydrochloride;
(4aSR*,5RS*,10bSR*)-propyl 5-cyclohexyl-3,4,4a,5,6,10b-hexahydro-2H-pyrano[3,2-c]quinoline-9-carboxylate hydrochloride;
(3aSR*,4RS*,9bSR*)-8-butoxy-4-cyclohexyl-6-fluoro-2,3,3a,4,5,9b-hexahydrofuro[3,2-c]quinoline hydrochloride;
(3aSR*,4RS*,9bSR*)-4-cyclohexyl-8-(2-morpholinoethoxy)-2,3,3a,4,5,9b-hexahydrofuro[3,2-c]quinoline hydrochloride;
(3aSR*,4RS*,9bSR*)-8-butoxy-4-cyclohexyl-7-fluoro-2,3,3a,4,5,9b-hexahydrofuro[3,2-c]quinoline hydrochloride;
(3aSR*,4RS*,9bSR*)-4-cyclohexyl-8-phenyl-2,3,3a,4,5,9b-hexahydrofuro[3,2-c]quinoline hydrochloride;
(4aSR*,5RS*,10bSR*)-9-butoxy-5-cyclohexyl-8-fluoro-3,4,4a,5,6,10b-hexahydro-2H-pyrano[3,2-c]quinoline hydrochloride;
(3aSR*,4RS*,9bSR*)-4-cyclohexyl-8-nitro-2,3,3a,4,5,9b-hexahydrofuro[3,2-c]quinoline hydrochloride;
(4aSR*,5RS*,10bSR*)-5-cyclohexyl-9-iodo-3,4,4a,5,6,10b-hexahydro-2H-pyrano[3,2-c]quinoline hydrochloride;
(4aSR*,5RS*,10bSR*)-ethyl 5-cyclohexyl-3,4,4a,5,6,10b-hexahydro-2H-pyrano[3,2-c]quinoline-8-carboxylate hydrochloride;
(4aSR*,5RS*,10bSR*)-ethyl 5-cyclohexyl-3,4,4a,5,6,10b-hexahydro-2H-pyrano[3,2-c]quinoline-10-carboxylate hydrochloride;
(4aSR*,5RS*,10bSR*)-9-butoxy-5-(piperidin-4-yl)-3,4,4a,5,6,10b-hexahydro-2H-pyrano[3,2-c]quinoline;
N-((4aSR*,5RS*,10bSR*)-5-cyclohexyl-3,4,4a,5,6,10b-hexahydro-2H-pyrano[3,2-c]quinolin-9-yl)benzamide hydrochloride;
(3aSR*,4RS*,9bSR*)-4-cyclohexyl-8-phenoxy-2,3,3a,4,5,9b-hexahydrofuro[3,2-c]quinoline hydrochloride;
(4aSR*,5RS*,10bSR*)-5-cyclohexyl-9-ethyl-3,4,4a,5,6,10b-hexahydro-2H-pyrano[3,2-c]quinoline hydrochloride;
(4aSR*,5RS*,10bSR*)-9-phenoxy-5-(tetrahydro-2H-pyran-4-yl)-3,4,4a,5,6,10b-hexahydro-2H-pyrano[3,2-c]quinoline hydrochloride;
(4aSR*,5RS*,10bSR*)-methyl 5-cyclohexyl-3,4,4a,5,6,10b-hexahydro-2H-pyrano[3,2-c]quinoline-9-carboxylate hydrochloride;
(4aSR*,5RS*,10bSR*)-9-(4-chlorophenoxy)-5-cyclohexyl-3,4,4a,5,6,10b-hexahydro-2H-pyrano[3,2-c]quinoline hydrochloride;
(4aSR*,5RS*,10bSR*)-5-cyclopentyl-9-phenoxy-3,4,4a,5,6,10b-hexahydro-2H-pyrano[3,2-c]quinoline hydrochloride;
(4aSR*,5RS*,10bSR*)-5-cyclohexyl-9-p-tolyl-3,4,4a,5,6,10b-hexahydro-2H-pyrano[3,2-c]quinoline hydrochloride;
4-((4aSR*,5RS*,10bSR*)-5-cyclohexyl-3,4,4a,5,6,10b-hexahydro-2H-pyrano[3,2-c]quinolin-9-yl)phenol hydrochloride;
(4aSR*,5RS*,10bSR*)-5-cyclohexyl-9-pentyl-3,4,4a,5,6,10b-hexahydro-2H-pyrano[3,2-c]quinoline;
(4aSR*,5RS*,10bSR*)-5-cyclohexyl-9-pentyl-3,4,4a,5,6,10b-hexahydro-2H-pyrano[3,2-c]quinoline hydrochloride;
(4aSR*,5SR*,10bSR*)-5-cyclohexyl-9-pentyl-3,4,4a,5,6,10b-hexahydro-2H-pyrano[3,2-c]quinoline hydrochloride;
(4aSR*,5RS*,10bSR*)-5-cyclohexyl-9-(piperidin-1-ylsulfonyl)-3,4,4a,5,6,10b-hexahydro-2H-pyrano[3,2-c]quinoline hydrochloride;
(4aSR*,5RS*,10bSR*)-9-pentyl-5-(tetrahydro-2H-pyran-4-yl)-3,4,4a,5,6,10b-hexahydro-2H-pyrano[3,2-c]quinoline hydrochloride;
(4aSR*,5RS*,10bSR*)-5-cyclohexyl-9-morpholino-3,4,4a,5,6,10b-hexahydro-2H-pyrano[3,2-c]quinoline hydrochloride;
(4aSR*,5RS*,10bSR*)-5-adamantyl-9-phenoxy-3,4,4a,5,6,10b-hexahydro-2H-pyrano[3,2-c]quinoline hydrochloride;
(4aSR*,5RS*,10bSR*)-9-(2-chlorophenoxy)-5-cyclohexyl-3,4,4a,5,6,10b-hexahydro-2H-pyrano[3,2-c]quinoline hydrochloride;
(4aSR*,5RS*,10bSR*)-5-cyclohexyl-9-(2-morpholinoethoxy)-3,4,4a,5,6,10b-hexahydro-2H-pyrano[3,2-c]quinoline;
(4aSR*,5RS*,10bSR*)-propyl 5-adamantyl-3,4,4a,5,6,10b-hexahydro-2H-pyrano[3,2-c]quinoline-9-carboxylate hydrochloride;
(4aSR*,5RS*,10bSR*)-methyl 5-cyclohexyl-7-methyl-3,4,4a,5,6,10b-hexahydro-2H-pyrano[3,2-c]quinoline-8-carboxylate hydrochloride;
(4aSR*,5RS*,10bSR*)-ethyl 5-cyclohexyl-3,4,4a,5,6,10b-hexahydro-2H-pyrano[3,2-c]quinoline-7-carboxylate hydrochloride;
(4aSR*,5RS*,10bSR*)-9-phenoxy-5-(tetrahydro-2H-thiopyran-4-yl)-3,4,4a,5,6,10b-hexahydro-2H-pyrano[3,2-c]quinoline hydrochloride;
(4aSR*,5RS*,10bSR*)-methyl 5-cyclopentyl-7-methyl-3,4,4a,5,6,10b-hexahydro-2H-pyrano[3,2-c]quinoline-8-carboxylate hydrochloride;
(4aSR*,5RS*,10bSR*)-ethyl 5-cyclopentyl-3,4,4a,5,6,10b-hexahydro-2H-pyrano[3,2-c]quinoline-8-carboxylate hydrochloride;
(4aSR*,5RS*,10bSR*)-ethyl 5-cyclopentyl-3,4,4a,5,6,10b-hexahydro-2H-pyrano[3,2-c]quinoline-10-carboxylate hydrochloride;
(3aSR*,4RS*,9bSR*)-ethyl 4-cyclopentyl-2,3,3a,4,5,9b-hexahydrofuro[3,2-c]quinoline-7-carboxylate hydrochloride;
(3aSR*,4RS*,9bSR*)-ethyl 4-cyclopentyl-2,3,3a,4,5,9b-hexahydrofuro[3,2-c]quinoline-9-carboxylate hydrochloride;
1-((4aSR*,5RS*,10bSR*)-5-cyclohexyl-3,4,4a,5,6,10b-hexahydro-2H-pyrano[3,2-c]quinolin-9-yl)-3-cyclopropylthiourea hydrochloride;

(4aSR*,5RS*,10bSR*)-5-cyclopentyl-3,4,4a,5,6,10b-hexahydro-2H-pyrano[3,2-c]quinoline-9-carbonitrile hydrochloride;
(4aSR*,5RS*,10bSR*)-5-cyclopentyl-9-(piperidin-1-ylsulfonyl)-3,4,4a,5,6,10b-hexahydro-2H-pyrano[3,2-c]quinoline hydrochloride;
(3aSR*,4RS*,9bSR*)-4-cyclopentyl-8-(piperidin-1-ylsulfonyl)-2,3,3a,4,5,9b-hexahydrofuro[3,2-c]quinoline;
(4aSR*,5RS*,10bSR*)-5-cyclopentyl-N,N-dimethyl-3,4,4a,5,6,10b-hexahydro-2H-pyrano[3,2-c]quinoline-9-sulfonamide hydrochloride;
(4aSR*,5RS*,10bSR*)-5-cyclopentyl-N,N-diethyl-3,4,4a,5,6,10b-hexahydro-2H-pyrano[3,2-c]quinoline-9-sulfonamide hydrochloride;
(3aSR*,4RS*,9bSR*)-4-cyclohexyl-2,3,3a,4,5,9b-hexahydrofuro[3,2-c]quinolin-8-ol hydrochloride;
(3aSR*,4RS*,9bSR*)-4-cyclohexyl-8-pentyl-2,3,3a,4,5,9b-hexahydrofuro[3,2-c]quinoline hydrochloride;
(3aSR*,4RS*,9bSR*)-8-pentyl-4-(tetrahydro-2H-pyran-4-yl)-2,3,3a,4,5,9b-hexahydrofuro[3,2-c]quinoline hydrochloride;
(3aSR*,4RS*,9bSR*)-8-(4-chlorophenoxy)-4-cyclohexyl-2,3,3a,4,5,9b-hexahydrofuro[3,2-c]quinoline;
(3aSR*,4RS*,9bSR*)-8-(4-chlorophenoxy)-4-cyclohexyl-2,3,3a,4,5,9b-hexahydrofuro[3,2-c]quinoline hydrochloride;
(3aSR*,4RS*,9bSR*)-8-(benzyloxy)-4-cyclohexyl-2,3,3a,4,5,9b-hexahydrofuro[3,2-c]quinoline hydrochloride;
(4aSR*,5RS*,10bSR*)-5-cyclohexyl-N-propyl-3,4,4a,5,6,10b-hexahydro-2H-pyrano[3,2-c]quinoline-9-sulfonamide;
(4aSR*,5RS*,10bSR*)-5-cyclohexyl-9-(4-fluorobenzyloxy)-3,4,4a,5,6,10b-hexahydro-2H-pyrano[3,2-c]quinoline hydrochloride;
(3aSR*,4RS*,9bSR*)-4-cyclohexyl-8-(4-fluorobenzyloxy)-2,3,3a,4,5,9b-hexahydrofuro[3,2-c]quinoline hydrochloride;
(3aSR*,4RS*,9bSR*)-4-cyclohexyl-8-(3,4-dichlorophenoxy)-2,3,3a,4,5,9b-hexahydrofuro[3,2-c]quinoline hydrochloride;
(4aSR*,5RS*,10bSR*)-5-cyclohexyl-9-(3,4-dichlorophenoxy)-3,4,4a,5,6,10b-hexahydro-2H-pyrano[3,2-c]quinoline hydrochloride;
(3aSR*,4RS*,9bSR*)-ethyl 4-cyclohexyl-2,3,3a,4,5,9b-hexahydrofuro[3,2-c]quinoline-8-carboxylate hydrochloride;
(3aSR*,4RS*,9bSR*)-8-pentyl-4-(tetrahydro-2H-thiopyran-4-yl)-2,3,3a,4,5,9b-hexahydrofuro[3,2-c]quinoline hydrochloride;
(3aSR*,4RS*,9bSR*)-8-(2-chlorophenoxy)-4-cyclohexyl-2,3,3a,4,5,9b-hexahydrofuro[3,2-c]quinoline hydrochloride;
(3aSR*,4RS*,9bSR*)-4-cyclohexyl-N-phenyl-2,3,3a,4,5,9b-hexahydrofuro[3,2-c]quinolin-8-amine hydrochloride;
(4aSR*,5RS*,10bSR*)-5-cyclohexyl-9-ethoxy-3,4,4a,5,6,10b-hexahydro-2H-pyrano[3,2-c]quinoline hydrochloride;
N-((3aSR*,4RS*,9bSR*)-4-cyclohexyl-2,3,3a,4,5,9b-hexahydrofuro[3,2-c]quinolin-8-yl)benzamide hydrochloride;
(4aSR*,5RS*,10bSR*)-9-(isopentyloxy)-5-(piperidin-4-yl)-3,4,4a,5,6,10b-hexahydro-2H-pyrano[3,2-c]quinoline hydrochloride;
(4aSR*,5RS*,10bSR*)-9-(isopentyloxy)-5-(tetrahydro-2H-pyran-4-yl)-3,4,4a,5,6,10b-hexahydro-2H-pyrano[3,2-c]quinoline hydrochloride;
(3aSR*,4RS*,9bSR*)-4-cyclohexyl-6-(isopentyloxy)-2,3,3a,4,5,9b-hexahydrofuro[3,2-c]quinoline;
(3aSR*,4RS*,9bSR*)-4-cyclohexyl-8-morpholino-2,3,3a,4,5,9b-hexahydrofuro[3,2-c]quinoline hydrochloride;
(4aSR*,5RS*,10bSR*)-9-methoxy-5-(piperidin-4-yl)-3,4,4a,5,6,10b-hexahydro-2H-pyrano[3,2-c]quinoline hydrochloride;
(4aSR*,5RS*,10bSR*)-5-cyclopentyl-9-(isopentyloxy)-3,4,4a,5,6,10b-hexahydro-2H-pyrano[3,2-c]quinoline hydrochloride;
3-((3aSR*,4RS*,9bSR*)-4-cyclohexyl-2,3,3a,4,5,9b-hexahydrofuro[3,2-c]quinolin-8-yloxy)propan-1-amine hydrochloride;
1-((4aSR*,5RS*,10bSR*)-5-cyclohexyl-3,4,4a,5,6,10b-hexahydro-2H-pyrano[3,2-c]quinolin-9-yl)-3-(2,3-dichlorophenyl)urea hydrochloride;
(4aSR*,5RS*,10bSR*)-9-methoxy-5-(1-phenethylpiperidin-4-yl)-3,4,4a,5,6,10b-hexahydro-2H-pyrano[3,2-c]quinoline hydrochloride;
(4aSR*,5RS*,10bSR*)-5-(1-(4-chlorobenzyl)piperidin-4-yl)-9-methoxy-3,4,4a,5,6,10b-hexahydro-2H-pyrano[3,2-c]quinoline hydrochloride;
(4aSR*,5RS*,10bSR*)-5-(1-ethylpiperidin-4-yl)-9-(isopentyloxy)-3,4,4a,5,6,10b-hexahydro-2H-pyrano[3,2-c]quinoline hydrochloride;
4-((4aSR*,5RS*,10bSR*)-5-cyclohexyl-3,4,4a,5,6,10b-hexahydro-2H-pyrano[3,2-c]quinolin-9-yloxy)butan-1-amine hydrochloride;
3-((4aSR*,5RS*,10bSR*)-5-cyclohexyl-3,4,4a,5,6,10b-hexahydro-2H-pyrano[3,2-c]quinolin-9-yloxy)propan-1-amine hydrochloride;
(4aSR*,5RS*,10bSR*)-5-cyclohexyl-9-(methylthio)-3,4,4a,5,6,10b-hexahydro-2H-pyrano[3,2-c]quinoline hydrochloride;
(4aS,5R,10bS)-9-(isopentyloxy)-5-(tetrahydro-2H-pyran-4-yl)-3,4,4a,5,6,10b-hexahydro-2H-pyrano[3,2-c]quinoline hydrochloride;
(4aSR*,5RS*,10bSR*)-5-cyclohexyl-9-(isopentyloxy)-6-methyl-3,4,4a,5,6,10b-hexahydro-2H-pyrano[3,2-c]quinoline;
(4aSR*,5RS*,10bSR*)-9-tert-butyl-5-cyclopropyl-6-ethyl-3,4,4a,5,6,10b-hexahydro-2H-pyrano[3,2-c]quinoline.
or their pharmaceutically acceptable salts, stereoisomers, solvates or a prodrug thereof.

Any compound referred to herein is intended to represent such specific compound as well as certain variations or forms. In particular, compounds referred to herein may have asymmetric centers and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

A specific embodiment of the invention is that in which the pyrano or furano quinolines of the invention represent a compound with the general formula (Ia) or (Ib):

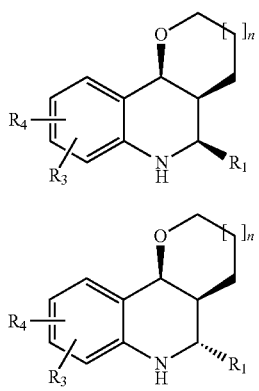

where the different substituent have the same meanings expressed before.

An additional specific embodiment of the invention is provided where pyrano or furano quinolines of the invention are represented by general formula (Id):

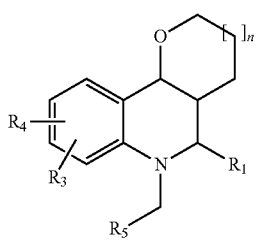

Again substituents are as expressed before.

Another specific embodiment is that in which the compounds of the invention have the general formula (Ie):

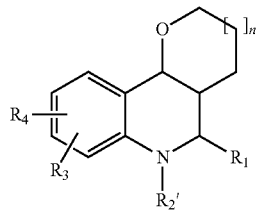

the substituents having the same meaning as for compounds of general formula (I).

In another aspect, the invention refers to the processes for obtaining the compounds of general formula (I). Several procedures have been developed for obtaining all the compound derivatives of the invention, herein the procedures will be explained below in methods A to D.

Method A

A process is described for obtaining compounds of formula (Ia) and (Ib) as a racemic mixture when $R_2$ is H in compound of general formula I:

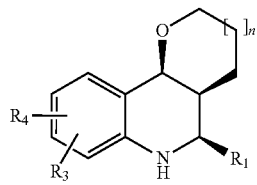

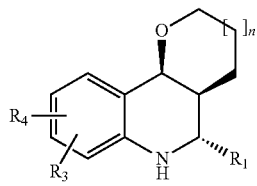

where $R_1$, $R_3$, $R_4$ and n have the same meaning of compounds of formula (I), the process comprising the multicomponent reaction in an organic solvent and in the presence of a protic or Lewis acid between compounds of general formula (II), (III) and (IV):

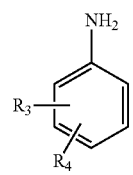

Compounds of general formula (Ia) and/or (Ib) can be prepared in a multicomponent reaction (MCR) of aldehydes (II), anilines (III) and dihydrofurans or dihydropyrans of formula (IV) catalyzed by a protic or Lewis acid such as Mg(ClO$_4$)$_2$, but not limited to, in an organic solvent such as acetonitrile by methods reported in the literature (e.g. Kamble, V. T. et al. Synlett, 2007, 1379-1382; Xia, M. et al. Synlett, 2005, 2357-2361).

Compounds of formula II, III and IV are commercially available or can be prepared by conventional methods. In the process described above, whereas necessary, reactive groups may be protected using protection and deprotection methodology well known by those skilled in the art (e.g. Greene, T. W., Wutz P. M. "Protective Groups in Organic Synthesis" Wiley, 1999).

When $R_3$ or $R_4$ is a urea, thiourea or —NR$_{10}$C(O)R$_{11}$, compounds can be obtained by direct MCR or starting from compounds of formula (Ia) and/or (Ib) where $R_3$ or $R_4$ is an amino group. In this case, the reaction is typically carried out in an aprotic solvent such as dichloromethane in the presence of an organic base such as triethylamine or diisopropylethylamine (DIPEA). Optionally, when $R_3$ or $R_4$ is —NR$_{10}$C(O)R$_{11}$, a coupling agent such as 1-ethyl-3-(3-dimethylaminopropyl)carbodiimide (EDC) can be used.

When $R_3$ or $R_4$ is a —C(O)NR$_{13}$R$_{14}$, compounds of formula (Ia) and/or (Ib) can be obtained by direct MCR or by amidation reaction from carboxylic acids. Amidation reaction is carried out in an aprotic solvent such as dichloromethane in the presence of an organic base such as DIPEA or triethylamine with a coupling agent such as EDC.

When $R_1$ is a N-substituted piperidine, compounds can be obtained by reductive amination with the corresponding aldehyde. Reductive amination is typically carried out in the presence of a reducing agent such as NaBH(OAc)$_3$ or NaBH$_3$CN in a solvent such as methanol or dichloroethane at temperature of solvent reflux or under heated microwave conditions.

Method B

When $R_2$ is different from H in compounds of general formula I, there are three methods for preparing compounds of formula (Ic), (Id) and (Ie). These are method B, method C and method D respectively.

Method B represents an alternative for preparing intermediate compounds of formula (I) when $R_2$ is a —COR$_5$ group, that is, compound of general formula (Ic):

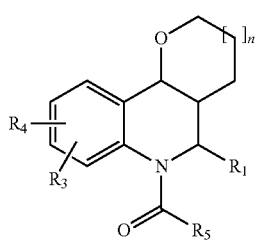

(Ic)

where $R_1$, $R_3$, $R_4$, $R_5$ and n have the same meaning as for compounds of formula (I).

The process for preparing compounds of formula (Ic) comprises the reaction in an aprotic solvent and in the presence of an organic base between a compound of formula (Ia) or (Ib) with a compound (VI):

(VI)

alternatively, the reaction can be carried out in neat acetic anhydride.

Acylation of compounds of formula (Ia) and/or (Ib) is preferably carried out in an aprotic solvent such as dichloromethane in the presence of an organic base such as DIPEA with an acyl chloride. Alternatively, the reaction can be carried out in neat acetic anhydride.

Method C

Method C is sequential to method B and represents the alternative to prepare compounds of formula (I) where when $R_2$ is a —CH$_2$R$_5$ group. The process for the preparation of compounds of general formula (Id):

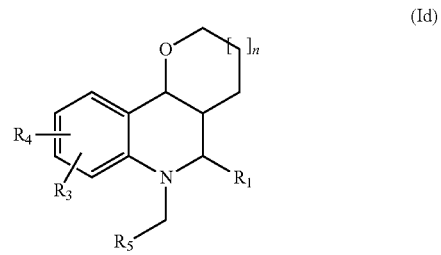

(Id)

where $R_1$, $R_3$, $R_4$, $R_5$ and n have the same meaning as for formula (I) comprises the reduction of a compounds of general formula (Ic).

Reduction of compounds of formula (Ic) is typically carried out with a reducing agent such as lithium aluminium hydride in an aprotic solvent such as tetrahydrofuran preferably at reflux temperature.

Method D

Method D is the alternative for preparing compounds of general formula (I) where $R_2$ is a C$_{1-6}$ alkyl. The process for the preparation of a compound of general formula (Ie):

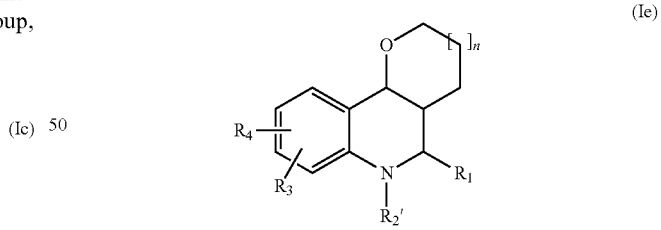

(Ie)

where $R_1$, $R_3$, $R_4$ and n have the same meaning as for compounds of formula (I) and $R_{2'}$ is a substituted or unsubstituted, branched or unbranched C$_{1-6}$ alkyl comprises the reaction in a protic solvent and in the presence of a reducing agent of a compound of general formula (Ia) or (Ib) with an aldehyde having the corresponding number of carbon atoms and structure desired for substituent $R_{2'}$.

The reaction of compounds of formula (Ia) and/or (Ib) with aldehydes (V) is preferably carried out in a protic solvent such as methanol with a reducing reagent such as NaBH(OAc)$_3$ or NaBH$_3$CN at temperature of solvent reflux or under heated microwave conditions.

The general synthetic route describing the methods A to D is shown in the following schemes 1 and 2:

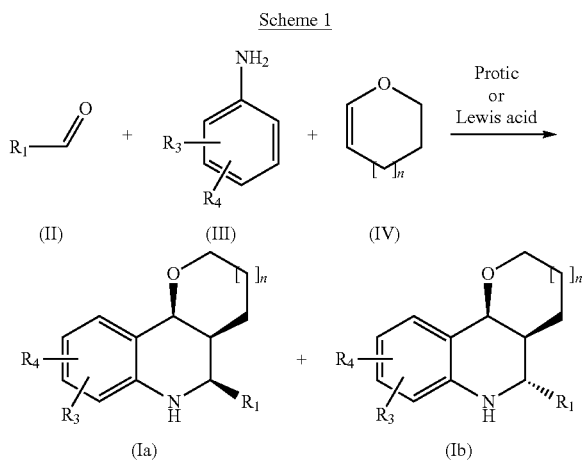

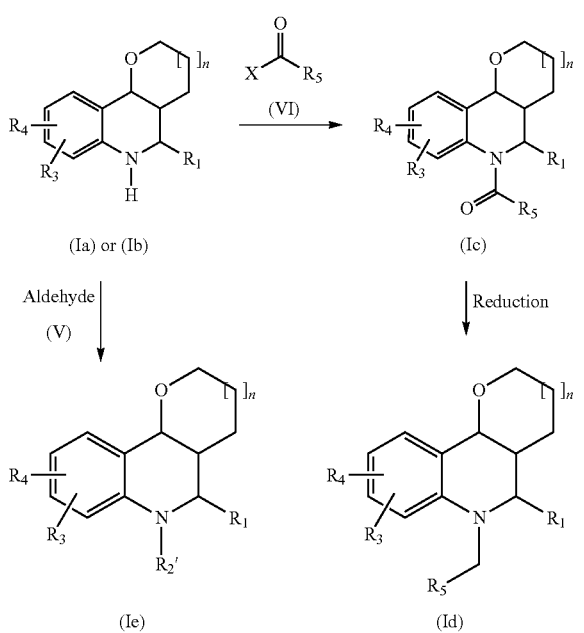

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. Therefore, compounds of general formula (I) are useful as medicaments.

They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment of disorders and diseases mediated by sigma receptors, as explained before.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragées, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Described below are a number of examples by way of illustration of the invention and do not limit it in anyway.
Preparation of Compounds of Formula (Ia) and/or (Ib)

EXAMPLE 1 and 2

Synthesis of (4aSR*,5RS*,10bSR*)-9-(3-chlorophenoxy)-5-cyclohexyl-3,4,4a,5,6,10b-hexahydro-2H-pyrano[3,2-c]quinoline hydrochloride and (4aSR*,5SR*,10bSR*)-9-(3-chlorophenoxy)-5-cyclohexyl-3,4,4a,5,6,10b-hexahydro-2H-pyrano[3,2-c]quinoline hydrochloride

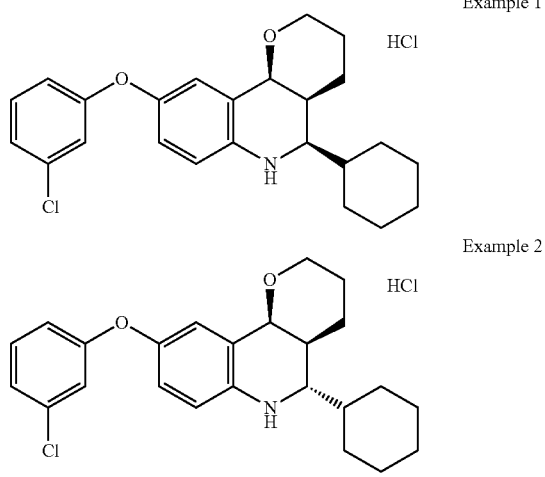

Example 1

Example 2

To a solution of 4-(3-chlorophenoxy)aniline (220 mg, 1 mmol, 1 equiv.) in dry MeCN (3 mL) under argon atmosphere was added cyclohexanecarbaldehyde (121 μL, 1 mmol, 1 equiv.) and 3,4-dihydro-2H-pyran (90 μL, 1 mmol, 1 equiv.) sequentially, followed by Mg(ClO$_4$)$_2$ (12.3 mg, 0.05 mmol, 0.05 equiv.). The reaction mixture was stirred at r.t. overnight. The solvent was removed under reduced pressure and the residue taken up in CH$_2$Cl$_2$ and passed through Decalite. The solvent of the filtrate was removed under reduced pressure and the crude crystallized from AcOEt to afford pure cis diastereomer (4aSR*,5RS*,10bSR*)-9-(3-chlorophenoxy)-5-cyclohexyl-3,4,4a,5,6,10b-hexahydro-2H-pyrano[3,2-c]quinoline (138 mg, 34%) as white solid. The solvent from the mother liquid was evaporated and the remaining residue purified by Combiflash chromatography (SiO$_2$, c-Hexane/AcOEt up to 10%) to obtain additionally 144 mg of the cis diastereomer (overall yield cis 71%) along with the 78 mg of trans diastereomer (4aSR*,5SR*,10bSR*)-9-(3-chlorophenoxy)-5-cyclohexyl-3,4,4a,5,6,10b-hexahydro-2H-pyrano[3,2-c] (18%) as yellow oil. The corresponding hydrochloride salts of the cis and trans diastereomer were prepared as follows.

To an ice-cooled solution of (4aSR*,5RS*,10bSR*)-9-(3-chlorophenoxy)-5-cyclohexyl-3,4,4a,5,6,10b-hexahydro-2H-pyrano[3,2-c]quinoline (50 mg, 0.126 mmol) in acetone (500 μL) was added dropwise a 2 M HCl solution (in ether, 69 μL, 1.38 mmol, 1.1 equiv.). After 30 min. stirring at r.t., a solid had precipitated. The solid was filtered off and dried in vacuum to give (4aSR*,5RS*,10bSR*)-9-(3-chlorophenoxy)-5-cyclohexyl-3,4,4a,5,6,10b-hexahydro-2H-pyrano[3,2-c]quinoline hydrochloride (42 mg, 76%) as white solid. (Example 1).

$^1$H NMR (CDC$_3$) δ ppm: 8.12-7.93 (m, 1H), 7.26-7.22 (m, 1H), 7.21 (s, 1H), 7.10 (d, J=7.8 Hz, 1H), 7.00 (s, 1H), 6.93 (d, J=6.8 Hz, 1H), 6.88 (d, J=8.3 Hz, 1H), 4.89 (d, J=4.4 Hz, 1H), 3.62 (d, J=10.9 Hz, 1H), 3.36-3.18 (m, 2H), 2.69-2.46 (m, 2H), 2.30-2.11 (m, 1H), 1.95-1.75 (m, 4H), 1.75-1.45 (m, 3H), 1.42-1.12 (m, 4H), 1.12-0.95 (m, 1H).

To an ice-cooed solution of (4aSR*,5SR*,10bSR*)-9-(3-chlorophenoxy)-5-cyclohexyl-3,4,4a,5,6,10b-hexahydro-2H-pyrano[3,2-c]quinoline (60 mg, 0.151 mmol) in acetone (500 μL) was added dropwise a 2 M HCl solution (in ether, 83 μL, 0.166 mmol, 1.1 equiv.). After 30 min. stirring at r.t., a solid had precipitated. The solid was filtered off and dried in vacuum to give (4aSR*,5SR*,10bSR*)-9-(3-chlorophenoxy)-5-cyclohexyl-3,4,4a,5,6,10b-hexahydro-2H-pyrano[3,2-c]quinoline hydrochloride (52 mg, 79%) as white solid. (Example 2).

$^1$H NMR (CDC$_3$) δ ppm: 8.11 (d, J=7.9 Hz, 1H), 7.25 (t, J=8.1 Hz, 1H), 7.10 (d, J=7.9 Hz, 1H), 7.06 (d, J=2.0 Hz, 1H), 7.02 (s, 1H), 6.92 (dd, J=8.8, 2.2 Hz, 1H), 6.88 (dd, J=8.4, 1.7 Hz, 1H), 4.57 (d, J=2.5 Hz, 1H), 3.84 (dt, J=10.3, 3.9 Hz, 1H), 3.72-3.58 (m, 2H), 2.55-2.45 (m, 1H), 2.05-1.94 (m, 2H), 1.93-1.74 (m, 6H), 1.74-1.60 (m, 2H), 1.59-1.43 (m, 2H), 1.39-1.16 (m, 3H).

EXAMPLE 3

1-(3-chloro-2-methylphenyl)-3-((4aSR*,5SR*,10bSR*)-5-cyclohexyl-3,4,4a,5,6,10b-hexahydro-2H-pyrano[3,2-c]quinolin-9-yl)urea hydrochloride

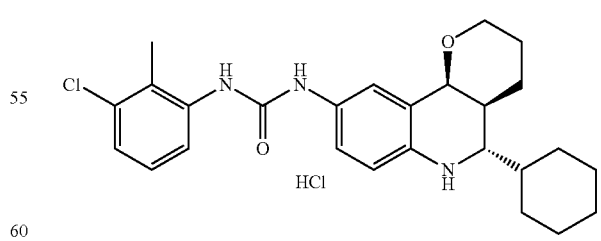

Step 1. To an ice-cooled solution of tert-butyl (4aSR*,5SR*,10bSR*)-5-cyclohexyl-3,4,4a,5,6,10b-hexahydro-2H-pyrano[3,2-c]quinolin-9-ylcarbamate (prepared according to the method described in example 1) (227 mg, 0.587 mmol) in CH$_2$Cl$_2$ (5 mL) under argon atmosphere was added TFA (1.5 mL) dropwise. The reaction solution was allowed to reach r.t.

and stirred overnight. The mixture was cooled down and 0.5 N NaOH solution was added until basic pH. The product was extracted with CH$_2$Cl$_2$ three times. The combined organic fractions were washed with sat. NaCl solution, dried over Na$_2$SO$_4$, and the solvent removed under reduced pressure after filtration giving (4aSR*,5SR*,10bSR*)-5-cyclohexyl-3,4,4a,5,6,10b-hexahydro-2H-pyrano[3,2-c]quinolin-9-amine (145 mg, 86%) as orange viscous solid. The product was used without further purification.

Step 2. To a solution of (4aSR*,5SR*,10bSR*)-5-cyclohexyl-3,4,4a,5,6,10b-hexahydro-2H-pyrano[3,2-c]quinolin-9-amine (74 mg, 0.26 mmol, 1 equiv.) in dry CH$_2$Cl$_2$ (5 mL) under argon atmosphere was added 1-chloro-3-isocyanato-2-methylbenzene (45 µL, 0.34 mmol, 1.32 equiv.) followed by NEt$_3$ (54 µL, 0.38 mmol, 1.5 equiv.). After stirring overnight at r.t., the reaction mixture was diluted with CH$_2$Cl$_2$ and quenched with H$_2$O. The phases were separated and the aqueous phase extracted with CH$_2$Cl$_2$ twice. The combined organic phases were dried over MgSO$_4$ and the solvent removed under reduced pressure after filtration The residue was purified by Combiflash chromatography (SiO$_2$, c-Hexane/AcOEt) to afford 1-(3-chloro-2-methylphenyl)-3-((4aSR*,5SR*,10bSR*)-5-cyclohexyl-3,4,4a,5,6,10b-hexahydro-2H-pyrano[3,2-c]quinolin-9-yl)urea (72 mg, 63%) as white solid. The compound was prepared as hydrochloride salt following the method described in example 1. $^1$H NMR (CD$_3$OD) δ ppm: 7.68-7.46 (m, 3H), 7.38-7.08 (m, 3H), 4.66-4.47 (m, 1H), 4.01 (d, J=10.7 Hz, 1H), 3.74 (td, J=11.3, 2.0 Hz, 1H), 3.88-3.58 (m, 1H), 2.35 (s, 3H), 2.27-1.62 (m, 10H), 1.62-1.14 (m, 6H).

EXAMPLE 4

Synthesis of N-((4aSR*,5SR*,10bSR*)-5-cyclohexyl-3,4,4a,5,6,10b-hexahydro-2H-pyrano[3,2-c]quinolin-9-yl)pentanamide hydrochloride

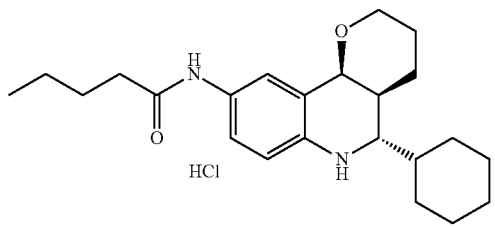 [SMILES: CCCCC(=O)Nc1ccc2c(c1)[C@H]1OCCC[C@H]1[C@H](C1CCCCC1)N2 ; Cl]

To a stirred solution of (4aSR*,5SR*,10bSR*)-5-cyclohexyl-3,4,4a,5,6,10b-hexahydro-2H-pyrano[3,2-c]quinolin-9-amine (prepared as described for example 3) (60 mg, 0.21 mmol, 1 equiv.) in dry CH$_2$Cl$_2$ under argon atmosphere was added valeric acid (23 µL, 0.21 mmol, 1 equiv.) followed by DIPEA (72 µL, 0.43 mmol, 2 equiv) and EDC (40 mg, 0.21 mmol, 1 equiv.). After stirring for 1 day at r.t., the reaction solution is diluted with CH$_2$Cl$_2$ and then sat. NaHCO$_3$ solution was added. The phases were separated and the aqueous phase extracted with CH$_2$Cl$_2$ twice. The combined organic fractions were dried over Na$_2$SO$_4$ and the solvent removed under reduced pressure after filtration. The residue was purified by Combiflash chromatography (SiO$_2$, c-Hexane/AcOEt) to afford N-((4aSR*,5SR*,10bSR*)-5-cyclohexyl-3,4,4a,5,6,10b-hexahydro-2H-pyrano[3,2-c]quinolin-9-yl)pentanamide (25 mg, 38%) as yellow solid. The compound was prepared as hydrochloride salt following the method described in example 1.

$^1$H NMR (DMSO) δ ppm: 9.46 (s, 1H), 7.33 (s, 1H), 7.16 (d, J=7.0 Hz, 1H), 6.62 (d, J=8.3 Hz, 1H), 4.39 (d, J=3.3 Hz, 1H), 3.75-3.40 (m, 2H), 3.14-3.01 (m, 1H), 2.21 (t, J=7.4 Hz, 2H), 1.91-1.80 (m, 1H), 1.80-1.38 (m, 12H), 1.38-0.96 (m, 7H), 0.88 (t, J=7.3 Hz, 3H).

EXAMPLE 5

Synthesis of (4aSR*,5SR*,10bSR*)-5-cyclohexyl-N-cyclopropyl-3,4,4a,5,6,10b-hexahydro-2H-pyrano[3,2-c]quinoline-9-carboxamide hydrochloride

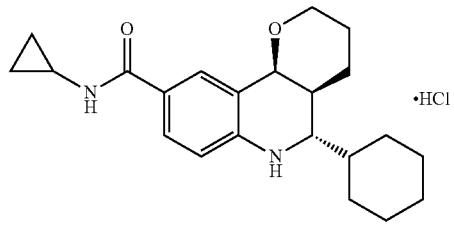 [SMILES: O=C(NC1CC1)c1ccc2c(c1)[C@H]1OCCC[C@H]1[C@H](C1CCCCC1)N2 ; Cl]

Step 1. To (4aSR*,5SR*,10bSR*)-ethyl-5-cyclohexyl-3,4,4a,5,6,10b-hexahydro-2H-pyrano[3,2-c]quinoline-9-carboxylate (Base of example 10, obtained according to example 1 procedure) (145 mg, 0.422 mmol) was added a 0.5 NaOH solution (6 mL, in MeOH/H$_2$O 1:1) and the reaction mixture heated at 65° C. for 24 h. After cooling back to r.t., the reaction mixture was neutralized with 10% HCl solution. The product was extracted with AcOEt twice. The combined organic fractions were dried over Na$_2$SO$_4$ and the solvent removed under reduced pressure after filtration to afford (4aSR*,5SR*,10bSR*)-5-cyclohexyl-3,4,4a,5,6,10b-hexahydro-2H-pyrano[3,2-c]quinoline-9-carboxylic acid (92 mg, 69%).

Step 2. To a stirred solution of (4aSR*,5SR*,10bSR*)-5-cyclohexyl-3,4,4a,5,6,10b-hexahydro-2H-pyrano[3,2-c]quinoline-9-carboxylic acid (50 mg, 0.16 mmol, 1 equiv.) in dry CH$_2$Cl$_2$ (1.6 mL) under argon atmosphere at 0° C. was added cyclopropanamine (12.1 µL, 0.17 mmol, 1.1 equiv.) followed by DIPEA (41 µL, 0.24 mmol, 1.5 equiv.) and EDC (33.5 mg, 0.17 mmol, 1.1 equiv). The reaction mixture was allowed to reach r.t. and stirred overnight. The solvent was removed under reduced pressure and the residue directly purified by Combiflash chromatography (SiO$_2$, c-Hexane/AcOEt) to afford (4aS,5S,10bS)-5-cyclohexyl-3,4,4a,5,6,10b-hexahydro-2H-pyrano[3,2-c]quinoline-9-carboxylic acid (10 mg, 17%). The compound was prepared as hydrochloride salt following the method described in example 1.

$^1$H NMR (CDC$_3$) δ ppm: 7.69-7.49 (m, 2H), 6.73-6.53 (m, 1H), 6.24-6.01 (m, 1H), 4.64-4.47 (m, 1H), 3.92-3.76 (m, 1H), 3.76-3.58 (m, 1H), 3.38-3.22 (m, 1H), 2.99-2.80 (m, 1H), 2.12-1.42 (m, 7H), 1.41-1.00 (m, 8H), 0.96-0.74 (m, 3H), 0.68-0.43 (m, 2H).

EXAMPLE 6

Synthesis of (4aSR*,5RS*,10bSR*)-5-(1-benzylpiperidin-4-yl)-9-(isopentyloxy)-3,4,4a,5,6,10b-hexahydro-2H-pyrano[3,2-c]quinoline hydrochloride

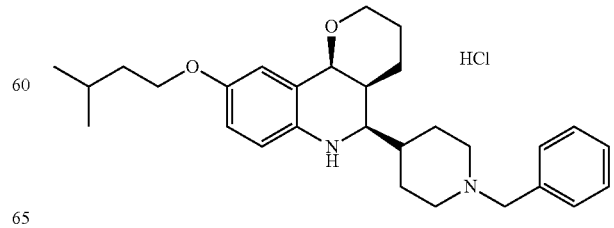

Step 1. To a stirred solution of tert-butyl 4-((4aSR*,5RS*, 10bSR*)-9-(isopentyloxy)-3,4,4a,5,6,10b-hexahydro-2H- pyrano[3,2-c]quinolin-5-yl)piperidine-1-carboxylate (prepared according to the method described in example 1) (400 mg, 0.87 mmol) in dry CH₂Cl₂ (5 mL) under argon atmosphere was added TFA (1 mL) at 0° C. The reaction solution was allowed to reach r.t. and stirred overnight. The reaction was then neutralized with NaOH solution and extracted with CH₂Cl₂ twice. The combined organic fractions were washed with sat. NaCl solution, dried over Na₂SO₄ and concentrated under reduced pressure after filtration giving (4aSR*,5RS*,10bSR*)-9-(isopentyloxy)-5-(piperidin-4-yl)-3,4,4a,5,6,10b-hexahydro-2H-pyrano[3,2-c]quinoline (Base of example 100) (270 mg, 86%) as viscous yellow solid.

Step 2. A Microwave vial was charged with (4aSR*,5RS*,10bSR*)-9-(isopentyloxy)-5-(piperidin-4-yl)-3,4,4a,5,6,10b-hexahydro-2H-pyrano[3,2-c]quinoline (80 mg, 0.22 mmol, 1 equiv.), benzaldehyde (24 mg, 22 µL, 0.22 mmol, 1 equiv.), NaBH(OAc)₃ (95 mg, 0.44 mmol, 2 equiv.) followed by DCE (2.5 mL) under argon atmosphere. This reaction mixture was heated under microwave heating at 90° C. for 10 min. After cooling back to r.t., the reaction mixture was quenched with sat. NaHCO₃ solution and diluted with CH₂Cl₂. The phases were separated and the organic phase additional extracted with CH₂Cl₂ twice. The combined organic phases were dried over MgSO₄ and the solvent removed under reduced pressure after filtration. The residue was purified by Combiflash chromatography (SiO₂, c-Hexane/AcOEt) to afford (4aSR*,5RS*,10bSR*)-5-(1-benzylpiperidin-4-yl)-9-(isopentyloxy)-3,4,4a,5,6,10b-hexahydro-2H-pyrano[3,2-c]quinoline (38 mg, 38%). The compound was prepared as hydrochloride salt following the method described in example 1.

¹H NMR (CDC₃) δ ppm: 7.72-7.57 (m, 2H), 0.94-0.84 (m, 1H), 7.48-7.35 (m, 4H), 7.02 (s, 1H), 6.78 (d, J=8.3 Hz, 1H), 4.93 (d, J=4.0 Hz, 1H), 4.54-4.19 (m, 2H), 3.94 (t, J=6.2 Hz, 2H), 3.90-3.75 (m, 1H), 3.62 (d, J=9.1 Hz, 1H), 3.49-3.06 (m, 2H), 3.21-3.06 (m, 1H), 3.02-2.57 (m, 2H), 2.45-2.26 (m, 2H), 2.11-1.37 (m, 10H), 0.95 (d, J=6.5 Hz, 6H).

EXAMPLE 7

(4aSR*,5RS*,10bSR*)-5-cyclohexyl-3,4,4a,5,6,10b-hexahydro-2H-pyrano[3,2-c]quinolin-10-amine

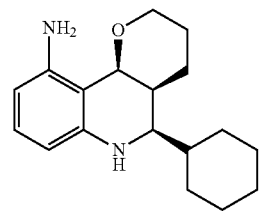 [SMILES: Nc1cccc2c1[C@H]1OCCC[C@H]1[C@@H](C1CCCCC1)N2]

A suspension of (4aSR*,5RS*,10bSR*)-5-cyclohexyl-10-nitro-3,4,4a,5,6,10b-hexahydro-2H-pyrano[3,2-c]quinoline (Example 12, obtained according to example 1 procedure) (90.0 mg, 0.284 mmol) and palladium on activated carbon (10 wt %, 34.5 mg, 0.031 mmol) in EtOH (10 mL) was purged with nitrogen followed by evacuation (three cycles) and then pressurized to 50 psi with hydrogen for 1 day while stirring. After the pressure was released, the reaction mixture was purged with nitrogen. The suspension was filtered over celite and the solvent removed under reduced pressure. The remaining residue was purified by Combiflash chromatography (SiO₂, c-Hexane/AcOEt) to afford (4aSR*,5RS*,10bSR*)-5-cyclohexyl-3,4,4a,5,6,10b-hexahydro-2H-pyrano[3,2-c]quinolin-10-amine (21.4 mg, 26%) as yellow solid.

¹H NMR (CDC₃) δ ppm: 6.83 (dd, J=7.8, 7.9 Hz, 1H), 5.98 (dd, J=7.8, 1.0 Hz, 1H), 5.91 (dd, J=7.9, 1.0 Hz, 1H), 5.15 (d, J=6.0 Hz, 1H), 3.62 (dd, J=10.3, 3.3 Hz, 1H), 3.42 (td, J=9.7, 3.1 Hz, 1H), 2.90 (dd, J=9.7, 1.8 Hz, 1H), 2.27-2.10 (m, 1H), 1.97-1.36 (m, 7H), 1.36-1.07 (m, 4H), 1.03-0.63 (m, 4H).

Examples 8-113 were prepared following the methods described in example 1-7:

| ex. | structure | chemical name | NMR |
|---|---|---|---|
| 8 | 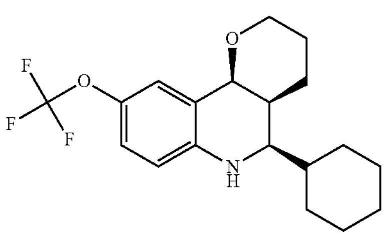 [SMILES: FC(F)(F)Oc1ccc2c(c1)[C@H]1OCCC[C@H]1[C@@H](C1CCCCC1)N2] | (4aSR*,5RS*,10bSR*)-5-cyclohexyl-9-(trifluoromethoxy)-3,4,4a,5,6,10b-hexahydro-2H-pyrano[3,2-c]quinoline | ¹H NMR (CDCl₃) δ ppm: 7.23 (s, 1H), 6.89 (d, J = 8.6 Hz, 1H), 6.45 (d, J = 8.7 Hz, 1H), 4.98 (d, J = 5.5 Hz, 1H), 3.82 (s, 1H), 3.61 (dd, J = 10.8, 3.8 Hz, 1H), 3.38 (t, J = 11.7 Hz, 1H), 2.97 (d, J = 9.5 Hz, 1H), 2.30-2.12 (m, 1H), 1.99-1.56 (m, 7H), 1.50-1.11 (m, 5H), 0.95 (dd, J = 23.6, 11.7 Hz, 2H). |
| 9 | 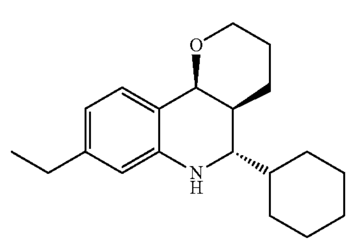 [SMILES: CCc1ccc2c(c1)N[C@@H](C1CCCCC1)[C@@H]1CCCO[C@H]21] | (4aSR*,5SR*,10bSR*)-5-cyclohexyl-8-ethyl-3,4,4a,5,6,10b-hexahydro-2H-pyrano[3,2-c]quinoline | ¹H NMR (CDCl₃) δ ppm: 7.13 (d, J = 7.7 Hz, 1H), 6.52 (dd, J = 7.7, 1.5 Hz, 1H), 6.38 (d, J = 1.3 Hz, 1H), 4.47 (d, J = 3.4 Hz, 1H), 3.98-3.77 (m, 1H), 3.74-3.54 (m, 1H), 3.28 (dd, J = 8.1, 4.9 Hz, 1H), 2.52 (q, J = 7.6 Hz, 2H), 2.04-1.92 (m, 1H), 1.92-1.45 (m, 7H), 1.35-1.00 (m, 5H), 1.19 (t, J = 7.6 Hz, 3H), 0.95-0.78 (m, 1H). |

| ex. | structure | chemical name | NMR |
|---|---|---|---|
| 10 | 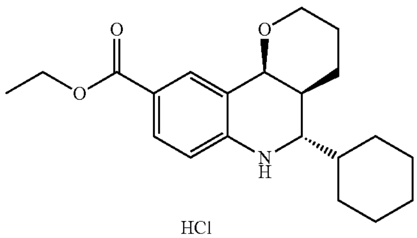 [SMILES: CCOC(=O)c1ccc2c(c1)[C@H]1OCCC[C@H]1[C@H](C1CCCCC1)N2 ; Cl] | (4aSR*,5SR*,10bSR*)-ethyl 5-cyclohexyl-3,4,4a,5,6,10b-hexahydro-2H-pyrano[3,2-c]quinoline-9-carboxylate hydrochloride | $^1$H NMR (CDCl$_3$) δ ppm: 8.01 (d, J = 1.8 Hz, 1H), 7.83 (dd, J = 8.1, 1.4 Hz, 1H), 7.11 (d, J = 8.2 Hz, 1H), 4.57 (d, J = 3.2 Hz, 1H), 4.33 (q, J = 7.2 Hz, 2H), 3.87 (dt, J = 10.0, 3.5 Hz, 1H), 3.75-3.64 (m, 1H), 3.53-3.43 (m, 1H), 2.24-2.13 (m, 1H), 1.99-1.60 (m, 9H), 1.60-1.47 (m, 1H), 1.37 (t, J = 7.1 Hz, 3H), 1.41-1.30 (m, 1H), 1.30-1.11 (m, 4H). |
| 11 | 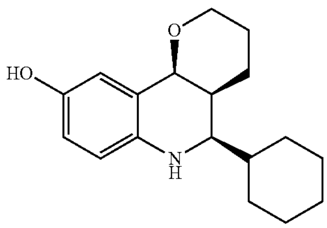 [SMILES: Oc1ccc2c(c1)[C@H]1OCCC[C@H]1[C@@H](C1CCCCC1)N2] | (4aSR*,5RS*,10bSR*)-5-cyclohexyl-3,4,4a,5,6,10b-hexahydro-2H-pyrano[3,2-c]quinolin-9-ol | $^1$H NMR (CDCl$_3$) δ ppm: 6.95 (d, J = 2.3 Hz, 1H), 6.61 (dd, J = 8.4, 2.6 Hz, 1H), 6.44 (d, J = 8.5 Hz, 1H), 5.14-4.79 (m, 1H), 5.01 (d, J = 5.2 Hz, 1H), 3.69-3.57 (m, 1H), 3.56-3.40 (m, 1H), 3.44 (td, J = 12.1, 2.0 Hz, 1H), 2.90 (d, J = 9.5 Hz, 1H), 2.37-2.12 (m, 1H), 1.99-1.65 (m, 7H), 1.57-1.36 (m, 3H), 1.36-1.11 (m, 3H), 1.05-0.74 (m, 2H). |
| 12 | 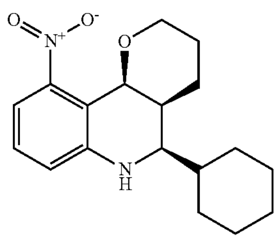 [SMILES: O=[N+]([O-])c1cccc2c1[C@H]1OCCC[C@H]1[C@@H](C1CCCCC1)N2] | (4aSR*,5RS*,10bSR*)-5-cyclohexyl-10-nitro-3,4,4a,5,6,10b-hexahydro-2H-pyrano[3,2-c]quinoline | $^1$H NMR (CDCl$_3$) δ ppm: 7.08 (dd, J = 7.8, 8.2 Hz, 1H), 6.82 (dd, J = 7.8, 0.9 Hz, 1H), 6.61 (dd, J = 8.2, 1.0 Hz, 1H), 5.35 (d, J = 6.2 Hz, 1H), 4.02 (s, 1H), 3.57 (dd, J = 10.9, 3.5 Hz, 1H), 3.11 (td, J = 11.9, 2.2 Hz, 1H), 2.97 (d, J = 10.2 Hz, 1H), 2.32-2.12 (m, 1H), 1.98-1.57 (m, 5H), 1.49-1.36 (m, 3H), 1.36-1.13 (m, 4H), 1.07-0.83 (m, 2H). |
| 13 | 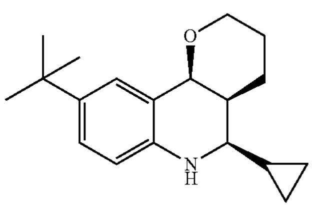 [SMILES: CC(C)(C)c1ccc2c(c1)[C@H]1OCCC[C@H]1[C@@H](C1CC1)N2] | (4aSR*,5RS*,10bSR*)-9-tert-butyl-5-cyclopropyl-3,4,4a,5,6,10b-hexahydro-2H-pyrano[3,2-c]quinoline | $^1$H NMR (CDCl$_3$) δ ppm: 7.20 (s, 1H), 6.89 (d, J = 7.2 Hz, 1H), 6.57-6.26 (m, 1H), 4.74 (d, J = 5.5 Hz, 1H), 3.44-3.34 (m, 1H), 3.20 (td, J = 11.7, 2.1 Hz, 1H), 2.21 (d, J = 9.0 Hz, 1H), 2.07-1.93 (m, 1H), 1.72-1.59 (m, 1H), 1.43-1.23 (m, 3H), 1.05 (s, 9H), 0.98-0.82 (m, 1H), 0.47-0.29 (m, 2H), 0.06-−0.05 (m, 1H). |
| 14 | 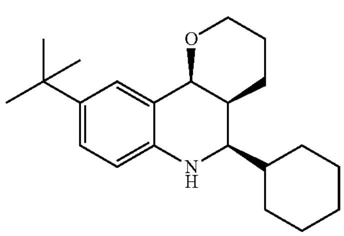 [SMILES: CC(C)(C)c1ccc2c(c1)[C@H]1OCCC[C@H]1[C@@H](C1CCCCC1)N2] | (4aSR*,5RS*,10bSR*)-9-tert-butyl-5-cyclohexyl-3,4,4a,5,6,10b-hexahydro-2H-pyrano[3,2-c]quinoline | $^1$H NMR (CDCl$_3$) δ ppm: 7.40 (d, J = 2.2 Hz, 1H), 7.07 (dd, J = 8.4, 2.4 Hz, 1H), 6.46 (d, J = 8.3 Hz, 1H), 5.03 (d, J = 5.5 Hz, 1H), 3.68 (s, 1H), 3.60 (dd, J = 11.3, 4.7 Hz, 1H), 3.42 (td, J = 11.9, 2.0 Hz, 1H), 2.95 (dd, J = 9.6, 1.9 Hz, 1H), 2.33-2.14 (m, 1H), 2.00-1.58 (m, 7H), 1.52-1.38 (m, 3H), 1.28 (s, 9H), 1.37-1.07 (m, 4H), 1.05-0.77 (m, 2H). |
| 15 | 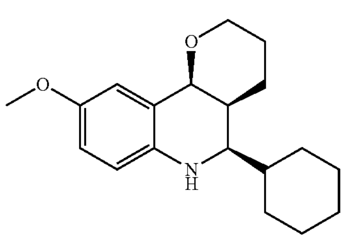 [SMILES: COc1ccc2c(c1)[C@H]1OCCC[C@H]1[C@@H](C1CCCCC1)N2] | (4aSR*,5RS*,10bSR*)-5-cyclohexyl-9-methoxy-3,4,4a,5,6,10b-hexahydro-2H-pyrano[3,2-c]quinoline | $^1$H NMR (CDCl$_3$) δ ppm: 6.97 (d, J = 2.7 Hz, 1H), 6.67 (dd, J = 8.6, 2.9 Hz, 1H), 6.48 (d, J = 8.7 Hz, 1H), 5.00 (d, J = 5.6 Hz, 1H), 3.75 (s, 3H), 3.60 (dd, J = 11.3, 4.5 Hz, 1H), 3.53 (s, 1H), 3.43 (td, J = 12.0, 2.1 Hz, 1H), 2.91 (dd, J = 9.6, 1.8 Hz, 1H), 2.32-2.10 (m, 1H), 1.98-1.56 (m, 7H), 1.52-1.34 (m, 3H), 1.34-1.09 (m, 3H), 1.07-0.77 (m, 2H). |

| ex. | structure | chemical name | NMR |
|---|---|---|---|
| 16 | 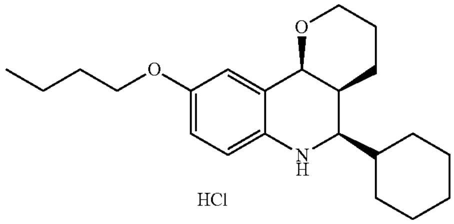 [SMILES: CCCCOc1ccc2c(c1)[C@H]1OCCC[C@H]1[C@@H](C1CCCCC1)N2 ; Cl] | (4aSR*,5RS*,10bSR*)-9-butoxy-5-cyclohexyl-3,4,4a,5,6,10b-hexahydro-2H-pyrano[3,2-c]quinoline hydrochloride | $^1$H NMR (CDCl$_3$) δ ppm: 7.97 (d, J = 7.7 Hz, 1H), 7.07 (d, J = 2.0 Hz, 1H), 6.85 (dd, J = 7.7, 2.0 Hz, 1H), 4.89 (d, J = 5.1 Hz, 1H), 3.96 (t, J = 6.5 Hz, 2H), 3.65 (d, J = 11.0 Hz, 1H), 3.35 (t, J = 10.9 Hz, 1H), 3.21 (d, J = 8.9 Hz, 1H), 2.74-2.62 (m, 1H), 2.58-2.43 (m, 1H), 2.36-2.13 (m, 1H), 1.97-1.14 (m, 17H), 1.13-0.97 (m, 1H), 0.98 (t, J = 7.4 Hz, 3H). |
| 17 | 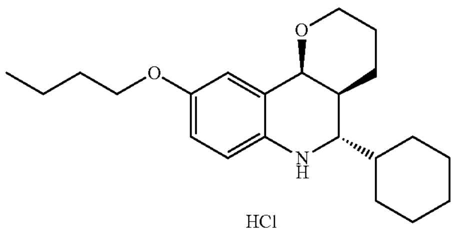 [SMILES: CCCCOc1ccc2c(c1)[C@H]1OCCC[C@H]1[C@H](C1CCCCC1)N2 ; Cl] | (4aSR*,5RS*,10bSR*)-9-butoxy-5-cyclohexyl-3,4,4a,5,6,10b-hexahydro-2H-pyrano[3,2-c]quinoline hydrochloride | $^1$H NMR (CDCl$_3$) δ ppm: 8.08 (d, J = 8.9 Hz, 1H), 6.95 (d, J = 2.7 Hz, 1H), 6.81 (dd, J = 8.9, 2.8 Hz, 1H), 4.61 (d, J = 3.5 Hz, 1H), 3.95 (t, J = 6.4 Hz, 2H), 3.90-3.76 (m, 1H), 3.72-3.55 (m, 2H), 2.60-2.41 (m, 1H), 2.09-1.94 (m, 2H), 1.98-1.62 (m, 10H), 1.65-1.37 (m, 4H), 1.37-1.13 (m, 3H), 0.98 (t, J = 7.4 Hz, 3H). |
| 18 | 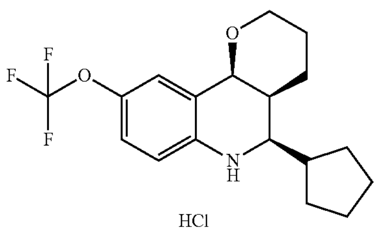 [SMILES: FC(F)(F)Oc1ccc2c(c1)[C@H]1OCCC[C@H]1[C@@H](C1CCCC1)N2 ; Cl] | (4aSR*,5RS*,10bSR*)-5-cyclopentyl-9-(trifluoromethoxy)-3,4,4a,5,6,10b-hexahydro-2H-pyrano[3,2-c]quinoline hydrochloride | $^1$H NMR (CDCl$_3$) δ ppm: 7.84-7.70 (m, 1H), 7.43 (s, 1H), 7.17-7.04 (m, 1H), 4.97 (d, J = 4.7 Hz, 1H), 3.68 (dd, J = 11.5, 2.9 Hz, 1H), 3.38-3.22 (m, 2H), 2.61-2.27 (m, 3H), 1.97-1.41 (m, 11H). |
| 19 | 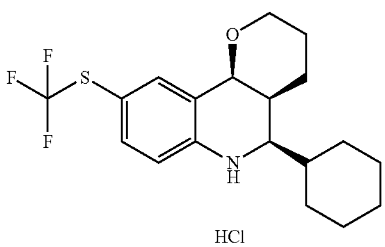 [SMILES: FC(F)(F)Sc1ccc2c(c1)[C@H]1OCCC[C@H]1[C@@H](C1CCCCC1)N2 ; Cl] | (4aSR*,5RS*,10bSR*)-5-cyclohexyl-9-(trifluoromethylthio)-3,4,4a,5,6,10b-hexahydro-2H-pyrano[3,2-c]quinoline hydrochloride | $^1$H NMR (CDCl$_3$) δ ppm: 7.61 (s, 1H), 7.27 (dd, J = 8.4, 2.0 Hz, 1H), 6.46 (d, J = 8.4 Hz, 1H), 4.99 (d, J = 5.5 Hz, 1H), 4.07 (s, 1H), 3.61 (dd, J = 11.4, 4.6 Hz, 1H), 3.39 (td, J = 11.9, 2.3 Hz, 1H), 3.02 (dd, J = 9.7, 2.1 Hz, 1H), 2.30-2.14 (m, 1H), 1.96-1.56 (m, 7H), 1.53-1.13 (m, 6H), 1.10-0.80 (m, 2H). |
| 20 | 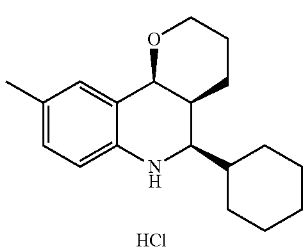 [SMILES: Cc1ccc2c(c1)[C@H]1OCCC[C@H]1[C@@H](C1CCCCC1)N2 ; Cl] | (4aSR*,5RS*,10bSR*)-5-cyclohexyl-9-methyl-3,4,4a,5,6,10b-hexahydro-2H-pyrano[3,2-c]quinoline hydrochloride | $^1$H NMR (CDCl$_3$) δ ppm: 7.91 (d, J = 7.8 Hz, 1H), 7.39 (s, 1H), 7.11 (d, J = 8.0 Hz, 1H), 4.91 (d, J = 4.1 Hz, 1H), 3.64 (d, J = 12.8 Hz, 1H), 3.33 (t, J = 11.6 Hz, 1H), 3.21 (d, J = 9.7 Hz, 1H), 2.77-2.63 (m, 1H), 2.62-2.47 (m, 1H), 2.36 (s, 3H), 2.32-2.20 (m, 1H), 2.17 (s, 1H), 1.97-0.95 (m, 8H). |
| 21 | 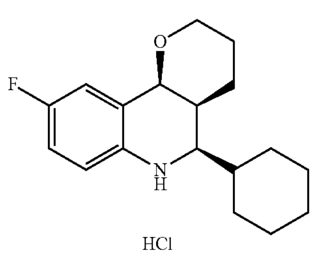 [SMILES: Fc1ccc2c(c1)[C@H]1OCCC[C@H]1[C@@H](C1CCCCC1)N2 ; Cl] | (4aSR*,5RS*,10bSR*)-5-cyclohexyl-9-fluoro-3,4,4a,5,6,10b-hexahydro-2H-pyrano[3,2-c]quinoline hydrochloride | $^1$H NMR (CDCl$_3$) δ ppm: 7.12 (dd, J = 9.2, 1.6 Hz, 1H), 6.86-6.57 (m, 2H), 4.96 (d, J = 5.5 Hz, 1H), 3.67-3.57 (m, 1H), 3.38 (td, J = 11.8, 2.0 Hz, 1H), 2.98 (d, J = 9.1 Hz, 1H), 2.33-2.21 (m, 1H), 2.12-1.94 (m, 1H), 1.91-1.75 (m, 3H), 1.75-1.10 (m, 9H), 1.10-0.80 (m, 2H). |

| ex. | structure | chemical name | NMR |
|---|---|---|---|
| 22 | 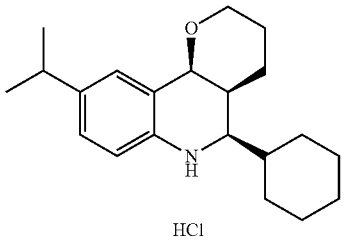 [SMILES: CC(C)c1ccc2c(c1)[C@H]1OCCC[C@H]1[C@@H](C1CCCCC1)N2 ; Cl] | (4aSR*,5RS*, 10bSR*)-5-cyclohexyl-9-isopropyl-3,4,4a,5,6,10b-hexahydro-2H-pyrano[3,2-c]quinoline hydrochloride | $^1$H NMR (CDCl$_3$) δ ppm: 7.99 (d, J = 6.8 Hz, 1H), 7.44 (s, 1H), 7.17 (d, J = 6.8 Hz, 1H), 4.92 (d, J = 5.0 Hz, 1H), 3.65 (d, J = 10.4 Hz, 1H), 3.40-3.20 (m, 2H), 2.93 (q, J = 13.6, 6.7 Hz, 1H), 2.77-2.61 (m, 1H), 2.61-2.47 (m, 1H), 2.38-2.20 (m, 1H), 1.99-1.48 (m, 8H), 1.50-1.18 (m, 4H), 1.24 (d, J = 6.8 Hz, 6H), 1.14-0.92 (m, 1H). |
| 23 | 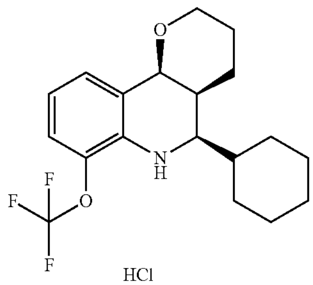 [SMILES: FC(F)(F)Oc1cccc2c1N[C@H](C1CCCCC1)[C@@H]1CCCO[C@H]21 ; Cl] | (4aSR*,5RS*, 10bSR*)-5-cyclohexyl-7-(trifluoromethoxy)-3,4,4a,5,6,10b-hexahydro-2H-pyrano[3,2-c]quinoline hydrochloride | $^1$H NMR (CDCl$_3$) δ ppm: 7.28 (d, J = 7.9 Hz, 1H), 7.00 (d, J = 8.1 Hz, 1H), 6.65 (t, J = 7.9 Hz, 1H), 5.02 (d, J = 5.6 Hz, 1H), 4.17 (s, 1H), 3.64-3.55 (m, 1H), 3.39 (td, J = 12.1, 2.2 Hz, 1H), 2.99 (dd, J = 9.7, 1.6 Hz, 1H), 2.29-2.15 (m, 1H), 1.99-1.56 (m, 8H), 1.52-1.10 (m, 5H), 1.08-0.84 (m, 2H). |
| 24 | 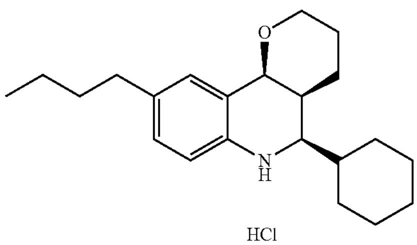 [SMILES: CCCCc1ccc2c(c1)[C@H]1OCCC[C@H]1[C@@H](C1CCCCC1)N2 ; Cl] | (4aSR*,5RS*, 10bSR*)-9-butyl-5-cyclohexyl-3,4,4a,5,6,10b-hexahydro-2H-pyrano[3,2-c]quinoline hydrochloride | $^1$H NMR (CDCl$_3$) δ ppm: 7.90 (d, J = 6.8 Hz, 1H), 7.38 (s, 1H), 7.10 (d, J = 6.4 Hz, 1H), 4.92 (d, J = 5.0 Hz, 1H), 3.64 (d, J = 9.9 Hz, 1H), 3.32 (t, J = 11.0 Hz, 1H), 3.22 (d, J = 9.0 Hz, 1H), 2.78-2.57 (m, 1H), 2.61 (t, J = 7.7 Hz, 2H), 2.57-2.42 (m, 1H), 2.25 (dd, J = 13.5, 6.5 Hz, 1H), 2.01-1.46 (m, 10H), 1.46-1.14 (m, 8H), 1.12-0.92 (m, 2H), 0.93 (t, J = 7.3 Hz, 3H). |
| 25 | 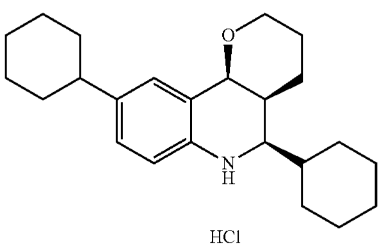 [SMILES: c1cc2c(cc1C1CCCCC1)[C@H]1OCCC[C@H]1[C@@H](C1CCCCC1)N2 ; Cl] | (4aSR*,5RS*, 10bSR*)-5,9-dicyclohexyl-3,4,4a,5,6,10b-hexahydro-2H-pyrano[3,2-c]quinoline hydrochloride | $^1$H NMR (CDCl$_3$) δ ppm: 7.92 (d, J = 7.1 Hz, 1H), 7.41 (s, 1H), 7.13 (d, J = 7.2 Hz, 1H), 4.92 (d, J = 5.1 Hz, 1H), 3.65 (d, J = 10.8 Hz, 1H), 3.32 (t, J = 10.9 Hz, 1H), 3.24 (d, J = 9.4 Hz, 1H), 2.75-2.59 (m, 1H), 2.60-2.41 (m, 2H), 2.35-2.14 (m, 1H), 2.02-1.49 (m, 12H), 1.48-0.85 (m, 10H), 1.12-0.89 (m, 1H). |
| 26 | 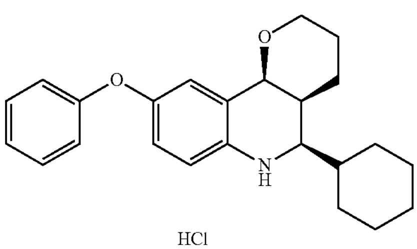 [SMILES: c1ccc(Oc2ccc3c(c2)[C@H]2OCCC[C@H]2[C@@H](C2CCCCC2)N3)cc1 ; Cl] | (4aSR*,5RS*, 10bSR*)-5-cyclohexyl-9-phenoxy-3,4,4a,5,6,10b-hexahydro-2H-pyrano[3,2-c]quinoline hydrochloride | $^1$H NMR (CDCl$_3$) δ ppm: 7.99 (d, J = 8.8 Hz, 1H), 7.34 (t, J = 7.9 Hz, 2H), 7.19 (d, J = 2.0 Hz, 1H), 7.13 (t, J = 7.4 Hz, 1H), 6.99 (d, J = 7.7 Hz, 2H), 6.90 (dd, J = 8.6, 2.5 Hz, 1H), 4.87 (d, J = 5.1 Hz, 1H), 3.60 (d, J = 10.4 Hz, 1H), 3.39-3.17 (m, 2H), 2.71-2.57 (m, 1H), 2.57-2.47 (m, 1H), 2.32-2.16 (m, 1H), 1.96-1.73 (m, 5H), 1.72-1.46 (m, 3H), 1.44-1.11 (m, 5H), 1.11-0.90 (m, 1H). |
| 27 | 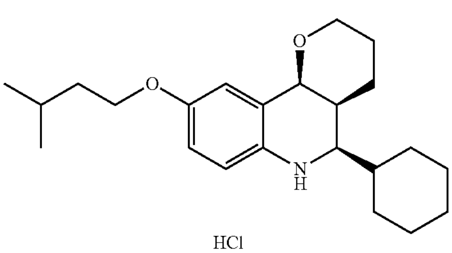 [SMILES: CC(C)CCOc1ccc2c(c1)[C@H]1OCCC[C@H]1[C@@H](C1CCCCC1)N2 ; Cl] | (4aSR*,5RS*, 10bSR*)-5-cyclohexyl-9-(isopentyloxy)-3,4,4a,5,6,10b-hexahydro-2H-pyrano[3,2-c]quinoline hydrochloride | $^1$H NMR (CDCl$_3$) δ ppm: 7.89 (d, J = 8.1 Hz, 1H), 7.06 (s, 1H), 6.84 (d, J = 8.5 Hz, 1H), 4.89 (d, J = 5.1 Hz, 1H), 3.98 (t, J = 6.5 Hz, 2H), 3.65 (d, J = 10.9 Hz, 1H), 3.35 (t, J = 11.2 Hz, 1H), 3.20 (d, J = 8.4 Hz, 1H), 2.73-2.57 (m, 1H), 2.58-2.41 (m, 1H), 2.32-2.13 (m, 1H), 1.98-1.46 (m, 11H), 1.30 (dd, J = 26.7, 12.6 Hz, 5H), 1.13-0.96 (m, 1H), 0.96 (d, J = 6.6 Hz, 6H). |

-continued

| ex. | structure | chemical name | NMR |
|---|---|---|---|
| 28 | 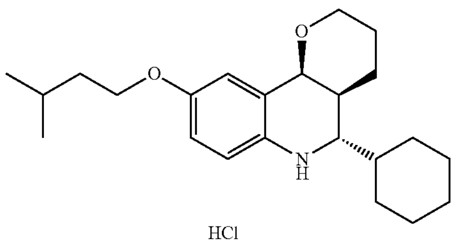 [SMILES: CC(C)CCOc1ccc2c(c1)[C@H]1OCCC[C@H]1[C@H](C1CCCCC1)N2 ; Cl] | (4aSR*,10bSR*)-5-cyclohexyl-9-(isopentyloxy)-3,4,4a,5,6,10b-hexahydro-2H-pyrano[3,2-c]quinoline hydrochloride | $^1$H NMR (CDCl$_3$) δ ppm: 8.02 (d, J = 8.1 Hz, 1H), 6.94 (d, J = 2.6 Hz, 1H), 6.81 (dd, J = 8.5, 2.3 Hz, 1H), 4.60 (d, J = 3.2 Hz, 1H), 3.98 (t, J = 6.5 Hz, 2H), 3.85 (dt, J = 7.7, 3.5 Hz, 1H), 3.73-3.57 (m, 2H), 2.59-2.45 (m, 1H), 2.07-1.93 (m, 2H), 1.93-1.39 (m, 12H), 1.39-1.12 (m, 4H), 0.96 (d, J = 6.6 Hz, 6H). |
| 29 | 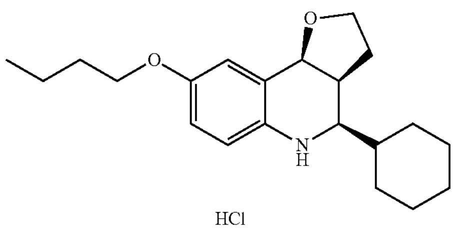 [SMILES: CCCCOc1ccc2c(c1)[C@H]1OCC[C@H]1[C@@H](C1CCCCC1)N2 ; Cl] | (3aSR*,4RS*,9bSR*)-8-butoxy-4-cyclohexyl-2,3,3a,4,5,9b-hexahydrofuro[3,2-c]quinoline hydrochloride | $^1$H NMR (CDCl$_3$) δ ppm: 8.01 (d, J = 8.0 Hz, 1H), 6.98 (d, J = 2.2 Hz, 1H), 6.83 (dd, J = 8.4, 1.8 Hz, 1H), 5.05 (d, J = 7.7 Hz, 1H), 4.02-3.82 (m, 3H), 3.82-3.70 (m, 1H), 3.47 (d, J = 6.1 Hz, 1H), 3.02-2.83 (m, 1H), 2.58-2.46 (m, 1H), 2.48-2.31 (m, 1H), 2.30-2.16 (m, 1H), 2.18-2.01 (m, 2H), 1.94-1.05 (m, 12H), 0.98 (t, J = 7.4 Hz, 3H). |
| 30 | 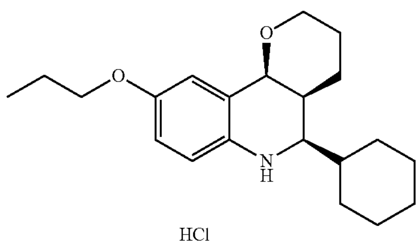 [SMILES: CCCOc1ccc2c(c1)[C@H]1OCCC[C@H]1[C@@H](C1CCCCC1)N2 ; Cl] | (4aSR*,5RS*,10bSR*)-5-cyclohexyl-9-propoxy-3,4,4a,5,6,10b-hexahydro-2H-pyrano[3,2-c]quinoline hydrochloride | $^1$H NMR (CDCl$_3$) δ ppm: 7.91 (d, J = 8.1 Hz, 1H), 7.07 (s, 1H), 6.85 (d, J = 8.5 Hz, 1H), 4.89 (d, J = 4.1 Hz, 1H), 3.91 (t, J = 6.5 Hz, 2H), 3.65 (d, J = 10.4 Hz, 1H), 3.35 (t, J = 11.0 Hz, 1H), 3.21 (d, J = 6.5 Hz, 1H), 2.72-2.57 (m, 1H), 2.58-2.43 (m, 1H), 2.33-2.18 (m, 1H), 1.97-1.46 (m, 10H), 1.47-1.13 (m, 4H), 1.04 (t, J = 7.4 Hz, 3H), 1.04 (t, J = 7.4 Hz, 1H). |
| 31 | 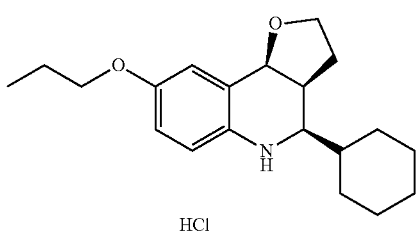 [SMILES: CCCOc1ccc2c(c1)[C@H]1OCC[C@H]1[C@@H](C1CCCCC1)N2 ; Cl] | (3aSR*,4RS*,9bSR*)-4-cyclohexyl-8-propoxy-2,3,3a,4,5,9b-hexahydrofuro[3,2-c]quinoline hydrochloride | $^1$H NMR (CDCl$_3$) δ ppm: 7.98 (d, J = 8.0 Hz, 1H), 6.98 (s, 1H), 6.83 (d, J = 8.3 Hz, 1H), 5.06 (d, J = 7.3 Hz, 1H), 4.02-3.83 (m, 3H), 3.83-3.70 (m, 1H), 3.59-3.33 (m, 1H), 3.02-2.83 (m, 1H), 2.66-2.50 (m, 1H), 2.50-2.33 (m, 1H), 2.32-2.02 (m, 3H), 1.96-1.68 (m, 5H), 1.56-1.09 (m, 5H), 1.03 (t, J = 7.3 Hz, 3H). |
| 32 | 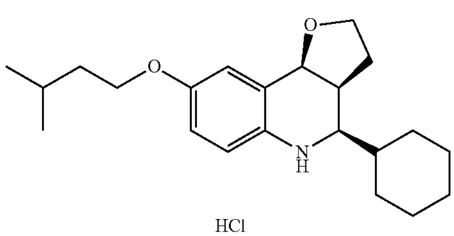 [SMILES: CC(C)CCOc1ccc2c(c1)[C@H]1OCC[C@H]1[C@@H](C1CCCCC1)N2 ; Cl] | (3aSR*,4RS*,9bSR*)-4-cyclohexyl-8-(isopentyloxy)-2,3,3a,4,5,9b-hexahydrofuro[3,2-c]quinoline hydrochloride | $^1$H NMR (CDCl$_3$) δ ppm: 7.92 (d, J = 8.5 Hz, 1H), 6.98 (d, J = 2.6 Hz, 1H), 6.82 (dd, J = 8.5, 2.3 Hz, 1H), 5.05 (d, J = 7.5 Hz, 1H), 4.03-3.92 (m, 2H), 3.92-3.81 (m, 1H), 3.81-3.72 (m, 1H), 3.46 (d, J = 6.4 Hz, 1H), 3.00-2.78 (m, 1H), 2.58-2.41 (m, 1H), 2.41-2.26 (m, 1H), 2.25-2.14 (m, 1H), 2.14-1.98 (m, 2H), 1.92-1.48 (m, 8H), 1.49-1.05 (m, 5H), 0.95 (d, J = 6.6 Hz, 6H). |
| 33 | 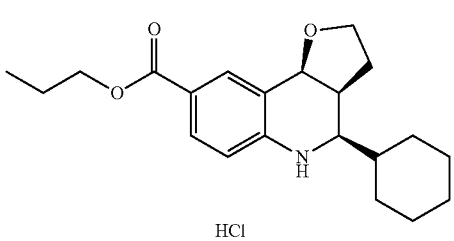 [SMILES: CCCOC(=O)c1ccc2c(c1)[C@H]1OCC[C@H]1[C@@H](C1CCCCC1)N2 ; Cl] | (3aSR*,4RS*,9bSR*)-propyl 4-cyclohexyl-2,3,3a,4,5,9b-hexahydrofuro[3,2-c]quinoline-8-carboxylate hydrochloride | $^1$H NMR (CDCl$_3$) δ ppm: 8.01 (d, J = 1.2 Hz, 1H), 7.72 (dd, J = 8.5, 1.9 Hz, 1H), 6.47 (d, J = 8.5 Hz, 1H), 5.10 (d, J = 7.7 Hz, 1H), 4.26-4.15 (m, 2H), 4.13 (s, 1H), 3.88-3.63 (m, 2H), 3.21 (dd, J = 9.1, 2.6 Hz, 1H), 2.81-2.62 (m, 1H), 2.04-1.63 (m, 9H), 1.49-1.14 (m, 4H), 1.12-0.96 (m, 2H), 1.00 (t, J = 7.4 Hz, 3H). |

| ex. | structure | chemical name | NMR |
|---|---|---|---|
| 34 | 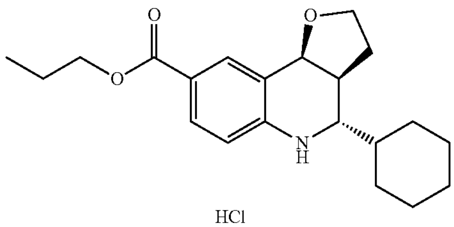 [SMILES: CCCOC(=O)c1ccc2c(c1)[C@H]1OCC[C@H]1[C@H](C1CCCCC1)N2 ; Cl] | (3aSR*,4SR*,9bSR*)-propyl 4-cyclohexyl-2,3,3a,4,5,9b-hexahydrofuro[3,2-c]quinoline-8-carboxylate hydrochloride | $^1$H NMR (CDCl$_3$) δ ppm: 8.11 (s, 1H), 7.81 (d, J = 7.9 Hz, 1H), 7.05 (d, J = 7.9 Hz, 1H), 4.78 (d, J = 5.5 Hz, 1H), 4.23 (t, J = 6.7 Hz, 2H), 4.03-3.89 (m, 1H), 3.83 (dd, J = 15.5, 7.8 Hz, 1H), 2.90-2.77 (m, 1H), 2.77-2.54 (m, 1H), 2.32-2.06 (m, 1H), 1.93-1.53 (m, 8H), 1.50-1.08 (m, 6H), 1.01 (t, J = 7.4 Hz, 3H), 1.07-0.88 (m, 1H). |
| 35 | 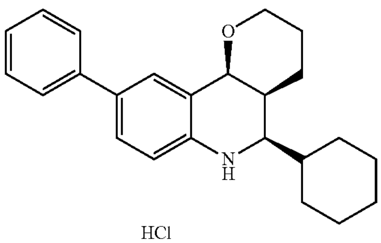 [SMILES: c1ccc(-c2ccc3c(c2)[C@H]2OCCC[C@H]2[C@@H](C2CCCCC2)N3)cc1 ; Cl] | (4aSR*,5RS*,10bSR*)-5-cyclohexyl-9-phenyl-3,4,4a,5,6,10b-hexahydro-2H-pyrano[3,2-c]quinoline hydrochloride | $^1$H NMR (CDCl$_3$) δ ppm: 8.14-7.95 (m, 1H), 7.80 (s, 1H), 7.58-7.48 (m, 3H), 7.48-7.32 (m, 3H), 5.01 (d, J = 4.5 Hz, 1H), 3.65 (d, J = 9.8 Hz, 1H), 3.47-3.21 (m, 2H), 2.75-2.48 (m, 2H), 2.37-2.10 (m, 1H), 1.99-1.49 (m, 9H), 1.47-1.14 (m, 4H), 1.14-0.92 (m, 1H). |
| 36 | 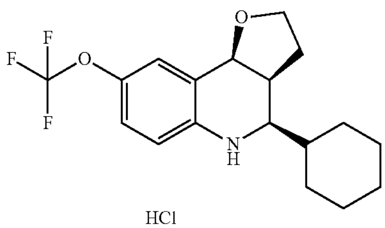 [SMILES: FC(F)(F)Oc1ccc2c(c1)[C@H]1OCC[C@H]1[C@@H](C1CCCCC1)N2 ; Cl] | (3aSR*,4RS*,9bSR*)-4-cyclohexyl-8-(trifluoromethoxy)-2,3,3a,4,5,9b-hexahydrofuro[3,2-c]quinoline hydrochloride | $^1$H NMR (CDCl$_3$) δ ppm: 7.22 (s, 1H), 7.14-6.70 (m, 2H), 5.06 (d, J = 7.8 Hz, 1H), 3.94-3.69 (m, 2H), 3.23 (d, J = 7.5 Hz, 1H), 2.78 (q, J = 8.2 Hz, 1H), 2.14-1.47 (m, 7H), 1.48-0.85 (m, 5H). |
| 37 | 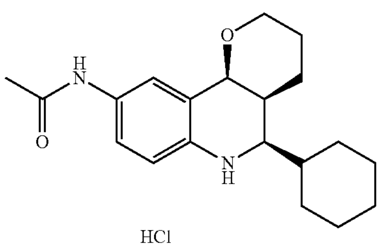 [SMILES: CC(=O)Nc1ccc2c(c1)[C@H]1OCCC[C@H]1[C@@H](C1CCCCC1)N2 ; Cl] | N-((4aSR*,5RS*,10bSR*)-5-cyclohexyl-3,4,4a,5,6,10b-hexahydro-2H-pyrano[3,2-c]quinolin-9-yl)acetamide hydrochloride | $^1$H NMR (DMSO) δ ppm: 9.80 (s, 1H), 7.49 (s, 1H), 7.39 (d, J = 8.6 Hz, 1H), 6.89 (d, J = 8.1 Hz, 1H), 4.92 (d, J = 5.0 Hz, 1H), 3.52 (d, J = 10.7 Hz, 1H), 3.20 (t, J = 10.8 Hz, 1H), 3.08 (d, J = 8.5 Hz, 1H), 2.25-2.04 (m, 1H), 1.99 (s, 3H), 1.86-1.68 (m, 3H), 1.69-1.38 (m, 6H), 1.32-1.06 (m, 4H), 1.05-0.82 (m, 2H). |
| 38 | 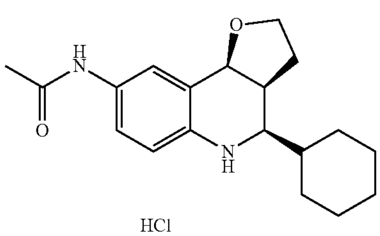 [SMILES: CC(=O)Nc1ccc2c(c1)[C@H]1OCC[C@H]1[C@@H](C1CCCCC1)N2 ; Cl] | N-((3aSR*,4RS*,9bSR*)-4-cyclohexyl-2,3,3a,4,5,9b-hexahydrofuro[3,2-c]quinolin-8-yl)acetamide hydrochloride | $^1$H NMR (DMSO) δ ppm: 9.84 (s, 1H), 7.50 (s, 1H), 7.35 (d, J = 8.1 Hz, 1H), 6.95 (d, J = 7.9 Hz, 1H), 4.99 (d, J = 7.7 Hz, 1H), 3.71 (q, J = 7.8 Hz, 1H), 3.53 (td, J = 8.2, 4.6 Hz, 1H), 3.26 (d, J = 7.4 Hz, 1H), 2.80-2.57 (m, 1H), 2.20-2.03 (m, 1H), 1.99 (s, 3H), 1.95-1.82 (m, 3H), 1.82-1.71 (m, 2H), 1.71-1.60 (m, 1H), 1.60-1.47 (m, 1H), 1.34-1.11 (m, 3H), 1.11-0.88 (m, 2H). |
| 39 | 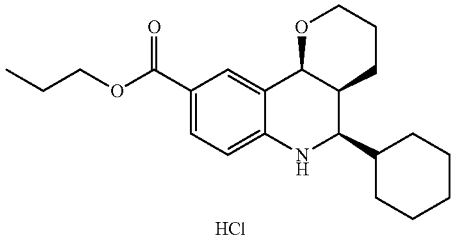 [SMILES: CCCOC(=O)c1ccc2c(c1)[C@H]1OCCC[C@H]1[C@@H](C1CCCCC1)N2 ; Cl] | (4aSR*,5RS*,10bSR*)-propyl 5-cyclohexyl-3,4,4a,5,6,10b-hexahydro-2H-pyrano[3,2-c]quinoline-9-carboxylate hydrochloride | $^1$H NMR (DMSO) δ ppm: 8.05 (s, 1H), 7.73 (dd, J = 8.4, 1.6 Hz, 1H), 6.45 (d, J = 8.5 Hz, 1H), 5.30 (s, 1H), 5.00 (d, J = 5.3 Hz, 1H), 4.32-4.08 (m, 3H), 3.63 (dd, J = 11.7, 4.8 Hz, 1H), 3.43 (td, J = 12.2, 2.3 Hz, 1H), 3.04 (dd, J = 10.0, 2.1 Hz, 1H), 2.33-2.13 (m, 1H), 2.00-1.64 (m, 7H), 1.64-1.38 (m, 2H), 1.36-1.11 (m, 5H), 1.01 (t, J = 7.4 Hz, 3H), 1.11-0.74 (m, 3H). |

| ex. | structure | chemical name | NMR |
|---|---|---|---|
| 40 | 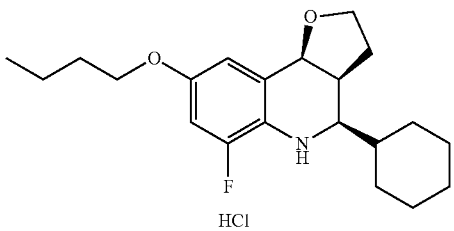 [SMILES: CCCCOc1cc(F)c2c(c1)[C@H]1OCC[C@H]1[C@@H](C1CCCCC1)N2 ; Cl] | (3aSR*,4RS*, 9bSR*)-8-butoxy-4-cyclohexyl-6-fluoro-2,3,3a,4,5,9b-hexahydrofuro[3,2-c]quinoline hydrochloride | $^1$H NMR (CDCl$_3$) δ ppm: 6.74 (s, 1H), 6.61 (d, J = 11.0 Hz, 1H), 5.01 (d, J = 7.3 Hz, 1H), 4.01-3.80 (m, 3H), 3.80-3.67 (m, 1H), 3.38 (d, J = 6.7 Hz, 1H), 2.89-2.74 (m, 1H), 2.31-2.08 (m, 2H), 1.80 (ddd, J = 30.5, 20.9, 20.2 Hz, 8H), 1.54-1.01 (m, 7H), 0.97 (t, J = 7.3 Hz, 3H). |
| 41 | 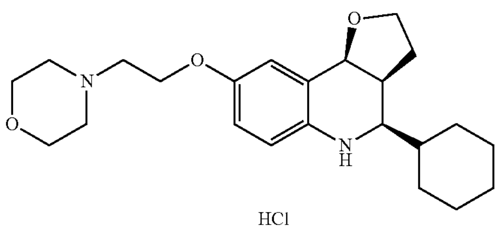 [SMILES: c1cc2c(cc1OCCN1CCOCC1)[C@H]1OCC[C@H]1[C@@H](C1CCCCC1)N2 ; Cl] | (3aSR*,4RS*, 9bSR*)-4-cyclohexyl-8-(2-morpholino-ethoxy)-2,3,3a,4,5,9b-hexahydrofuro[3,2-c]quinoline hydrochloride | $^1$H NMR (CDCl$_3$) δ ppm: 6.84 (d, J = 2.6 Hz, 1H), 6.66 (dd, J = 8.7, 2.7 Hz, 1H), 6.49 (d, J = 8.6 Hz, 1H), 5.04 (d, J = 7.9 Hz, 1H), 4.55-4.39 (m, 2H), 4.30 (t, J = 12.1 Hz, 2H), 3.98 (d, J = 11.1 Hz, 2H), 3.87-3.68 (m, 2H), 3.64-3.42 (m, 2H), 3.45-3.28 (m, 2H), 3.22-2.94 (m, 3H), 2.81-2.64 (m, 1H), 2.10-1.66 (m, 7H), 1.50-1.09 (m, 4H), 1.10-0.87 (m, 2H). |
| 42 | 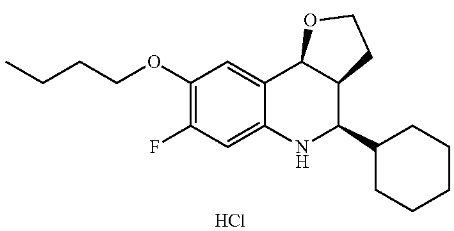 [SMILES: CCCCOc1cc2c(cc1F)N[C@H](C1CCCCC1)[C@@H]1CCO[C@H]21 ; Cl] | (3aSR*,4RS*, 9bSR*)-8-butoxy-4-cyclohexyl-7-fluoro-2,3,3a,4,5,9b-hexahydrofuro[3,2-c]quinoline hydrochloride | $^1$H NMR (CDCl$_3$) δ ppm: 8.02 (d, J = 11.0 Hz, 1H), 7.05 (d, J = 8.5 Hz, 1H), 5.03 (d, J = 7.6 Hz, 1H), 4.13-3.95 (m, 2H), 3.93-3.70 (m, 2H), 3.49 (dd, J = 8.0, 2.3 Hz, 1H), 2.94 (q, J = 7.6 Hz, 1H), 2.66-2.51 (m, 1H), 2.51-2.31 (m, 1H), 2.32-2.00 (m, 3H), 1.97-1.62 (m, 5H), 1.60-1.05 (m, 7H), 0.98 (t, J = 7.4 Hz, 3H). |
| 43 | 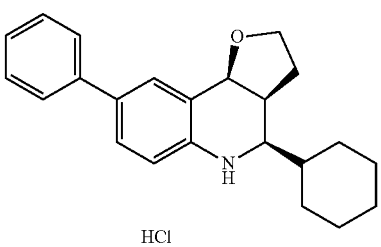 [SMILES: c1ccc(-c2ccc3c(c2)[C@H]2OCC[C@H]2[C@@H](C2CCCCC2)N3)cc1 ; Cl] | (3aSR*,4RS*, 9bSR*)-4-cyclohexyl-8-phenyl-2,3,3a,4,5,9b-hexahydrofuro[3,2-c]quinoline hydrochloride | $^1$H NMR (DMSO) δ ppm: 7.52 (d, J = 7.2 Hz, 2H), 7.42-7.34 (m, 3H), 7.29 (dd, J = 8.4, 2.2 Hz, 1H), 7.22 (t, J = 7.3 Hz, 1H), 6.84 (d, J = 8.4 Hz, 1H), 5.06 (d, J = 7.8 Hz, 1H), 3.70 (q, J = 7.9 Hz, 1H), 3.64-3.50 (m, 1H), 3.13 (dd, J = 8.5, 2.2 Hz, 1H), 2.69-2.55 (m, 1H), 2.25-2.07 (m, 1H), 1.95-1.69 (m, 5H), 1.70-1.60 (m, 1H), 1.49-1.30 (m, 1H), 1.30-1.11 (m, 3H), 1.09-0.86 (m, 2H). |
| 44 | 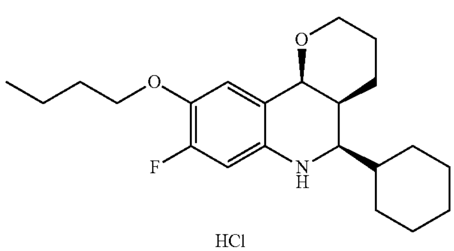 [SMILES: CCCCOc1cc2c(cc1F)N[C@H](C1CCCCC1)[C@@H]1CCCO[C@H]21 ; Cl] | (4aSR*,4RS*, 10bSR*)-9-butoxy-5-cyclohexyl-8-fluoro-3,4,4a,5,6,10b-hexahydro-2H-pyrano[3,2-c]quinoline hydrochloride | $^1$H NMR (CDCl$_3$) δ ppm: 7.96-7.67 (m, 1H), 7.12 (d, J = 5.9 Hz, 1H), 5.01-4.75 (m, 1H), 4.03 (t, J = 6.1 Hz, 2H), 3.65 (d, J = 10.0 Hz, 1H), 3.37-3.13 (m, 2H), 2.78-2.43 (m, 2H), 2.40-2.18 (m, 1H), 2.02-1.45 (m, 13H), 1.38-1.15 (m, 3H), 1.14-1.02 (m, 1H), 0.98 (t, J = 7.2 Hz, 3H). |
| 45 | 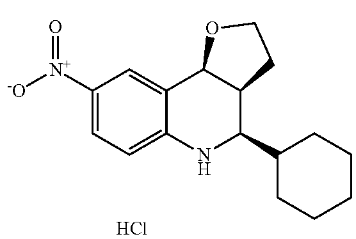 | (3aSR*,4RS*, 9bSR*)-4-cyclohexyl-8-nitro-2,3,3a,4,5,9b-hexahydrofuro[3,2-c]quinoline hydrochloride | $^1$H NMR (CDCl$_3$) δ ppm: 8.24 (d, J = 2.4 Hz, 1H), 7.92 (dd, J = 8.9, 2.4 Hz, 1H), 6.45 (d, J = 9.0 Hz, 1H), 5.08 (d, J = 7.5 Hz, 1H), 4.49 (s, 1H), 3.94-3.66 (m, 2H), 3.30 (dd, J = 9.1, 2.7 Hz, 1H), 2.84-2.63 (m, 1H), 2.00-1.78 (m, 6H), 1.77-1.66 (m, 1H), 1.50-1.14 (m, 4H), 1.14-0.92 (m, 2H). |

| ex. | structure | chemical name | NMR |
|---|---|---|---|
| 46 | 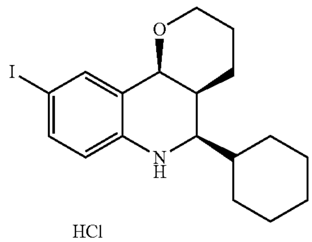 [SMILES: Ic1ccc2c(c1)[C@H]1OCCC[C@H]1[C@@H](C1CCCCC1)N2 ; Cl] | (4aSR*,5RS*,10bSR*)-5-cyclohexyl-9-iodo-3,4,4a,5,6,10b-hexahydro-2H-pyrano[3,2-c]quinoline hydrochloride | ¹H NMR (CDCl₃) δ ppm: 7.63 (s, 1H), 7.28 (d, J = 8.2 Hz, 1H), 6.29 (d, J = 8.3 Hz, 1H), 4.96 (d, J = 5.4 Hz, 1H), 3.61 (dd, J = 10.6, 3.7 Hz, 1H), 3.42 (t, J = 10.9 Hz, 1H), 2.95 (d, J = 9.6 Hz, 1H), 2.31-2.07 (m, 1H), 1.97-1.10 (m, 14H), 1.08-0.81 (m, 2H). |
| 47 | 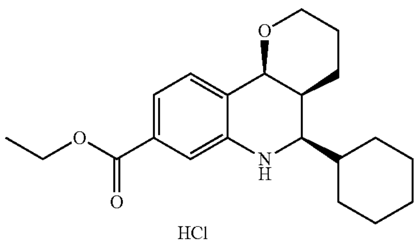 [SMILES: CCOC(=O)c1ccc2c(c1)N[C@H](C1CCCCC1)[C@@H]1CCCO[C@H]21 ; Cl] | (4aSR*,5RS*,10bSR*)-ethyl 5-cyclohexyl-3,4,4a,5,6,10b-hexahydro-2H-pyrano[3,2-c]quinoline-8-carboxylate hydrochloride | ¹H NMR (CDCl₃) δ ppm: 7.43 (d, J = 8.1 Hz, 1H), 7.38 (dd, J = 8.0, 1.4 Hz, 1H), 7.22 (d, J = 1.1 Hz, 1H), 5.02 (d, J = 5.6 Hz, 1H), 4.33 (q, J = 7.1 Hz, 2H), 3.61 (dd, J = 11.4, 4.4 Hz, 1H), 3.37 (td, J = 12.1, 2.1 Hz, 1H), 3.01 (dd, J = 9.6, 2.1 Hz, 1H), 2.32-2.18 (m, 1H), 1.99-1.88 (m, 1H), 1.88-1.74 (m, 3H), 1.75-1.57 (m, 4H), 1.46 (dd, J = 17.2, 7.6 Hz, 3H), 1.37 (t, J = 7.1 Hz, 3H), 1.41-1.10 (m, 4H), 1.06-0.85 (m, 2H). |
| 48 | 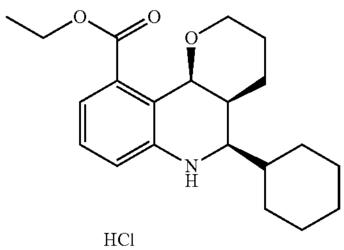 [SMILES: CCOC(=O)c1cccc2c1[C@H]1OCCC[C@H]1[C@@H](C1CCCCC1)N2 ; Cl] | (4aSR*,5RS*,10bSR*)-ethyl 5-cyclohexyl-3,4,4a,5,6,10b-hexahydro-2H-pyrano[3,2-c]quinoline-10-carboxylate hydrochloride | ¹H NMR (CDCl₃) δ ppm: 7.98 (d, J = 7.7 Hz, 1H), 7.64 (d, J = 7.6 Hz, 1H), 7.27 (t, J = 7.7 Hz, 1H), 5.37 (d, J = 2.8 Hz, 1H), 4.45-4.29 (m, 2H), 3.95 (d, J = 10.8 Hz, 1H), 3.72 (d, J = 7.1 Hz, 1H), 3.64 (t, J = 9.8 Hz, 1H), 2.39-2.25 (m, 1H), 2.09-1.97 (m, 1H), 1.97-1.59 (m, 8H), 1.39 (t, J = 7.1 Hz, 3H), 1.54-1.12 (m, 6H). |
| 49 | 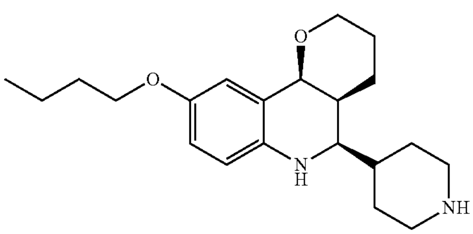 [SMILES: CCCCOc1ccc2c(c1)[C@H]1OCCC[C@H]1[C@@H](C1CCNCC1)N2] | (4aSR*,5RS*,10bSR*)-9-butoxy-5-(piperidin-4-yl)-3,4,4a,5,6,10b-hexahydro-2H-pyrano[3,2-c]quinoline | ¹H NMR (CDCl₃) δ ppm: 6.95 (d, J = 2.2 Hz, 1H), 6.68 (dd, J = 8.6, 2.4 Hz, 1H), 6.50 (d, J = 8.5 Hz, 1H), 4.99 (d, J = 4.2 Hz, 1H), 3.89 (t, J = 6.3 Hz, 2H), 3.67-3.51 (m, 2H), 3.77-3.26 (m, 1H), 3.41 (t, J = 11.5 Hz, 1H), 3.15-2.99 (m, 1H), 2.99-2.77 (m, 2H), 3.15-2.59 (m, 2H), 2.25-2.03 (m, 2H), 2.03-1.87 (m, 1H), 1.87-1.59 (m, 6H), 1.59-1.35 (m, 5H), 0.96 (t, J = 7.3 Hz, 3H). |
| 50 | 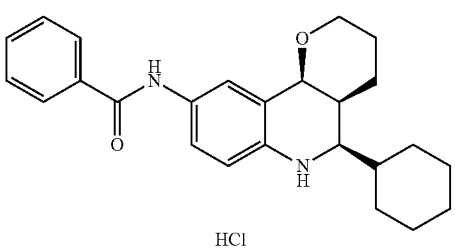 [SMILES: O=C(Nc1ccc2c(c1)[C@H]1OCCC[C@H]1[C@@H](C1CCCCC1)N2)c1ccccc1 ; Cl] | N-((4aSR*,5RS*,10bSR*)-5-cyclohexyl-3,4,4a,5,6,10b-hexahydro-2H-pyrano[3,2-c]quinolin-9-yl)benzamide hydrochloride | ¹H NMR (CDCl₃) δ ppm: 7.87 (d, J = 6.9 Hz, 1H), 7.87-7.68 (m, 1H), 7.58-7.40 (m, 5H), 6.84-6.69 (m, 1H), 5.00 (d, J = 4.8 Hz, 1H), 3.62 (dd, J = 11.1, 3.9 Hz, 1H), 3.45 (t, J = 10.1 Hz, 1H), 3.02 (d, J = 9.5 Hz, 1H), 2.34-2.20 (m, 1H), 2.09-1.96 (m, 1H), 1.91-1.74 (m, 2H), 1.74-1.11 (m, 8H), 1.10-0.72 (m, 4H). |
| 51 | 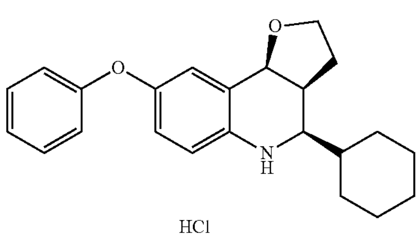 [SMILES: c1ccc(Oc2ccc3c(c2)[C@H]2OCC[C@H]2[C@@H](C2CCCCC2)N3)cc1 ; Cl] | (3aSR*,4RS*,9bSR*)-4-cyclohexyl-8-phenoxy-2,3,3a,4,5,9b-hexahydrofuro[3,2-c]quinoline hydrochloride | ¹H NMR (CDCl₃) δ ppm: 8.12 (d, J = 8.8 Hz, 1H), 7.35 (t, J = 7.8 Hz, 2H), 7.19-7.11 (m, 1H), 7.11 (d, J = 2.8 Hz, 1H), 7.00 (d, J = 8.6 Hz, 2H), 6.91 (dd, J = 8.8, 2.7 Hz, 1H), 5.01 (d, J = 7.5 Hz, 1H), 3.96-3.70 (m, 2H), 3.52 (d, J = 7.9 Hz, 1H), 3.01-2.82 (m, 1H), 2.62-2.48 (m, 1H), 2.48-2.31 (m, 1H), 2.30-2.16 (m, 1H), 2.16-1.98 (m, 2H), 1.92-1.75 (m, 2H), 1.75-1.59 (m, 1H), 1.46-1.02 (m, 5H). |

-continued

| ex. | structure | chemical name | NMR |
|---|---|---|---|
| 52 | (structure) HCl | (4aSR*,5RS*,10bSR*)-5-cyclohexyl-9-ethyl-3,4,4a,5,6,10b-hexahydro-2H-pyrano[3,2-c]quinoline hydrochloride | ¹H NMR (CDCl₃) δ ppm: 7.99 (d, J = 8.1 Hz, 1H), 7.41 (s, 1H), 7.14 (d, J = 7.6 Hz, 1H), 4.91 (d, J = 5.1 Hz, 1H), 3.65 (d, J = 10.1 Hz, 1H), 3.41-3.16 (m, 2H), 2.66 (q, J = 15.1, 7.6 Hz, 2H), 2.60-2.42 (m, 1H), 2.38-2.20 (m, 1H), 2.00-1.48 (m, 9H), 1.48-1.15 (m, 4H), 1.23 (t, J = 7.6 Hz, 3H), 1.14-0.85 (m, 1H). |
| 53 | (structure) HCl | (4aSR*,5RS*,10bSR*)-9-phenoxy-5-(tetrahydro-2H-pyran-4-yl)-3,4,4a,5,6,10b-hexahydro-2H-pyrano[3,2-c]quinoline hydrochloride | ¹H NMR (CDCl₃) δ ppm: 7.92 (d, J = 8.0 Hz, 1H), 7.35 (t, J = 7.9 Hz, 2H), 7.20 (d, J = 2.0 Hz, 1H), 7.14 (t, J = 7.4 Hz, 1H), 6.99 (d, J = 7.7 Hz, 2H), 6.88 (dd, J = 7.9, 2.1 Hz, 1H), 4.91 (d, J = 5.2 Hz, 1H), 4.03 (dd, J = 9.9, 4.5 Hz, 2H), 3.62 (d, J = 11.1 Hz, 1H), 3.50-3.20 (m, 4H), 2.65-2.38 (m, 3H), 1.92-1.48 (m, 6H), 1.48-1.28 (m, 1H). |
| 54 | (structure) HCl | (4aSR*,5RS*,10bSR*)-methyl 5-cyclohexyl-3,4,4a,5,6,10b-hexahydro-2H-pyrano[3,2-c]quinoline-9-carboxylate hydrochloride | ¹H NMR (CDCl₃) δ ppm: 8.08 (s, 1H), 7.77 (dd, J = 8.4, 1.6 Hz, 1H), 6.73 (d, J = 8.4 Hz, 1H), 4.99 (d, J = 5.4 Hz, 1H), 3.86 (s, 3H), 3.64 (dd, J = 11.7, 4.3 Hz, 1H), 3.39 (td, J = 12.0, 1.9 Hz, 1H), 3.09 (dd, J = 9.7, 1.6 Hz, 1H), 2.38-2.20 (m, 1H), 2.12-1.97 (m, 1H), 1.90-1.46 (m, 8H), 1.46-1.14 (m, 4H), 1.14-0.86 (m, 2H). |
| 55 | (structure) HCl | (4aSR*,5RS*,10bSR*)-9-(4-chlorophenoxy)-5-cyclohexyl-3,4,4a,5,6,10b-hexahydro-2H-pyrano[3,2-c]quinoline hydrochloride | ¹H NMR (CDCl₃) δ ppm: 8.03-7.88 (m, 1H), 7.30 (d, J = 8.8 Hz, 2H), 7.17 (d, J = 1.8 Hz, 1H), 6.93 (d, J = 8.9 Hz, 2H), 6.98-6.90 (m, 1H), 4.88 (d, J = 5.1 Hz, 1H), 3.61 (dd, J = 11.3, 2.6 Hz, 1H), 3.36-3.18 (m, 2H), 2.70-2.44 (m, 2H), 2.31-2.10 (m, 1H), 1.95-1.74 (m, 4H), 1.74-1.43 (m, 5H), 1.44-1.13 (m, 4H), 1.13-0.88 (m, 1H). |
| 56 | (structure) HCl | (4aSR*,5RS*,10bSR*)-5-cyclopentyl-9-phenoxy-3,4,4a,5,6,10b-hexahydro-2H-pyrano[3,2-c]quinoline hydrochloride | ¹H NMR (CDCl₃) δ ppm: 8.10 (d, J = 8.5 Hz, 1H), 7.34 (t, J = 7.8 Hz, 2H), 7.22 (d, J = 2.3 Hz, 1H), 7.14 (t, J = 7.4 Hz, 1H), 6.99 (d, J = 7.9 Hz, 2H), 6.91 (dd, J = 8.4, 2.0 Hz, 1H), 4.91 (d, J = 5.2 Hz, 1H), 3.61 (d, J = 10.5 Hz, 1H), 3.38-3.21 (m, 2H), 2.80-2.63 (m, 1H), 2.63-2.51 (m, 1H), 2.51-2.37 (m, 1H), 2.17 (s, 1H), 2.00-1.84 (m, 2H), 1.84-1.46 (m, 8H), 1.36-1.14 (m, 1H). |
| 57 | (structure) HCl | (4aSR*,5RS*,10bSR*)-5-cyclohexyl-9-p-tolyl-3,4,4a,5,6,10b-hexahydro-2H-pyrano[3,2-c]quinoline hydrochloride | ¹H NMR (CDCl₃) δ ppm: 8.04 (d, J = 7.7 Hz, 1H), 7.78 (d, J = 1.1 Hz, 1H), 7.50 (d, J = 6.7 Hz, 1H), 7.42 (d, J = 8.1 Hz, 2H), 7.24 (d, J = 8.4 Hz, 2H), 5.00 (d, J = 5.1 Hz, 1H), 3.64 (dd, J = 11.2, 3.0 Hz, 1H), 3.44-3.24 (m, 2H), 2.74-2.48 (m, 2H), 2.41 (s, 3H), 2.35-2.16 (m, 1H), 1.97-1.50 (m, 8H), 1.50-1.14 (m, 4H), 1.14-0.87 (m, 1H). |

-continued

| ex. | structure | chemical name | NMR |
|---|---|---|---|
| 58 | (structure) | 4-((4aSR*,5RS*,10bSR*)-5-cyclohexyl-3,4,4a,5,6,10b-hexahydro-2H-pyrano[3,2-c]quinolin-9-yl)phenol hydrochloride | ¹H NMR (DMSO) δ ppm: 7.41 (s, 1H), 7.36 (d, J = 8.5 Hz, 2H), 7.29 (d, J = 8.2 Hz, 1H), 6.93 (d, J = 7.9 Hz, 1H), 6.80 (d, J = 8.5 Hz, 2H), 4.98 (d, J = 5.1 Hz, 1H), 3.53 (d, J = 8.9 Hz, 1H), 3.26 (t, J = 11.1 Hz, 1H), 3.07 (d, J = 9.2 Hz, 1H), 2.28-2.11 (m, 2H), 1.87-1.69 (m, 3H), 1.69-1.38 (m, 5H), 1.36-1.07 (m, 4H), 1.08-0.81 (m, 2H). |
| 59 | (structure) | (4aSR*,5RS*,10bSR*)-5-cyclohexyl-9-pentyl-3,4,4a,5,6,10b-hexahydro-2H-pyrano[3,2-c]quinoline | ¹H NMR (CDCl₃) δ ppm: 7.18 (s, 1H), 6.86 (dd, J = 8.0, 1.5 Hz, 1H), 6.45 (d, J = 8.1 Hz, 1H), 5.02 (d, J = 5.5 Hz, 1H), 3.66 (s, 1H), 3.59 (dd, J = 11.2, 4.3 Hz, 1H), 3.43 (td, J = 11.7, 1.7 Hz, 1H), 2.94 (dd, J = 9.6, 1.8 Hz, 1H), 2.49 (t, J = 7.7 Hz, 2H), 2.31-2.12 (m, 1H), 2.00-1.60 (m, 8H), 1.52-1.05 (m, 11H), 1.06-0.76 (m, 2H), 0.88 (t, J = 6.7 Hz, 3H). |
| 60 | (structure) | (4aSR*,5RS*,10bSR*)-5-cyclohexyl-9-pentyl-3,4,4a,5,6,10b-hexahydro-2H-pyrano[3,2-c]quinoline hydrochloride | ¹H NMR (CD₃OD) δ ppm: 7.49 (s, 1H), 7.31 (dd, J = 8.1, 1.4 Hz, 1H), 7.25 (d, J = 8.2 Hz, 1H), 5.04 (d, J = 5.1 Hz, 1H), 3.67 (dd, J = 11.9, 4.2 Hz, 1H), 3.41-3.19 (m, 2H), 2.69 (t, J = 7.6 Hz, 2H), 2.63-2.54 (m, 1H), 2.09-1.71 (m, 8H), 1.71-1.49 (m, 3H), 1.49-1.27 (m, 7H), 1.26-1.01 (m, 3H), 0.90 (t, J = 6.8 Hz, 3H). |
| 61 | (structure) | (4aSR*,5RS*,10bSR*)-5-cyclohexyl-9-pentyl-3,4,4a,5,6,10b-hexahydro-2H-pyrano[3,2-c]quinoline hydrochloride | ¹H NMR (CDCl₃) δ ppm: 8.09 (d, J = 8.2 Hz, 1H), 7.25 (s, 1H), 7.08 (dd, J = 8.2, 1.8 Hz, 1H), 4.60 (d, J = 3.3 Hz, 1H), 3.93-3.81 (m, 1H), 3.77-3.58 (m, 2H), 2.68-2.50 (m, 3H), 2.08-1.74 (m, 8H), 1.74-1.45 (m, 6H), 1.43-1.19 (m, 7H), 0.90 (t, J = 6.8 Hz, 3H). |
| 62 | (structure) | ((4aSR*,5RS*,10bSR*)-5-cyclohexyl-9-(piperidin-1-ylsulfonyl)-3,4,4a,5,6,10b-hexahydro-2H-pyrano[3,2-c]quinoline hydrochloride | ¹H NMR (CDCl₃) δ ppm: 7.65 (d, J = 2.6 Hz, 1H), 7.33 (dd, J = 8.4, 2.2 Hz, 1H), 6.42 (d, J = 8.5 Hz, 1H), 4.93 (d, J = 5.5 Hz, 1H), 4.16 (s, 1H), 3.56 (dd, J = 11.5, 4.4 Hz, 1H), 3.30 (td, J = 12.2, 2.1 Hz, 1H), 2.98 (dd, J = 9.7, 1.8 Hz, 1H), 2.93-2.86 (m, 4H), 2.22-2.11 (m, 1H), 1.88-1.70 (m, 4H), 1.69-1.50 (m, 7H), 1.45-1.30 (m, 4H), 1.30-1.07 (m, 4H), 0.99-0.82 (m, 2H). |
| 63 | (structure) | 4aSR*,5RS*,10bSR*)-9-pentyl-5-(tetrahydro-2H-pyran-4-yl)-3,4,4a,5,6,10b-hexahydro-2H-pyrano[3,2-c]quinoline hydrochloride | ¹H NMR (CDCl₃) δ ppm: 8.00 (d, J = 8.6 Hz, 1H), 7.41 (s, 1H), 7.11 (d, J = 8.6 Hz, 1H), 4.97 (s, 1H), 4.07 (d, J = 6.6 Hz, 2H), 3.67 (d, J = 10.4 Hz, 1H), 3.62-3.24 (m, 4H), 2.92-2.35 (m, 4H), 1.94-1.18 (m, 14H), 0.90 (t, J = 6.6 Hz, 3H). |

-continued

| ex. | structure | chemical name | NMR |
|---|---|---|---|
| 64 | HCl | (4aSR*,5RS*,10bSR*)-5-cyclohexyl-9-morpholino-3,4,4a,5,6,10b-hexahydro-2H-pyrano[3,2-c]quinoline hydrochloride | $^1$H NMR (CDCl$_3$) δ ppm: 7.98 (d, J = 8.0 Hz, 1H), 7.65 (s, 1H), 7.23 (d, J = 8.1 Hz, 1H), 4.97 (d, J = 3.8 Hz, 1H), 4.47-4.21 (m, 4H), 3.68 (d, J = 5.7 Hz, 1H), 3.64-3.51 (m, 4H), 3.27 (t, J = 10.7 Hz, 1H), 3.19 (d, J = 8.4 Hz, 1H), 2.41 (d, J = 8.9 Hz, 1H), 2.20 (d, J = 11.6 Hz, 1H), 1.96-1.61 (m, 7H), 1.61-1.50 (m, 1H), 1.47-1.09 (m, 5H), 1.09-0.90 (m, 1H). |
| 65 | HCl | (4aSR*,5RS*,10bSR*)-5-(1-adamantyl)-9-phenoxy-3,4,4a,5,6,10b-hexahydro-2H-pyrano[3,2-c]quinoline hydrochloride | $^1$H NMR (CDCl$_3$) δ ppm: 8.38 (d, J = 8.0 Hz, 1H), 7.34 (t, J = 7.9 Hz, 2H), 7.20 (d, J = 2.0 Hz, 1H), 7.13 (t, J = 7.3 Hz, 1H), 6.99 (d, J = 7.9 Hz, 2H), 6.84 (dd, J = 8.6, 2.3 Hz, 1H), 4.84 (d, J = 5.6 Hz, 1H), 3.59 (dd, J = 11.6, 3.8 Hz, 1H), 3.34 (td, J = 12.2, 2.0 Hz, 1H), 2.98 (s, 1H), 2.67-2.57 (m, 1H), 2.16-2.06 (m, 6H), 2.05-1.95 (m, 1H), 1.95-1.84 (m, 2H), 1.81-1.67 (m, 9H), 1.62-1.51 (m, 1H). |
| 66 | HCl | (4aSR*,5RS*,10bSR*)-9-(2-chlorophenoxy)-5-cyclohexyl-3,4,4a,5,6,10b-hexahydro-2H-pyrano[3,2-c]quinoline hydrochloride | $^1$H NMR (CDCl$_3$) δ ppm: 8.00-7.85 (m, 1H), 7.46 (d, J = 7.8 Hz, 1H), 7.25-7.20 (m, 1H), 7.17-7.05 (m, 2H), 7.00 (d, J = 7.7 Hz, 1H), 6.91-6.81 (m, 1H), 4.87 (d, J = 3.6 Hz, 1H), 3.59 (d, J = 10.8 Hz, 1H), 3.38-3.13 (m, 2H), 2.70-2.39 (m, 2H), 2.28-2.10 (m, 1H), 1.97-1.42 (m, 7H), 1.41-1.12 (m, 4H), 1.02 (dd, J = 22.0, 12.4 Hz, 1H). |
| 67 | HCl | (4aSR*,5RS*,10bSR*)-5-cyclohexyl-9-(2-morpholino-ethoxy)-3,4,4a,5,6,10b-hexahydro-2H-pyrano[3,2-c]quinoline | $^1$H NMR (CDCl$_3$) δ ppm: 6.97 (d, J = 2.5 Hz, 1H), 6.68 (dd, J = 8.6, 2.8 Hz, 1H), 6.46 (d, J = 8.6 Hz, 1H), 4.99 (d, J = 5.4 Hz, 1H), 4.05 (t, J = 5.8 Hz, 2H), 3.79-3.67 (m, 4H), 3.59 (dd, J = 11.2, 4.4 Hz, 1H), 3.41 (td, J = 11.9, 2.1 Hz, 1H), 2.90 (d, J = 9.6 Hz, 1H), 2.76 (t, J = 5.8 Hz, 2H), 2.62-2.53 (m, 4H), 2.28-2.11 (m, 1H), 1.99-1.46 (m, 6H), 1.35-1.10 (m, 5H), 1.04-0.73 (m, 4H). |
| 68 | HCl | (4aSR*,5RS*,10bSR*)-propyl 5-(1-adamantyl)-3,4,4a,5,6,10b-hexahydro-2H-pyrano[3,2-c]quinoline-9-carboxylate hydrochloride | $^1$H NMR (CDCl$_3$) δ ppm: 8.03 (s, 1H), 7.74 (dd, J = 8.3, 1.5 Hz, 1H), 6.50 (d, J = 8.5 Hz, 1H), 4.99 (d, J = 5.2 Hz, 1H), 4.32-4.13 (m, 2H), 3.59 (d, J = 7.6 Hz, 1H), 3.42 (t, J = 11.4 Hz, 1H), 2.94 (s, 1H), 2.38-2.26 (m, 1H), 2.09-2.00 (m, 3H), 1.91-1.82 (m, 1H), 1.83-1.60 (m, 15H), 1.50-1.36 (m, 2H), 1.00 (t, J = 7.4 Hz, 3H). |
| 69 | HCl | (4aSR*,5RS*,10bSR*)-methyl 5-cyclohexyl-7-methyl-3,4,4a,5,6,10b-hexahydro-2H-pyrano[3,2-c]quinoline-8-carboxylate hydrochloride | $^1$H NMR (CDCl$_3$) δ ppm: 7.43 (d, J = 8.2 Hz, 1H), 7.40 (d, J = 8.2 Hz, 1H), 4.98 (d, J = 5.5 Hz, 1H), 3.90 (s, 3H), 3.61 (dd, J = 12.4, 3.7 Hz, 1H), 3.31 (td, J = 11.9, 2.0 Hz, 1H), 3.15 (d, J = 9.5 Hz, 1H), 2.54 (s, 3H), 2.39-2.28 (m, 1H), 2.11-1.98 (m, 1H), 1.98-1.59 (m, 7H), 1.58-1.07 (m, 6H), 1.07-0.84 (m, 1H). |

| ex. | structure | chemical name | NMR |
|---|---|---|---|
| 70 | 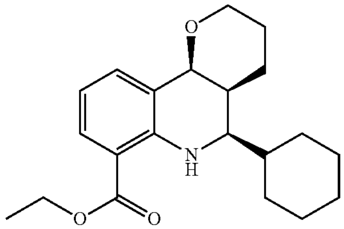 | (4aSR*,5RS*,10bSR*)-ethyl 5-cyclohexyl-3,4,4a,5,6,10b-hexahydro-2H-pyrano[3,2-c]quinoline-7-carboxylate hydrochloride | $^1$H NMR (CDCl$_3$) δ ppm: 7.87 (s, 1H), 7.81 (ddd, J = 8.0, 1.6, 0.9 Hz, 1H), 7.50 (d, J = 7.4 Hz, 1H), 6.64-6.50 (m, 1H), 5.01 (d, J = 5.5 Hz, 1H), 4.37-4.24 (m, 2H), 3.59 (dd, J = 11.4, 4.7 Hz, 1H), 3.41 (td, J = 12.3, 2.3 Hz, 1H), 3.07 (dd, J = 9.9, 2.4 Hz, 1H), 2.25-2.16 (m, 1H), 2.16-2.05 (m, 1H), 1.92-1.74 (m, 3H), 1.75-1.63 (m, 2H), 1.63-1.44 (m, 3H), 1.37 (t, J = 7.1 Hz, 3H), 1.35-1.11 (m, 4H), 1.10-0.83 (m, 2H). |
| 71 | 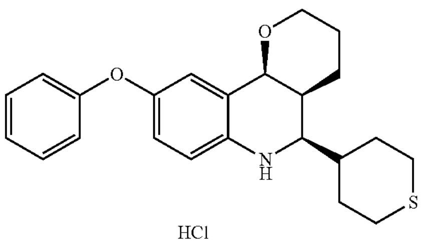 [SMILES: c1ccc(Oc2ccc3c(c2)[C@H]2OCCC[C@H]2[C@@H](C2CCSCC2)N3)cc1 ; Cl] | (4aSR*,5RS*,10bSR*)-9-phenoxy-5-(tetrahydro-2H-thiopyran-4-yl)-3,4,4a,5,6,10b-hexahydro-2H-pyrano[3,2-c]quinoline hydrochloride | $^1$H NMR (CDCl$_3$) δ ppm: 8.00 (d, J = 8.7 Hz, 1H), 7.36 (dd, J = 8.5, 7.5 Hz, 2H), 7.20 (d, J = 2.0 Hz, 1H), 7.15 (t, J = 7.4 Hz, 1H), 7.00 (dd, J = 8.6, 1.0 Hz, 2H), 6.89 (dd, J = 8.8, 2.7 Hz, 1H), 4.88 (d, J = 5.3 Hz, 1H), 3.61 (dd, J = 11.5, 3.4 Hz, 1H), 3.40-3.14 (m, 2H), 2.93-2.75 (m, 1H), 2.75-2.57 (m, 4H), 2.43-2.27 (m, 1H), 2.27-2.11 (m, 1H), 1.93-1.36 (m, 6H). |
| 72 | 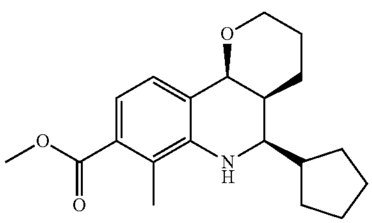 | (4aSR*,5RS*,10bSR*)-methyl 5-cyclopentyl-7-methyl-3,4,4a,5,6,10b-hexahydro-2H-pyrano[3,2-c]quinoline-8-carboxylate hydrochloride | $^1$H NMR (CDCl$_3$) δ ppm: 7.32 (d, J = 8.0 Hz, 1H), 7.21 (d, J = 8.1 Hz, 1H), 5.04 (d, J = 5.7 Hz, 1H), 3.87 (s, 3H), 3.59 (dd, J = 11.5, 4.6 Hz, 1H), 3.34 (td, J = 11.9, 2.2 Hz, 1H), 3.07 (dd, J = 10.1, 2.1 Hz, 1H), 2.31 (s, 3H), 2.23-1.93 (m, 4H), 1.90-1.78 (m, 1H), 1.78-1.55 (m, 5H), 1.54-1.44 (m, 1H), 1.43-1.13 (m, 3H). |
| 73 | 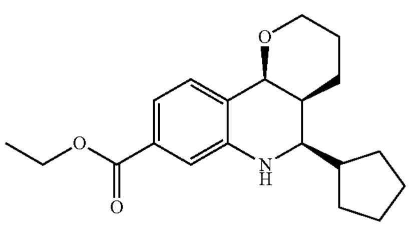 | (4aSR*,5RS*,10bSR*)-ethyl 5-cyclopentyl-3,4,43,5,6,10b-hexahydro-2H-pyrano[3,2-c]quinoline-8-carboxylate hydrochloride | $^1$H NMR (CDCl$_3$) δ ppm: 8.55 (s, 1H), 7.93 (d, J = 8.0 Hz, 1H), 7.68 (d, J = 8.0 Hz, 1H), 4.99 (d, J = 5.6 Hz, 1H), 4.27 (dq, J= 10.8, 7.1 Hz, 1H), 4.12 (dq, J = 14.3, 7.1 Hz, 1H), 3.70 (d, J = 11.1 Hz, 1H), 3.36-3.18 (m, 2H), 2.77-2.58 (m, 1H), 2.57-2.35 (m, 2H), 2.02-1.84 (m, 2H), 1.79-1.58 (m, 7H), 1.58-1.46 (m, 1H), 1.32-1.21 (m, 1H), 1.17 (t, J = 7.1 Hz, 3H). |
| 74 | 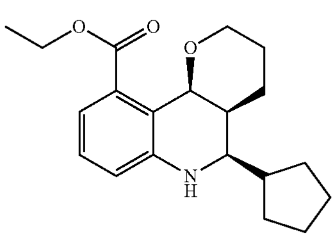 | (4aSR*,5RS*,10bSR*)-ethyl 5-cyclopentyl-3,4,4a,5,6,10b-hexahydro-2H-pyrano[3,2-c]quinoline-10-carboxylate hydrochloride | $^1$H NMR (CDCl$_3$) δ ppm: 8.19-8.06 (m, 1H), 7.48 (d, J = 7.2 Hz, 1H), 7.43-7.34 (m, 1H), 5.26 (d, J = 5.7 Hz, 1H), 4.40-4.19 (m, 2H), 3.54 (d, J = 11.7 Hz, 1H), 3.32 (d, J = 10.1 Hz, 1H), 3.04 (t, J = 11.3 Hz, 1H), 2.80-2.56 (m, 1H), 2.55-2.34 (m, 2H), 2.04-1.83 (m, 2H), 1.83-1.48 (m, 8H), 1.34 (t, J = 7.1 Hz, 3H), 1.31-1.16 (m, 1H). |

-continued

| ex. | structure | chemical name | NMR |
|---|---|---|---|
| 75 | 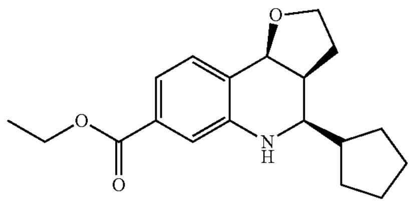 | (3aSR*,4RS*,9bSR*)-ethyl 4-cyclopentyl-2,3,3a,4,5,9b-hexahydrofuro[3,2-c]quinoline-7-carboxylate hydrochloride | $^1$H NMR (CDCl$_3$) δ ppm: 8.56 (s, 1H), 7.90 (d, J = 7.8 Hz, 1H), 7.58 (d, J = 8.0 Hz, 1H), 5.13 (d, J = 7.1 Hz, 1H), 4.42-4.20 (m, 1H), 4.21-4.04 (m, 1H), 3.96-3.75 (m, 2H), 3.47 (d, J = 5.1 Hz, 1H), 3.05-2.85 (m, 1H), 2.63-2.36 (m, 3H), 2.23-2.03 (m, 1H), 2.03-1.88 (m, 1H), 1.83-1.46 (m, 5H), 1.42-1.28 (m, 1H), 1.19 (t, J = 6.4 Hz, 3H). |
| 76 | 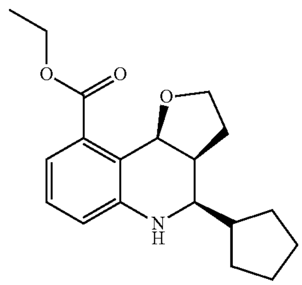 | (3aSR*,4RS*,9bSR*)-ethyl 4-cyclopentyl-2,3,3a,4,5,9b-hexahydrofuro[3,2-c]quinoline-9-carboxylate hydrochloride | $^1$H NMR (CDCl$_3$) δ ppm: 8.12 (d, J = 7.0 Hz, 1H), 7.61 (d, J = 7.5 Hz, 1H), 7.28 (t, J = 7.7 Hz, 1H), 5.68 (d, J = 7.8 Hz, 1H), 4.32 (qd, J = 7.1, 2.1 Hz, 2H), 3.75 (q, J = 7.8 Hz, 1H), 3.65 (td, J = 8.7, 4.0 Hz, 1H), 3.47 (d, J = 8.1 Hz, 1H), 2.94-2.76 (m, 1H), 2.56-2.38 (m, 2H), 2.38-2.22 (m, 1H), 2.07-1.96 (m, 1H), 1.96-1.81 (m, 1H), 1.78 - 1.57 (m, 6H), 1.32 (t, J = 7.1 Hz, 3H), 1.28-1.17 (m, 1H). |
| 77 | 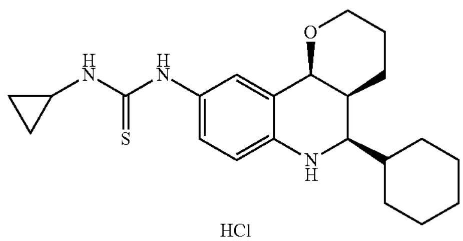 [SMILES: S=C(Nc1ccc2c(c1)[C@H]1OCCC[C@H]1[C@@H](C1CCCCC1)N2)NC1CC1 ; Cl] | 1-((4aSR*,5RS*,10bSR*)-5-cyclohexyl-3,4,4a,5,6,10b-hexahydro-2H-pyrano[3,2-c]quinolin-9-yl)-3-cyclopropylthiourea hydrochloride | $^1$H NMR (DMSO) δ ppm: 9.04 (s, 1H), 7.73 (s, 1H), 7.08 (s, 1H), 6.92 (d, J = 7.6 Hz, 1H), 6.65 (d, J = 8.7 Hz, 1H), 4.86 (d, J = 4.3 Hz, 1H), 3.41-3.16 (m, 2H), 2.93 (d, J = 9.8 Hz, 1H), 2.85-2.64 (m, 1H), 2.19-1.91 (m, 2H), 1.79-1.30 (m, 8H), 1.17 (s, 4H), 1.01-0.76 (m, 2H), 0.78-0.58 (m, 2H), 0.58-0.39 (m, 2H). |
| 78 | 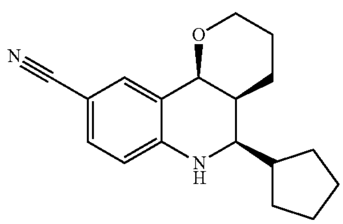 | (4aSR*,5RS*,10bSR*)-5-cyclopentyl-3,4,4a,5,6,10b-hexahydro-2H-pyrano[3,2-c]quinoline-9-carbonitrile hydrochloride | $^1$H NMR (CDCl$_3$) δ ppm: 7.62 (s, 1H), 7.27 (dd, J = 8.4, 2.0 Hz, 2H), 6.44 (d, J = 8.4 Hz, 1H), 4.96 (d, J = 5.6 Hz, 1H), 3.63 (dd, J = 11.7, 4.5 Hz, 1H), 3.36 (td, J = 12.0, 2.3 Hz, 1H), 3.11 (dd, J = 9.9, 2.4 Hz, 1H), 2.19-2.10 (m, 1H), 2.03-1.87 (m, 2H), 1.87-1.77 (m, 1H), 1.77-1.46 (m, 7H), 1.37-1.13 (m, 3H). |
| 79 | 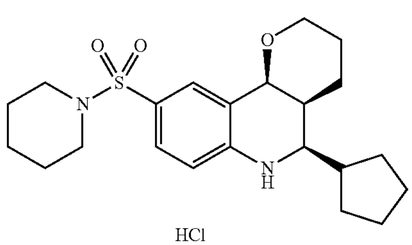 [SMILES: O=S(=O)(c1ccc2c(c1)[C@H]1OCCC[C@H]1[C@@H](C1CCCC1)N2)N1CCCCC1 ; Cl] | (4aSR*,5RS*,10bSR*)-5-cyclopentyl-9-(piperidin-1-ylsulfonyl)-3,4,4a,5,6,10b-hexahydro-2H-pyrano[3,2-c]quinoline hydrochloride | $^1$H NMR (CDCl$_3$) δ ppm: 7.40 (s, 1H), 7.26 (dd, J = 8.6, 2.0 Hz, 1H), 6.80 (d, J = 8.6 Hz, 1H), 6.19 (s, 1H), 4.96 (d, J = 5.5 Hz, 1H), 3.54 (d, J = 8.9 Hz, 1H), 3.19 (td, J = 11.6, 2.3 Hz, 1H), 3.08 (dd, J = 9.7, 1.5 Hz, 1H), 2.84-2.75 (m, 4H), 2.62-2.38 (m, 1H), 2.15-1.94 (m, 2H), 1.94-1.70 (m, 2H), 1.57 (d, J = 21.5 Hz, 10H), 1.41-1.28 (m, 2H), 1.13 (dt, J = 12.7, 9.9 Hz, 3H). |
| 80 | 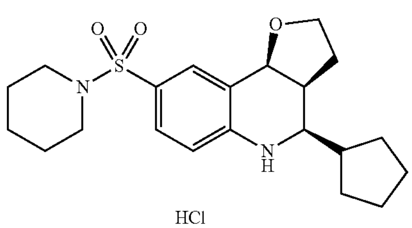 [SMILES: O=S(=O)(c1ccc2c(c1)[C@H]1OCC[C@H]1[C@@H](C1CCCC1)N2)N1CCCCC1 ; Cl] | (3aSR*,4RS*,9bSR*)-4-cyclopentyl-8-(piperidin-1-ylsulfonyl)-2,3,3a,4,5,9b-hexahydrofuro[3,2-c]quinoline hydrochloride | $^1$H NMR (CDCl$_3$) δ ppm: 7.37 (d, J = 1.7 Hz, 1H), 7.24 (dd, J = 8.6, 2.1 Hz, 1H), 6.83 (d, J = 8.6 Hz, 1H), 6.12 (s, 1H), 5.01 (d, J = 7.6 Hz, 1H), 3.72 (q, J = 8.0 Hz, 1H), 3.59 (td, J = 8.8, 3.5 Hz, 1H), 3.26-3.15 (m, 1H), 2.84-2.71 (m, 4H), 2.63- 2.51 (m, 1H), 2.16-2.00 (m. 1H), 1.95-1.42 (m, 12H), 1.43-1.14 (m, 4H). |

-continued

| ex. | structure | chemical name | NMR |
|---|---|---|---|
| 81 | HCl | (4aSR*,5RS*,10bSR*)-5-cyclopentyl-N,N-dimethyl-3,4,4a,5,6,10b-hexahydro-2H-pyrano[3,2-c]quinoline-9-sulfonamide hydrochloride | $^1$H NMR (CDCl$_3$) δ ppm: 7.43 (s, 1H), 7.28 (dd, J = 8.6, 2.2 Hz, 1H), 6.81 (d, J = 8.6 Hz, 1H), 6.21 (s, 1H), 4.97 (d, J = 5.5 Hz, 1H), 3.54 (dd, J = 12.0, 3.2 Hz, 1H), 3.20 (td, J = 11.5, 2.3 Hz, 1H), 3.08 (dd, J = 9.7, 1.6 Hz, 1H), 2.52 (s, 6H), 2.17-1.95 (m, 2H), 1.95-1.70 (m, 2H), 1.70-1.37 (m, 7H), 1.29-0.97 (m, 3H). |
| 82 | HCl | (4aSR*,5RS*,10bSR*)-5-cyclopentyl-N,N-diethyl-3,4,4a,5,6,10b-hexahydro-2H-pyrano[3,2-c]quinoline-9-sulfonamide hydrochloride | $^1$H NMR (DMSO) δ ppm: 7.44 (s, 1H), 7.29 (dd, J = 8.7, 1.6 Hz, 1H), 6.75 (d, J = 8.6 Hz, 1H), 6.11 (s, 1H), 4.93 (d, J = 5.2 Hz, 1H), 3.52 (d, J = 8.7 Hz, 1H), 3.16 (t, J = 11.6 Hz, 1H), 3.06-3.03 (m, 1H), 3.05 (q, J = 6.9 Hz, 4H), 2.16-1.91 (m, 2H), 1.91-1.67 (m, 2H), 1.68-1.36 (m, 7H), 1.27-1.04 (m, 3H), 1.00 (t, J = 7.1 Hz, 6H). |
| 83 | HCl | (3aSR*,4RS*,9bSR*)-4-cyclohexyl-2,3,3a,4,5,9b-hexahydrofuro[3,2-c]quinolin-8-ol hydrochloride | $^1$H NMR (DMSO) δ ppm: 7.18-6.90 (m, 1H), 6.82-6.60 (m, 2H), 4.97 (d, J = 7.7 Hz, 1H), 3.79-3.68 (m, 1H), 3.60-3.47 (m, 1H), 3.42-3.25 (m, 1H), 2.84-2.63 (m, 1H), 2.15-1.99 (m, 1H), 1.99-1.56 (m, 7H), 1.33-0.93 (m, 5H). |
| 84 | HCl | (3aSR*,4RS*,9bSR*)-4-cyclohexyl-8-pentyl-2,3,3a,4,5,9b-hexahydrofuro[3,2-c]quinoline hydrochloride | $^1$H NMR (DMSO) δ ppm: 6.99 (s, 1H), 6.88 (d, J = 7.4 Hz, 1H), 6.81 (d, J = 7.1 Hz, 1H), 4.98 (d, J = 7.9 Hz, 1H), 3.67 (q, J = 7.9 Hz, 1H), 3.60-3.45 (m, 1H), 3.24-3.10 (m, 1H), 2.75-2.59 (m, 1H), 2.44 (t, J = 7.6 Hz, 2H), 2.15-2.00 (m, 1H), 1.95-1.69 (m, 4H), 1.69-1.58 (m, 1H), 1.58-1.38 (m, 3H), 1.39-1.09 (m, 6H), 1.09-0.90 (m, 2H), 0.85 (t, J = 6.9 Hz, 3H). |
| 85 | HCl | (3aSR*,4RS*,9bSR*)-8-pentyl-4-(tetrahydro-2H-pyran-4-yl)-2,3,3a,4,5,9b-hexahydrofuro[3,2-c]quinoline hydrochloride | $^1$H NMR (CDCl$_3$) δ ppm: 7.97 (d, J = 7.5 Hz, 1H), 7.35 (s, 1H), 7.09 (d, J = 7.4 Hz, 1H), 5.11 (d, J = 7.7 Hz, 1H), 4.07 (d, J = 8.8 Hz, 2H), 3.89 (q, J = 7.6 Hz, 1H), 3.78 (td, J = 8.6, 4.8 Hz, 1H), 3.48 (t, J = 12.1 Hz, 3H), 2.92 (q, J = 7.7 Hz, 1H), 2.68-2.55 (m, 2H), 2.55-2.35 (m, 2H), 2.20-2.02 (m, 1H), 2.01-1.84 (m, 1H), 1.70-1.41 (m, 5H), 1.41-1.19 (m, 4H), 0.90 (t, J = 6.8 Hz, 3H). |
| 86 | 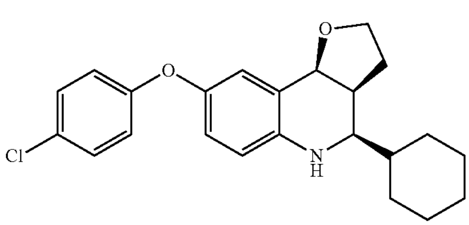 [SMILES: Clc1ccc(Oc2ccc3c(c2)[C@H]2OCC[C@H]2[C@@H](C2CCCCC2)N3)cc1] | (3aSR*,4RS*,9bSR*)-8-(4-chlorophenoxy)-4-cyclohexyl-2,3,3a,4,5,9b-hexahydrofuro[3,2-c]quinoline | $^1$H NMR (DMSO) δ ppm: 7.35 (d, J = 8.9 Hz, 2H), 6.88 (d, J = 8.9 Hz, 2H), 6.80-6.67 (m, 3H), 5.20 (s, 1H), 4.95 (d, J = 7.8 Hz, 1H), 3.74-3.49 (m, 2H), 3.04 (d, J = 8.4 Hz, 1H), 2.66-2.53 (m, 1H), 2.23-2.02 (m, 1H), 1.90-1.56 (m, 5H), 1.42-1.09 (m, 4H), 1.09-0.83 (m, 2H). |

| ex. | structure | chemical name | NMR |
|---|---|---|---|
| 87 | 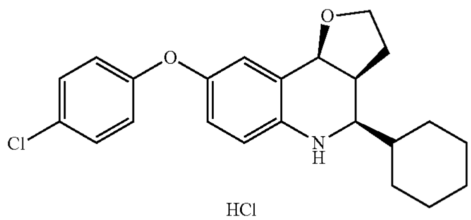 [SMILES: Clc1ccc(Oc2ccc3c(c2)[C@H]2OCC[C@H]2[C@@H](C2CCCCC2)N3)cc1 ; Cl] | (3aSR*,4RS*,9bSR*)-8-(4-chlorophenoxy)-4-cyclohexyl-2,3,3a,4,5,9b-hexahydrofuro[3,2-c]quinoline hydrochloride | $^1$H NMR (DMSO) δ ppm: 7.36 (d, J = 8.9 Hz, 2H), 6.90 (d, J = 8.9 Hz, 2H), 6.84 (d, J = 8.5 Hz, 1H), 6.79-6.69 (m, 2H), 4.96 (d, J = 7.8 Hz, 1H), 3.67 (q, J = 7.8 Hz, 1H), 3.57 (q, J = 6.6 Hz, 1H), 3.11 (d, J = 8.2 Hz, 1H), 2.69-2.55 (m, 1H), 2.18-2.04 (m, 1H), 1.91-1.59 (m, 5H), 1.48-1.32 (m, 1H), 1.33-1.10 (m, 3H), 1.08-0.86 (m, 2H). |
| 88 | 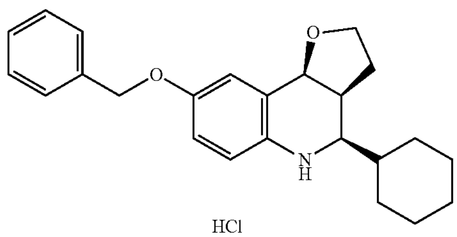 [SMILES: c1ccc(COc2ccc3c(c2)[C@H]2OCC[C@H]2[C@@H](C2CCCCC2)N3)cc1 ; Cl] | (3aSR*,4RS*,9bSR*)-8-(benzyloxy)-4-cyclohexyl-2,3,3a,4,5,9b-hexahydrofuro[3,2-c]quinoline hydrochloride | $^1$H NMR (CD$_3$OD) δ ppm: 7.49-7.28 (m, 5H), 7.22 (d, J = 8.9 Hz, 1H), 7.17 (d, J = 2.6 Hz, 1H), 7.06 (dd, J = 8.7, 2.5 Hz, 1H), 5.13 (s, 2H), 5.11 (d, J = 8.5 Hz, 1H), 3.90 (q, J = 8.0 Hz, 1H), 3.70 (td, J = 8.5, 2.9 Hz, 1H), 3.64-3.48 (m, 1H), 3.13-2.92 (m, 1H), 2.25-2.07 (m, 1H), 2.08-1.95 (m, 2H), 1.96-1.83 (m, 2H), 1.84-1.64 (m, 3H), 1.50-1.02 (m, 5H) |
| 89 | 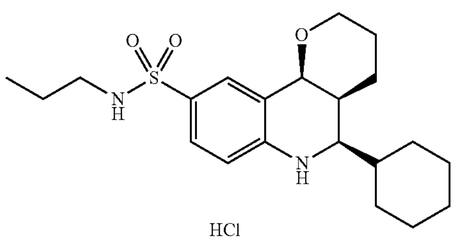 [SMILES: CCCNS(=O)(=O)c1ccc2c(c1)[C@H]1OCCC[C@H]1[C@@H](C1CCCCC1)N2 ; Cl] | (4aSR*,5RS*,10bSR*)-5-cyclohexyl-N-propyl-3,4,4a,5,6,10b-hexahydro-2H-pyrano[3,2-c]quinoline-9-sulfonamide | $^1$H NMR (CDCl$_3$) δ ppm: 7.81 (s, 1H), 7.50 (dd, J = 8.5, 2.2 Hz, 1H), 6.48 (d, J = 8.5 Hz, 1H), 4.99 (d, J = 5.5 Hz, 1H), 4.24 (s, 1H), 4.18 (t, J = 6.3 Hz, 1H), 3.63 (dd, J = 11.3, 4.5 Hz, 1H), 3.37 (td, J = 12.1, 2.2 Hz, 1H), 3.05 (dd, J = 9.7, 1.9 Hz, 1H), 2.90 (dd, J = 13.6, 6.9 Hz, 2H), 2.31-2.15 (m, 1H), 1.96-1.58 (m, 7H), 1.54-1.39 (m, 4H), 1.37-1.15 (m, 4H), 1.07-0.91 (m, 2H), 0.88 (t, J = 7.4 Hz, 3H). |
| 90 | 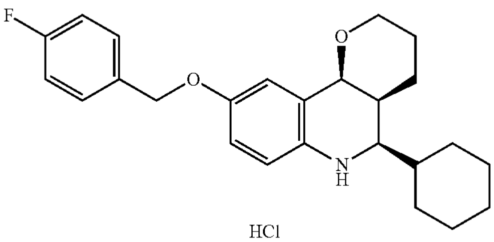 [SMILES: Fc1ccc(COc2ccc3c(c2)[C@H]2OCCC[C@H]2[C@@H](C2CCCCC2)N3)cc1 ; Cl] | (4aSR*,5RS*,10bSR*)-5-cyclohexyl-9-(4-fluoro-benzyloxy)-3,4,4a,5,6,10b-hexahydro-2H-pyrano[3,2-c]quinoline hydrochloride | $^1$H NMR (DMSO) δ ppm: 7.48 (dd, J = 8.4, 5.7 Hz, 2H), 7.21 (t, J = 8.9 Hz, 2H), 7.12-6.80 (m, 3H), 5.06 (s, 2H), 4.93 (d, J = 5.2 Hz, 1H), 3.51-3.24 (m, 1H), 3.21-3.00 (m, 2H), 2.35-2.16 (m, 1H), 2.10 (d, J = 12.1 Hz, 1H), 1.88-1.69 (m, 3H), 1.69-1.49 (m, 4H), 1.49-1.39 (m, 1H), 1.33-1.05 (m, 4H), 1.04-0.86 (m, 2H). |
| 91 | 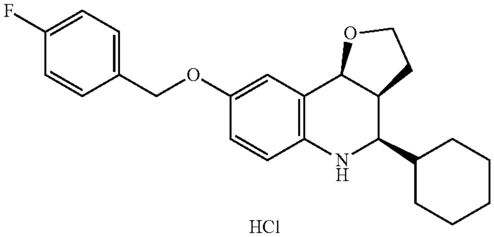 [SMILES: Fc1ccc(COc2ccc3c(c2)[C@H]2OCC[C@H]2[C@@H](C2CCCCC2)N3)cc1 ; Cl] | (3aSR*,4RS*,9bSR*)-4-cyclohexyl-8-(4-fluoro-benzyloxy)-2,3,3a,4,5,9b-hexahydrofuro[3,2-c]quinoline hydrochloride | $^1$H NMR (DMSO) δ ppm: 7.47 (dd, J = 8.3, 5.8 Hz, 2H), 7.20 (t, J = 8.8 Hz, 2H), 7.06-6.74 (m, 3H), 5.00 (s, 2H), 4.99 (d, J = 8.9 Hz, 1H), 3.67-3.47 (m, 2H), 3.31-3.15 (m, 1H), 2.82-2.60 (m, 1H), 2.08 (d, J = 11.7 Hz, 1H), 1.96-1.44 (m, 7H), 1.36-0.85 (m, 5H). |
| 92 | 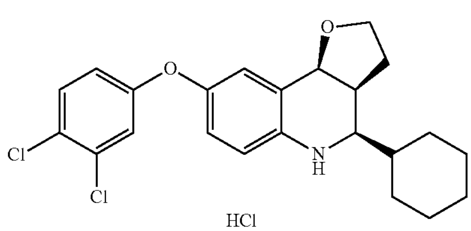 [SMILES: Clc1ccc(Oc2ccc3c(c2)[C@H]2OCC[C@H]2[C@@H](C2CCCCC2)N3)cc1Cl ; Cl] | (3aSR*,4RS*,9bSR*)-4-cyclohexyl-8-(3,4-dichloro-phenoxy)-2,3,3a,4,5,9b-hexahydrofuro[3,2-c]quinoline hydrochloride | $^1$H NMR (CDCl$_3$) δ ppm: 8.11 (d, J = 8.7 Hz, 1H), 7.40 (d, J = 8.8 Hz, 1H), 7.12 (d, J = 2.6 Hz, 1H), 7.10 (d, J = 2.8 Hz, 1H), 6.93 (dd, J = 8.7, 2.6 Hz, 1H), 6.85 (dd, J = 8.8, 2.8 Hz, 1H), 5.03 (d, J = 7.6 Hz, 1H), 3.97-3.70 (m, 2H), 3.51 (d, J = 6.0 Hz, 1H), 2.93 (q, J = 8.1 Hz, 1H), 2.58-2.45 (m, 1H), 2.43-2.26 (m, 1H), 2.27-2.00 (m, 3H), 1.91-1.76 (m, 2H), 1.76-1.66 (m, 1H), 1.45-1.02 (m, 6H). |

| ex. | structure | chemical name | NMR |
|---|---|---|---|
| 93 | HCl | (4aSR*,5RS*,10bSR*)-5-cyclohexyl-9-(3,4-dichlorophenoxy)-3,4,4a,5,6,10b-hexahydro-2H-pyrano[3,2-c]quinoline hydrochloride | $^1$H NMR (CDCl$_3$) δ ppm: 8.09 (d, J = 8.6 Hz, 1H), 7.40 (d, J = 8.8 Hz, 1H), 7.21 (s, 1H), 7.11 (d, J = 2.3 Hz, 1H), 6.95 (d, J = 8.3 Hz, 1H), 6.85 (dd, J = 8.8, 2.3 Hz, 1H), 4.89 (d, J = 5.1 Hz, 1H), 3.63 (d, J = 10.4 Hz, 1H), 3.34-3.16 (m, 2H), 2.73-2.46 (m, 2H), 2.34-2.18 (m, 1H), 1.95-1.45 (m, 8H), 1.46-1.13 (m, 4H), 1.13-0.90 (m, 1H). |
| 94 | HCl | (3aSR*,4RS*,9bSR*)-ethyl 4-cyclohexyl-2,3,3a,4,5,9b-hexahydrofuro[3,2-c]quinoline-8-carboxylate hydrochloride | $^1$H NMR (CDCl$_3$) δ ppm: 8.08 (s, 1H), 7.88-7.75 (m, 1H), 7.17-7.02 (m, 1H), 5.11 (d, J = 7.6 Hz, 1H), 4.33 (q, J = 7.1 Hz, 2H), 3.94-3.63 (m, 2H), 3.33 (d, J = 4.0 Hz, 1H), 2.92-2.75 (m, 1H), 2.27-1.63 (m, 8H), 1.47 (t, J = 7.1 Hz, 1H), 1.37 (t, J = 7.1 Hz, 3H), 1.34-0.94 (m, 4H). |
| 95 | HCl | (3aSR*,4RS*,9bSR*)-8-pentyl-4-(tetrahydro-2H-thiopyran-4-yl)-2,3,3a,4,5,9b-hexahydrofuro[3,2-c]quinoline hydrochloride | $^1$H NMR (CDCl$_3$) δ ppm: 7.68 (d, J = 7.8 Hz, 1H), 7.31 (d, J = 1.5 Hz, 1H), 7.07 (dd, J = 8.2, 1.6 Hz, 1H), 5.11 (d, J = 7.7 Hz, 1H), 3.87 (q, J = 7.6 Hz, 1H), 3.75 (td, J = 8.7, 4.6 Hz, 1H), 3.50 (dd, J = 6.7, 2.0 Hz, 1H), 2.96-2.63 (m, 5H), 2.63-2.45 (m, 4H), 2.43-2.17 (m, 2H), 2.14-1.97 (m, 1H), 1.81-1.48 (m, 4H), 1.41-1.20 (m, 4H), 0.90 (t, J = 6.8 Hz, 3H). |
| 96 | HCl | (3aSR*,4RS*,9bSR*)-8-(2-chlorophenoxy)-4-cyclohexyl-2,3,3a,4,5,9b-hexahydrofuro[3,2-c]quinoline hydrochloride | $^1$H NMR (CDCl$_3$) δ ppm: 7.89-7.70 (m, 1H), 7.45 (d, J = 7.9 Hz, 1H), 7.21 (d, J = 7.6 Hz, 1H), 7.10 (t, J = 7.6 Hz, 1H), 7.01 (d, J = 2.6 Hz, 1H), 6.98 (d, J = 8.2 Hz, 1H), 6.84 (dd, J = 8.7, 2.5 Hz, 1H), 5.01 (d, J = 7.6 Hz, 1H), 3.95-3.66 (m, 2H), 3.43 (d, J = 7.1 Hz, 1H), 2.87 (q, J = 8.2 Hz, 1H), 2.40 (d, J = 11.4 Hz, 1H), 2.35-2.20 (m, 1H), 2.12-1.94 (m, 3H), 1.89-1.74 (m, 2H), 1.75-1.63 (m, 1H), 1.45-0.92 (m, 5H). |
| 97 | HCl | (3aSR*,4RS*,9bSR*)-4-cyclohexyl-N-phenyl-2,3,3a,4,5,9b-hexahydrofuro[3,2-c]quinolin-8-amine hydrochloride | $^1$H NMR (CDCl$_3$) δ ppm: 7.90-7.72 (m, 1H), 7.30-7.21 (m, 2H), 7.17 (s, 1H), 7.08 (d, J = 7.6 Hz, 2H), 6.98 (d, J = 7.3 Hz, 1H), 6.93 (d, J = 8.2 Hz, 1H), 4.98 (d, J = 7.5 Hz, 1H), 3.91-3.67 (m, 2H), 3.38 (d, J = 7.0 Hz, 1H), 2.95-2.77 (m, 1H), 2.51-2.25 (m, 2H), 2.14-1.95 (m, 3H), 1.90-1.74 (m, 2H), 1.74-1.64 (m, 1H), 1.44-0.95 (m, 5H). |
| 98 | HCl | (4aSR*,5RS*,10bSR*)-5-cyclohexyl-9-ethoxy-3,4,4a,5,6,10b-hexahydro-2H-pyrano[3,2-c]quinoline hydrochloride | $^1$H NMR (CDCl$_3$) δ ppm: 7.99 (d, J = 8.7 Hz, 1H), 7.07 (d, J = 2.6 Hz, 1H), 6.85 (dd, J = 8.9, 2.8 Hz, 1H), 4.88 (d, J = 5.2 Hz, 1H), 4.03 (q, J = 7.0 Hz, 2H), 3.65 (d, J = 10.9 Hz, 1H), 3.35 (t, J = 10.8 Hz, 1H), 3.22 (d, J = 9.7 Hz, 1H), 2.71 (d, J = 12.5 Hz, 1H), 2.59-2.40 (m, 1H), 2.40-2.19 (m, 1H), 1.99-1.50 (m, 9H), 1.42 (t, J = 7.0 Hz, 3H), 1.39-1.14 (m, 3H), 1.14-0.89 (m, 1H). |

| ex. | structure | chemical name | NMR |
|---|---|---|---|
| 99 | 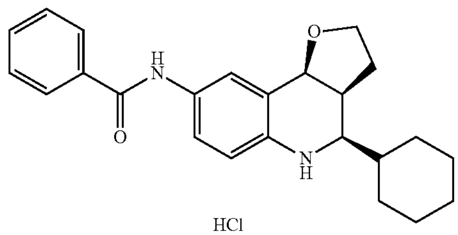 [SMILES: O=C(Nc1ccc2c(c1)[C@H]1OCC[C@H]1[C@@H](C1CCCCC1)N2)c1ccccc1 ; Cl] | N-((3aSR*,4RS*,9bSR*)-4-cyclohexyl-2,3,3a,4,5,9b-hexahydrofuro[3,2-c]quinolin-8-yl)benzamide hydrochloride | ¹H NMR (DMSO) δ ppm: 9.99 (s, 1H), 7.93 (d, J = 7.0 Hz, 2H), 7.62-7.46 (m, 4H), 7.43 (d, J = 8.2 Hz, 1H), 6.80 (d, J = 8.5 Hz, 1H), 5.01 (d, J = 7.8 Hz, 1H), 3.81-3.56 (m, 2H), 3.15 (d, J = 7.5 Hz, 1H), 2.72-2.57 (m, 1H), 2.18-2.04 (m, 1H), 1.95-1.54 (m, 6H), 1.52-1.34 (m, 1H), 1.34-1.10 (m, 3H), 1.10-0.87 (m, 2H). |
| 100 | 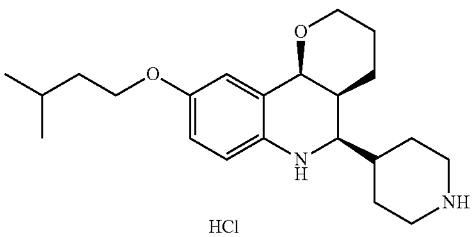 [SMILES: CC(C)CCOc1ccc2c(c1)[C@H]1OCCC[C@H]1[C@@H](C1CCNCC1)N2 ; Cl] | (4aSR*,5RS*,10bSR*)-9-(isopentyloxy)-5-(piperidin-4-yl)-3,4,4a,5,6,10b-hexahydro-2H-pyrano[3,2-c]quinoline hydrochloride | ¹H NMR (CDCl₃) δ ppm: 9.86-9.57 (m, 1H), 9.57-9.25 (m, 1H), 6.97 (s, 1H), 6.85-6.42 (m, 2H), 4.97 (d, J = 5.2 Hz, 1H), 3.92 (t, J = 6.7 Hz, 2H), 3.79-3.65 (m, 1H), 3.66-3.50 (m, 2H), 3.39 (t, J = 11.5 Hz, 1H), 3.14 (d, J = 7.2 Hz, 1H), 3.03-2.83 (m, 2H), 2.30-2.13 (m, 2H), 2.05-1.93 (m, 2H), 1.91-1.70 (m, 4H), 1.70-1.59 (m, 4H), 1.59-1.38 (m, 3H), 0.95 (d, J = 6.6 Hz, 6H). |
| 101 | 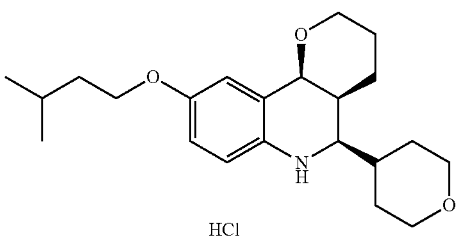 [SMILES: CC(C)CCOc1ccc2c(c1)[C@H]1OCCC[C@H]1[C@@H](C1CCOCC1)N2 ; Cl] | (4aSR*,5RS*,10bSR*)-9-(isopentyloxy)-5-(tetrahydro-2H-pyran-4-yl)-3,4,4a,5,6,10b-hexahydro-2H-pyrano[3,2-c]quinoline hydrochloride | ¹H NMR (DMSO) δ ppm: 7.05 (d, J = 8.3 Hz, 1H), 6.88 (s, 1H), 6.87 (d, J = 8.3 Hz, 1H), 4.95 (d, J = 5.3 Hz, 1H), 4.05-3.82 (m, 4H), 3.56 (d, J = 9.5 Hz, 1H), 3.42-3.09 (m, 4H), 2.33-2.20 (m, 1H), 2.07-1.86 (m, 2H), 1.83-1.71 (m, 1H), 1.70-1.40 (m, 6H), 1.36-1.09 (m, 3H), 0.92 (d, J = 6.6 Hz, 6H). |
| 102 | 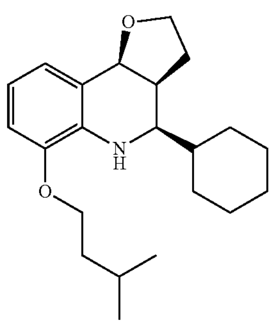 [SMILES: CC(C)CCOc1cccc2c1N[C@H](C1CCCCC1)[C@@H]1CCO[C@H]21] | (3aSR*,4RS*,9bSR*)-4-cyclohexyl-6-(isopentyloxy)-2,3,3a,4,5,9b-hexahydrofuro[3,2-c]quinoline | ¹H NMR (CDCl₃) δ ppm: 6.92 (dd, J = 6.8, 1.9 Hz, 1H), 6.73-6.60 (m, 2H), 5.14 (d, J = 8.0 Hz, 1H), 4.36 (s, 1H), 4.11-3.90 (m, 2H), 3.84-3.72 (m, 2H), 3.05 (dd, J = 9.1, 2.2 Hz, 1H), 2.74 (q, J = 8.6 Hz, 1H), 2.15-1.60 (m, 10H), 1.53-1.40 (m, 1H), 1.39-1.12 (m, 3H), 1.11-0.84 (m, 2H), 0.97 (dd, J = 6.0, 4.4 Hz, 6H). |
| 103 | 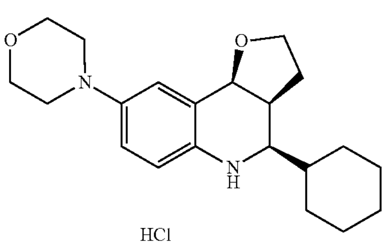 [SMILES: c1cc2c(cc1N1CCOCC1)[C@H]1OCC[C@H]1[C@@H](C1CCCCC1)N2 ; Cl] | (3aSR*,4RS*,9bSR*)-4-cyclohexyl-8-morpholino-2,3,3a,4,5,9b-hexahydrofuro[3,2-c]quinoline hydrochloride | ¹H NMR (CD₃OD) δ ppm: 6.58 (d, J = 2.7 Hz, 1H), 6.44 (dd, J = 8.9, 2.8 Hz, 1H), 6.08 (d, J = 8.9 Hz, 1H), 4.28 (d, J = 7.7 Hz, 1H), 3.26-3.17 (m, 4H), 3.03 (q, J = 8.2 Hz, 1H), 2.91 (td, J = 8.6, 3.8 Hz, 1H), 2.82-2.69 (m, 4H), 2.45 (dd, J = 8.7, 2.6 Hz, 1H), 2.07-1.90 (m, 1H), 1.37-1.23 (m, 1H), 1.21-0.97 (m, 5H), 0.96-0.84 (m, 1H), 0.77-0.62 (m, 1H), 0.64-0.36 (m, 3H), 0.38-0.18 (m, 2H). |
| 104 | 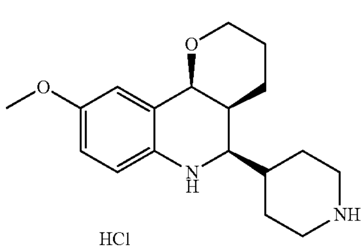 [SMILES: COc1ccc2c(c1)[C@H]1OCCC[C@H]1[C@@H](C1CCNCC1)N2 ; Cl] | (4aSR*,5RS*,10bSR*)-9-methoxy-5-(piperidin-4-yl)-3,4,4a,5,6,10b-hexahydro-2H-pyrano[3,2-c]quinoline hydrochloride | ¹H NMR (CD₃OD) δ ppm: 7.31 (d, J = 8.8 Hz, 1H), 7.16 (d, J = 2.2 Hz, 1H), 7.03 (dd, J = 8.8, 2.6 Hz, 1H), 5.05 (d, J = 4.6 Hz, 1H), 3.85 (s, 3H), 3.69 (dd, J = 11.0, 3.7 Hz, 1H), 3.63-3.42 (m, 3H), 3.36 (d, J = 2.4 Hz, 1H), 3.19-3.02 (m, 2H), 2.66-2.48 (m, 1H), 2.36-2.08 (m, 3H), 1.94-1.51 (m, 5H), 1.25 (qd, J = 12.8, 3.8 Hz, 1H). |

| ex. | structure | chemical name | NMR |
|---|---|---|---|
| 105 | 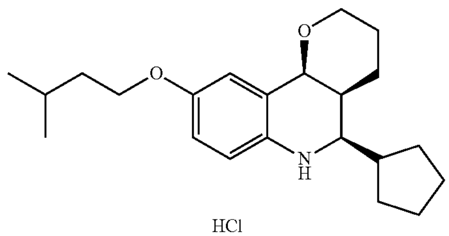 [SMILES: CC(C)CCOc1ccc2c(c1)[C@H]1OCCC[C@H]1[C@@H](C1CCCC1)N2 ; Cl] | (4aSR*,5RS*,10bSR*)-5-cyclopentyl-9-(isopentyloxy)-3,4,4a,5,6,10b-hexahydro-2H-pyrano[3,2-c]quinoline hydrochloride | ¹H NMR (CD₃OD) δ ppm: 7.27 (d, J = 8.9 Hz, 1H), 7.17 (d, J = 2.8 Hz, 1H), 7.03 (dd, J = 8.8, 2.7 Hz, 1H), 5.05 (d, J = 4.3 Hz, 1H), 4.07 (t, J = 6.1 Hz, 2H), 3.69 (dd, J = 11.7, 4.6 Hz, 1H), 3.46-3.38 (m, 1H), 3.34-3.31 (m, 1H), 2.56-2.43 (m, 1H), 2.33-2.19 (m, 1H), 2.08-1.92 (m, 2H), 1.93-1.64 (m, 9H), 1.65-1.55 (m, 1H), 1.51-1.31 (m, 2H), 1.19 (qd, J = 12.8, 3.7 Hz, 1H), 0.98 (d, J = 6.6 Hz, 6H). |
| 106 | 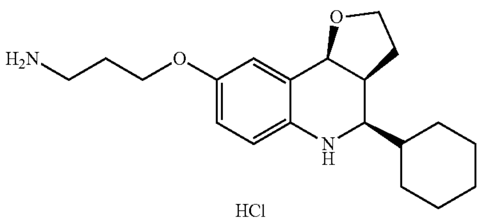 [SMILES: NCCCOc1ccc2c(c1)[C@H]1OCC[C@H]1[C@@H](C1CCCCC1)N2 ; Cl] | 3-((3aSR*,4RS*,9bSR*)-4-cyclohexyl-2,3,3a,4,5,9b-hexahydrofuro[3,2-c]quinolin-8-yloxy)propan-1-amine hydrochloride | ¹H NMR (CD₃OD) δ ppm: 7.20 (d, J = 8.8 Hz, 1H), 7.09 (d, J = 2.7 Hz, 1H), 7.00 (dd, J = 8.8, 2.8 Hz, 1H), 5.12 (d, J = 7.6 Hz, 1H), 4.14 (t, J = 5.8 Hz, 2H), 3.90 (dd, J = 15.9, 8.2 Hz, 1H), 1.47-1.05 (m, 5H), 3.71 (td, J = 8.7, 3.6 Hz, 1H), 3.53 (d, J = 6.8 Hz, 1H), 3.16 (t, J = 7.3 Hz, 2H), 3.10-2.90 (m, 1H), 2.22-1.64 (m, 10H). |
| 107 | 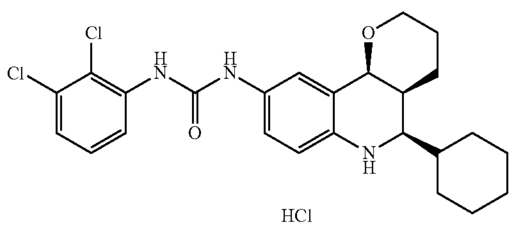 [SMILES: O=C(Nc1ccc2c(c1)[C@H]1OCCC[C@H]1[C@@H](C1CCCCC1)N2)Nc1cccc(Cl)c1Cl ; Cl] | 1-((4aSR*,5RS*,10bSR*)-5-cyclohexyl-3,4,4a,5,6,10b-hexahydro-2H-pyrano[3,2-c]quinolin-9-yl)-3-(2,3-dichlorophenyl)urea hydrochloride | ¹H NMR (DMSO) δ ppm: 9.46 (s, 1H), 8.40 (s, 1H), 8.17 (dd, J = 7.9, 1.9 Hz, 1H), 7.40 (s, 1H), 7.35-7.17 (m, 3H), 6.89 (s, 1H), 4.94 (d, J = 5.3 Hz, 1H), 3.25 (t, J = 10.8 Hz, 2H), 3.07 (d, J = 7.5 Hz, 1H), 2.26-2.04 (m, 2H), 1.87-1.69 (m, 3H), 1.69-1.38 (m, 5H), 1.34-1.09 (m, 4H), 1.05-0.83 (m, 2H). |
| 108 | 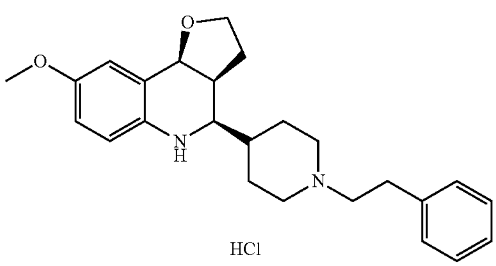 [SMILES: COc1ccc2c(c1)[C@H]1OCC[C@H]1[C@@H](C1CCN(CCc3ccccc3)CC1)N2 ; Cl] | (4aSR*,5RS*,10bSR*)-9-methoxy-5-(1-phenethyl-piperidin-4-yl)-3,4,4a,5,6,10b-hexahydro-2H-pyrano[3,2-c]quinoline hydrochloride | ¹H NMR (CD₃OD) δ ppm: 7.41-7.24 (m, 5H), 7.16 (d, J = 9.2 Hz, 1H), 7.12 (d, J = 1.7 Hz, 1H), 6.97 (dd, J = 9.2, 1.9 Hz, 1H), 5.05 (d, J = 4.2 Hz, 1H), 3.83 (s, 3H), 3.85-3.72 (m, 1H), 3.68 (dd, J = 11.8, 4.6 Hz, 1H), 3.45-3.22 (m, 5H), 3.20-3.04 (m, 4H), 2.58-2.41 (m, 1H), 2.39-2.08 (m, 3H), 1.90-1.54 (m, 5H), 1.39-1.17 (m, 1H). |
| 109 | 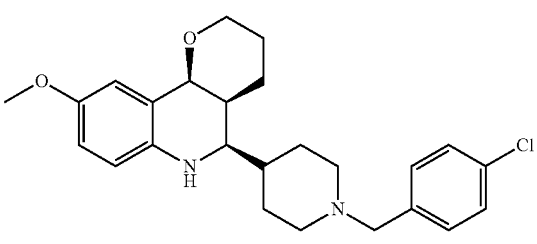 | (4aSR*,5RS*,10bSR*)-5-(1-(4-chlorobenzyl)piperidin-4-yl)-9-methoxy-3,4,4a,5,6,10b-hexahydro-2H-pyrano[3,2-c]quinoline hydrochloride | ¹H NMR (CD₃OD) δ ppm: 7.59-7.49 (m, 4H), 7.04 (d, J = 2.1 Hz, 1H), 6.99 (d, J = 8.7 Hz, 1H), 6.88 (dd, J = 9.1, 2.1 Hz, 1H), 5.01 (d, J = 5.3 Hz, 1H), 4.34 (s, 2H), 3.79 (s, 3H), 3.71-3.51 (m, 4H), 3.30-3.18 (m, 1H), 3.16-2.96 (m, 2H), 2.45-2.24 (m, 2H), 2.23-2.10 (m, 1H), 2.09-1.91 (m, 1H), 1.85-1.67 (m, 2H), 1.67-1.47 (m, 3H), 1.42-1.24 (m, 1H). |

| ex. | structure | chemical name | NMR |
|---|---|---|---|
| 110 | 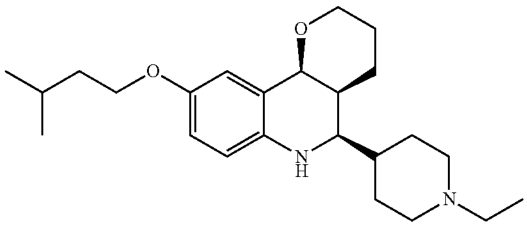 | (4aSR*,5RS*,10bSR*)-5-(1-ethylpiperidin-4-yl)-9-(isopentyloxy)-3,4,4a,5,6,10b-hexahydro-2H-pyrano[3,2-c]quinoline hydrochloride | $^1$H NMR (CDCl$_3$) δ ppm: 6.95 (d, J = 2.5 Hz, 1H), 6.68 (dd, J = 8.6, 2.6 Hz, 1H), 6.50 (d, J = 8.7 Hz, 1H), 5.00 (d, J = 5.4 Hz, 1H), 3.92 (t, J = 6.7 Hz, 2H), 3.75-3.51 (m, 3H), 3.42 (t, J = 11.2 Hz, 1H), 3.13 (d, J = 9.6 Hz, 1H), 3.05 (q, J = 7.2 Hz, 2H), 2.70-2.46 (m, 2H), 2.27-2.02 (m, 4H), 2.01-1.89 (m, 1H), 1.89-1.59 (m, 5H), 1.49 (t, J = 7.4 Hz, 3H), 1.56-1.40 (m, 3H), 0.95 (d, J = 6.6 Hz, 6H). |
| 111 | 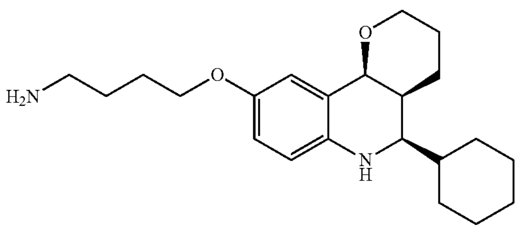 | 4-((4aSR*,5RS*,10bSR*)-5-cyclohexyl-3,4,4a,5,6,10b-hexahydro-2H-pyrano[3,2-c]quinolin-9-yloxy)butan-1-amine hydrochloride | $^1$H NMR (cdcl$_3$) δ ppm: 11.24-10.43 (m, 2H), 8.57-7.95 (m, 1H), 7.84-7.40 (m, 1H), 7.12-6.72 (m, 1H), 5.08-4.75 (m, 1H), 4.18-3.77 (m, 2H), 3.76-3.40 (m, 1H), 3.42-3.17 (m, 2H), 3.17-2.86 (m, 1H), 2.67-0.84 (m, 45H). |
| 112 | 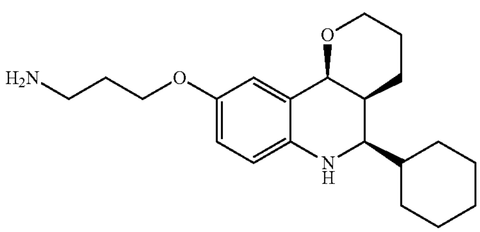 | 3-((4aSR*,5RS*,10bSR*)-5-cyclohexyl-3,4,4a,5,6,10b-hexahydro-2H-pyrano[3,2-c]quinolin-9-yloxy)propan-1-amine hydrochloride | $^1$H NMR (CD$_3$OD) δ ppm: 7.32 (d, J = 8.8 Hz, 1H), 7.20 (s, 1H), 7.08 (dd, J = 8.9, 2.4 Hz, 1H), 5.03 (d, J = 4.0 Hz, 1H), 4.27-4.10 (m, 2H), 3.92 (t, J = 7.0 Hz, 1H), 3.68 (dd, J = 12.1, 3.7 Hz, 1H), 3.31-3.23 (m, 1H), 3.17 (t, J = 7.2 Hz, 2H), 2.66-2.41 (m, 2H), 2.33-2.08 (m, 2H), 2.09-1.65 (m, 8H), 1.66-1.50 (m, 1H), 1.48-1.01 (m, 5H). |
| 113 | 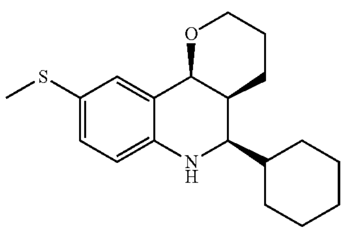 | (4aSR*,5RS*,10bSR*)-5-cyclohexyl-9-(methylthio)-3,4,4a,5,6,10b-hexahydro-2H-pyrano[3,2-c]quinoline hydrochloride | $^1$H NMR (CDCl$_3$) δ ppm: 7.84 (d, J = 6.9 Hz, 1H), 7.44 (s, 1H), 7.18 (d, J = 6.4 Hz, 1H), 4.90 (d, J = 3.5 Hz, 1H), 3.65 (d, J = 11.1 Hz, 1H), 3.32 (t, J = 11.2 Hz, 1H), 3.21 (d, J = 8.2 Hz, 1H), 2.48 (s, 3H), 2.63-2.43 (m, 2H), 2.28-2.08 (m, 1H), 1.96-1.45 (m, 9H), 1.45-1.12 (m, 4H), 1.12-0.85 (m, 1H). |

EXAMPLE 114

Preparation of (4aS,5R,10bS)-9-(isopentyloxy)-5-(tetrahydro-2H-pyran-4-yl)-3,4,4a,5,6,10b-hexahydro-2H-pyrano[3,2-c]quinoline

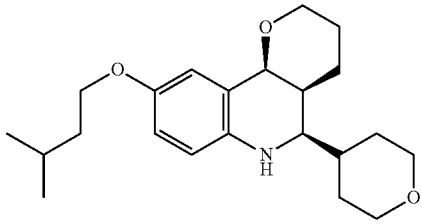 [SMILES: CC(C)CCOc1ccc2c(c1)[C@H]1OCCC[C@H]1[C@@H](C1CCOCC1)N2]

Starting from example 101, a chiral HPLC separation ($t_r$ 80 min, 98/2 Heptane/EtOH v/v 10 ml/min, Chiralpak AD-H 2*25 cm, 5 μm, Daicel) was carried out obtaining example 114.

$^1$H NMR (CD$_3$OD) δ ppm: 6.85 (d, J=2.7 Hz, 1H), 6.65 (dd, J=8.8, 2.7 Hz, 1H), 6.60 (d, J=8.7 Hz, 1H), 4.97 (d, J=5.6 Hz, 1H), 4.05-3.95 (m, 2H), 3.91 (t, J=6.6 Hz, 2H), 3.60-3.52 (m, 1H), 3.50-3.36 (m, 3H), 2.91 (dd, J=9.5, 1.9 Hz, 1H), 2.20-2.09 (m, 1H), 1.99-1.91 (m, 1H), 1.82 (dp, J=13.3, 6.7 Hz, 1H), 1.75-1.65 (m, 3H), 1.65-1.57 (m, 3H), 1.56-1.46 (m, 1H), 1.43 (dd, J=12.7, 3.7 Hz, 1H), 1.39-1.23 (m, 2H), 0.96 (d, J=6.7 Hz, 6H).

Preparation of Compounds of Formula (Ie)

EXAMPLE 115

Synthesis of (4aSR*,5RS*,10bSR*)-5-cyclohexyl-9-(isopentyloxy)-6-methyl-3,4,4a,5,6,10b-hexahydro-2H-pyrano[3,2-c]quinoline

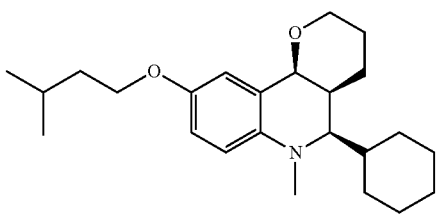 [SMILES: CC(C)CCOc1ccc2c(c1)[C@H]1OCCC[C@H]1[C@@H](C1CCCCC1)N2C]

To a microwave vial was added sequentially (4aSR*,5RS*,10bSR*)-5-cyclohexyl-9-(isopentyloxy)-3,4,4a,5,6,10b-hexahydro-2H-pyrano[3,2-c]quinoline (base of example 27) (200 mg, 0.56 mmol, 1 equiv.), methanol (2.5 mL) and NaBH(OAc)$_3$ (237 mg, 1.12 mmol, 2 equiv.). The microwave vial was capped with a septum and formaldehyde (43 μL, 1.4 mmol, 2.5 equiv.) was added via syringe. The reaction mixture was heated under microwave heating at 120° C. for 10 min. The solvent was evaporated under reduced pressure and the crude taken up in CH$_2$Cl$_2$ and washed with sat. NaHCO$_3$ solution. The combined organic fractions were dried over MgSO$_4$ and the solvent removed under reduced pressure after filtration. The residue was purified by Combiflash column chromatography (SiO$_2$, c-Hexane/AcOEt) to afford (4aSR*,5RS*,10bSR*)-5-cyclohexyl-9-(isopentyloxy)-6-methyl-3,4,4a,5,6,10b-hexahydro-2H-pyrano[3,2-c]quinoline (32 mg, 15%) as white solid.

$^1$H NMR (CDCl3) δ ppm: 6.96 (d, J=2.8 Hz, 1H), 6.76 (dd, J=8.9, 2.9 Hz, 1H), 6.69 (d, J=8.9 Hz, 1H), 4.87 (d, J=5.5 Hz, 1H), 3.93 (t, J=6.7 Hz, 2H), 3.65-3.43 (m, 2H), 2.87 (s, 3H), 2.89-2.81 (m, 1H), 2.30-2.15 (m, 1H), 1.92-1.59 (m, 10H), 1.53-1.40 (m, 1H), 1.34-1.03 (m, 6H), 0.95 (d, J=6.6 Hz, 6H), 0.99-0.78 (m, 1H).

Preparation of Compounds of Formula (Id)

EXAMPLE 116

Synthesis of (4aSR*,5RS*,10bSR*)-9-tert-butyl-5-cyclopropyl-6-ethyl-3,4,4a,5,6,10b-hexahydro-2H-pyrano[3,2-c]quinoline

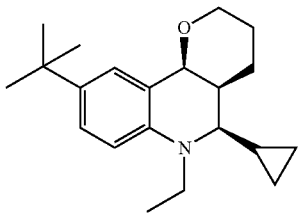 [SMILES: CCN1c2ccc(C(C)(C)C)cc2[C@H]2OCCC[C@H]2[C@H]1C1CC1]

To a stirred solution of 1-((4aSR*,5RS*,10bSR*)-9-tert-butyl-5-cyclopropyl-3,4,4a,5-tetrahydro-2H-pyrano[3,2-c]quinolin-6(10bH)-yl)ethanone (230 mg, 0.702 mmol, 1 equiv.) in dry thf (10 mL) under argon atmosphere was added via syringe LiAlH$_4$ solution (1 M in THF, 1.40 mL, 1.405 mmol, 2 equiv.) dropwise at 0° C. under argon. The reaction was allowed to reach r.t. and then heated at 65° C. overnight. After cooling back to r.t., the reaction mixture was quenched by the addition of sat. sodium tartrate solution and extracted with AcOEt twice. The combined organic fractions were dried over MgSO$_4$ and the solvent removed under reduced pressure after filtration to give (4aSR*,5RS*,10bSR*)-9-tert-butyl-5-cyclopropyl-6-ethyl-3,4,4a,5,6,10b-hexahydro-2H-pyrano[3,2-c]quinoline (13 mg, 6%) as colourless oil.

$^1$H NMR (CDC$_3$) δ ppm: 7.41 (d, J=1.4 Hz, 1H), 7.15 (dd, J=8.6, 2.2 Hz, 1H), 6.62 (d, J=8.7 Hz, 1H), 4.95 (d, J=5.5 Hz, 1H), 3.76-3.54 (m, 3H), 3.48 (td, J=11.4, 2.1 Hz, 1H), 2.42 (dd, J=9.5, 2.3 Hz, 1H), 2.28-2.11 (m, 1H), 1.93-1.78 (m, 1H), 1.77-1.61 (m, 1H), 1.29 (s, 9H), 1.08 (t, J=7.0 Hz, 3H), 1.02-0.92 (m, 1H), 0.92-0.72 (m, 3H), 0.69-0.51 (m, 1H), 0.50-0.36 (m, 1H), 0.25-0.10 (m, 1H).

Pharmacological Study

Brain membrane preparation and binding assays for the σ1-receptor were performed as described (DeHaven-Hudkins, D. L., L. C. Fleissner, and F. Y. Ford-Rice, 1992, Characterization of the binding of [$^3$H](+)pentazocine to a recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pretreated glass fiber filterplate (MultiScreen-FC, Millipore), with polyethylenimine 0.1%. The filters were washed two times with 200 µl of washing buffer (50 mM Tris Cl, pH=7.4) and then 25 µl of Ecoscint H liquid scintillation cocktail were added. Microplates were allowed to set for several hours and then quantified by liquid scintillation spectrophotometry (1450 Microbeta, Wallac). Nonspecific binding was determined with 1 µM haloperidol.

| Example | $K_i$ [nM] |
|---|---|
| 1 | 186.6 |
| 6 | 15.1 |
| 16 | 121.6 |
| 27 | 51.6 |
| 32 | 108.0 |
| 41 | 131.3 |
| 55 | 194.4 |
| 59 | 131.9 |
| 60 | 42.6 |
| 63 | 61.9 |
| 67 | 310.7 |
| 71 | 349.3 |
| 84 | 244.5 |
| 85 | 154.6 |
| 86 | 78.2 |
| 87 | 302.2 |
| 91 | 267.2 |
| 92 | 110.3 |
| 93 | 79.3 |
| 95 | 89.1 |
| 100 | 535.8 |
| 101 | 84.0 |
| 103 | 337.2 |
| 105 | 124.2 |
| 106 | 25.3 |
| 108 | 279.1 |
| 109 | 27.2 |
| 110 | 316.5 |
| 111 | 241.9 |
| 112 | 133.6 |
| 114 | 30.0 |

The invention claimed is:

1. A compound of the following general formula:

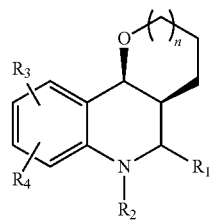

wherein $R_1$ is a saturated $C_{4-9}$ cycloalkyl optionally at least monosubstituted, optionally containing one heteroatom as a ring member selected from N, O or S, which may be condensed with an optionally at least monosubstituted mono polycyclic ring system;

$R_2$ is selected from the group consisting of hydrogen; a branched or unbranched, saturated or unsaturated, optionally at least mono-substituted, aliphatic radical $C_{1-10}$ or —$CH_2R_5$;

$R_3$ and $R_4$ are independently selected from the group consisting of hydrogen; —$NO_2$; —$CF_3$; —OH; —SH; —$NR_5R_6$; —CN; a branched or unbranched, saturated or unsaturated, optionally at least mono-substituted, aliphatic radical $C_{1-10}$; a saturated or unsaturated $C_{3-9}$ cycloalkyl optionally at least rnoriosubstituted, optionally at least containing one heteroatom as a ring member selected from N, O or S which may be condensed with an optionally at least monosubstituted mono or polycyclic ring system; a substituted or unsubstituted aryl; —NHC(O)NHR$_7$; —NHC(S)NHR$_7$; —C(O)OR$_8$; —OR$_9$; —NR$_{10}$C(O)R$_{11}$; —SR$_{12}$; —C(O)NR$_{13}$R$_{14}$; —SO$_2$NR$_{15}$R$_{16}$, or halogen;

$R_5$ to $R_{12}$ are independently selected from hydrogen; a branched or unbranched, saturated or unsaturated, optionally at least mono-substituted, aliphatic radical $C_{1-10}$; substituted or unsubstituted aryl; substituted or unsubstituted $C_{3-9}$ cycloalkyl optionally at least containing one heteroatom as a ring member selected from N, O or S which may be condensed with an optionally at least monosubstituted mono or polycyclic ring system; or substituted or unsubstituted heteroaryl which may be condensed with an optionally at least monosubstituted mono or polycyclic ring system;

$R_{13}$ to $R_{16}$ are independently selected from hydrogen; a branched or unbranched, saturated or unsaturated, optionally at least mono-substituted, aliphatic radical $C_{1-10}$; substituted or unsubstituted aryl; substituted or unsubstituted $C_{3-9}$ cycloalkyl optionally at least containing one heteroatom as a ring member selected from N, O or S which may be condensed with an optionally at least monosubstituted mono or polycyclic ring system; substituted or unsubstituted heteroaryl which may be condensed with an optionally at least monosubstituted mono or polycyclic ring system;

or $R_{13}$ to $R_{16}$ together with a bridging nitrogen form a $C_{3-9}$ cycloalkyl optionally containing at least one additional heteroatom as a ring member selected from N, O or S;

n is 0 or 1;

with the proviso that at least one of $R_3$ or $R_4$ is always different from hydrogen and with the proviso that when $R_1$ is cyclohexyl, unsubstituted tetrahydrofurane or substituted pyrrolidine, if $R_3$ or $R_4$ are in position 8 when n=0 or in position 9 when n=1, they are not tert-butyl, or a pharmaceutically acceptable salt or stereoisomer thereof.

2. A compound according to claim 1, wherein $R_1$ is adamantly or the following group:

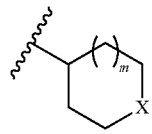

where X represents a —$CH_2$—, —O—, —$NR_{17}$— or —S— and m=0 or 1 being $R_{17}$ a $C_{1-6}$ alkyl, a benzyl or a hydrogen.

3. A compound according to claim 1, wherein $R_2$ is hydrogen or $C_{1-5}$alkyl.

4. A compound according to claim 1, wherein $R_3$ and $R_4$ are independently selected from the group consisting of hydrogen; halogen; —$NO_2$; —$CF_3$; —OH; —SH; —$NR_5R_6$; —CN; a substituted or unsubstituted, branched or unbranched $C_{1-6}$ alkyl; —NHC(O)NHR$_7$; —C(O)OR$_8$; —OR$_9$; —SR$_{12}$; —SO$_2$NR$_{15}$R$_{16}$ or a group selected from:

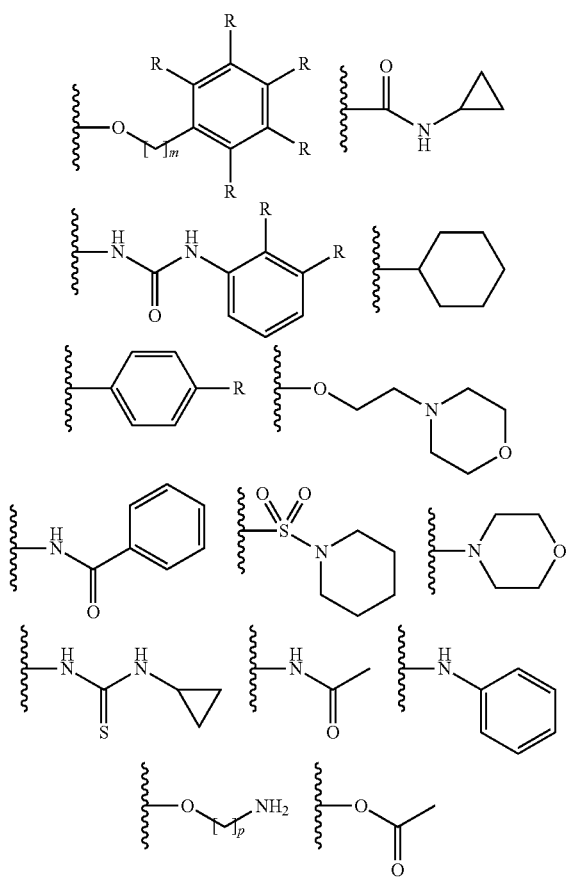

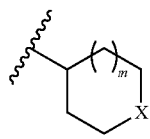

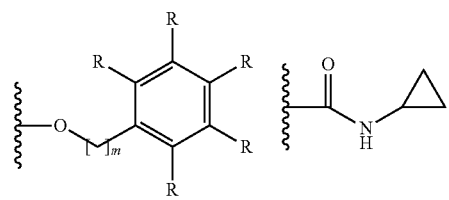

wherein R independently represents e hydrogen; substituted or unsubstituted, branched or unbranched $C_{1-6}$ alkyl, an OH or a halogen and wherein m=0 or 1 and p=3 or 4.

5. A compound according to claim 1, wherein $R_1$ is adamantyl or the following group:

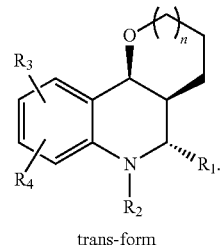

wherein X represents a —$CH_2$—, —O—, —$NR_{17}$— or —S— and m=0 or 1 being $R_{17}$ a $C_{1-6}$ alkyl or a hydrogen;

$R_2$ is hydrogen or $C_{1-6}$ alkyl;

$R_3$ and $R_4$ are independently selected from the group consisting of hydrogen; halogen; —$NO_2$; —$CF_3$; —OH; —SH; —$NR_5R_8$; —CN; a substituted or unsubstituted, branched or unbranched $C_{1-6}$ alkyl; —NHC(O)NH$R_7$; —C(O)O $R_8$; —$OR_9$; —$SR_{12}$; —$SO_2NR_{15}R_{16}$ or a group selected from:

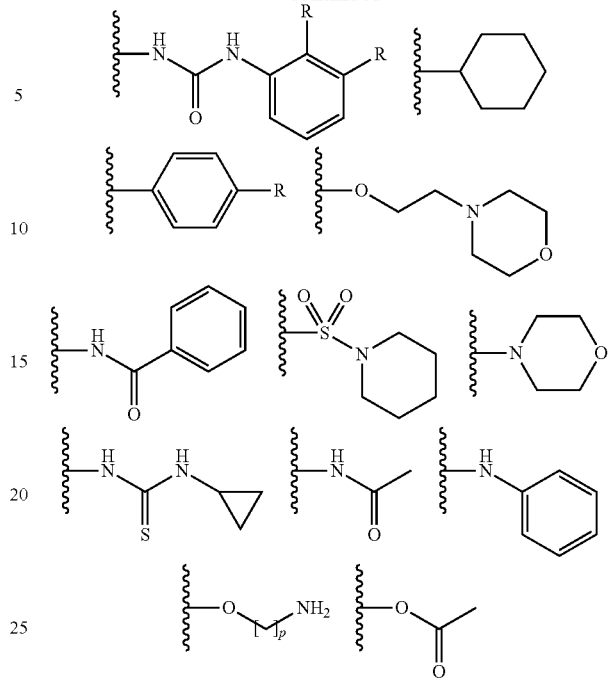

wherein $R_5$, $R_6$, $R_7$, $R_8$, $R_{11}$, $R_{14}$, $R_{15}$ and $R_{16}$; are as defined in claim 1 and R independently represents a hydrogen; substituted or unsubstituted, branched or unbranched $C_{1-6}$alkyl; an —OH; or a halogen and wherein m=0 or 1 and p=3 or 4.

6. A compound according, to claim 1, in the trans-isomer form:

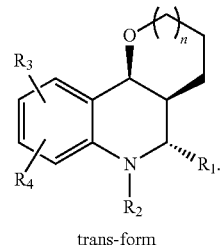

trans-form

7. A compound according to claim 1, in the cis-isomer form:

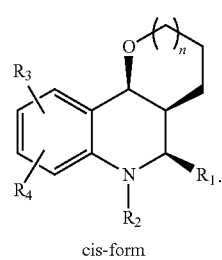

cis-form

8. A compound according to claim 1, selected from the group consisting of:

(4aSR*, 5RS*,10bSR*)-9-(3-chlorophenoxy)-5-cyclohexyl-3,4,4a,5,6,10b-hexahydro-2H-pyrano[3,2-c]quinoline hydrochloride;

(4aSR*,5SR*,10bSR*)-9-(3-chlorophenoxy)-5-cyclohexyl-3,4,4a,5,6,10b-hexahydro-2H-pyrano[3,2-c]quinoline hydrochloride;

1-(3-chloro-2-methylpheny)-3((4aSR*,5SR*, 10bSR*)-5-cyclohexyl-3,4,4a,5,6,10b-hexahydro-2H-pyrano[3,2-c]quinolin-9-yl)urea hydrochloride;

N-((4aSR*,5SR*,10bSR*)-5-cyclohexyl-3,4,4a,5,6,10b-hexahydro-2H-pyrano[3,2-c]quinolin-9-yl)pentanamide hydrochloride;

(4aSR*,5SR*,10bSR*)-5-cyclohexyl-N-cyclopropyl-3,4,4a,5,6,10b-hexahydro-2H-pyrano[3,2-c]quinoline-9-carboxamide hydrochloride;

(4aSR*,5RS*,10bSR*)-5-(1-benzylpiperidin-4-yl)-9-(isopentyloxy)-3,4,4a,5,6,10b-hexahydro-2H-pyrano[3,2-c]quinoline hydrochloride;

(4aSR*,5RS*,10bSR*)-5-cycohexyl-3,4,4a,5,6,10b-hexahydro-2H-pyrano[3,2-c]quinolin-10-amine;

(4aSR*,5SR*,10bSR*)-5-cyclohexyl-9-(trifluoromethoxy)-3,4,4a,5,6,10b-hexahydro-2H-pyrano[3,2-c]quinoline;

(4aSR*,5SR*,10bSR*)-5-cyclohexyl-8-ethyl-3,4,4a,5,6,10b-hexahydro-2H-pyrano[3,2-c]quinoline;

(4aSR*,5SR*,10bSR*)-ethyl 5-cyclohexyl-3,4,4a,5,6,10b-hexahydro-2H-pyrano[3,2-c]quinoline-9-carboxylate hydrochloride;

(4aSR*,5RS*,10bSR*)-5-cyclohexyl-3,4,4a,5,6,10b-hexahydro-2H-pyrano[3,2-c]quinolin-9ol;

(4aSR*,5RS*,10bSR*)-5-cyclohexyl-10-nitro-3,4,4a,5,6,10b-hexahydro-2H-pyrano[3,2-c]quinoline;

(4aSR*,5SR*,10bSR*)-9-tert-butyl-5-cyclohexyl-3,4,4a,5,6,10b-hexahydro-2H-pyrano[3,2-c]quinoline;

(4aSR*,5RS*,10bSR*)-5-cyclohexyl-9-methoxy-3,4,4a,5,6,10b-hexahydro-2H-pyrano[3,2-c]quinoline;

(4aSR*,5RS*,10bSR*)-9-butoxy-5-cyclohexyl-3,4,4a,5,6,10b-hexahydro-2H-pyrano[3,2-c]quinoline hydrochloride;

(4aSR*,5SR*,10bSR*)-9-butoxy-5-cyclohexyl 3,4,4a,5,6,10b-hexahydro-2H-pyrano[3,2-c]quinoline hydrochloride;

(4aSR*,5RS*,10bSR*)-5-cyclopentyl-9-(trifluoromethoxy)-3,4,4a,5,6,10b-hexahydro-2H-pyrano[3,2-c]quinoline hydrochloride;

(4aSR*,5RS*,10bSR*)-5-cyclohexyl-9-(trifluoromethylthio)-3,4,4a,5,6,10b-hexahydro-2H-pyrano[3,2-c]quinoline hydrochloride;

(4aSR*,5RS*,10bSR*)-5-cyclohexyl-9-methyl-3,4,4a,5,6,10b-hexahydro-2H-pyrano[3,2-c]quinoline hydrochloride;

(4aSR*,5RS*,10bSR*)-5-cyclohexyl-9-fluoro-3,4,4a,5,6,10b-hexahydro-2H-pyrano[3,2-c]quinoline hydrochloride;

(4aSR*,5RS*,10bSR*)-5-cyclohexyl-9-isopropyl-3,4,4a,5,6,10b-hexahydro-2H-pyrano[3,2-c]quinoline hydrochloride;

(4aSR*,5RS*,10bSR*)-5-cyclohexyl-7-(trifluoromethoxy)-3,4,4a,5,6,10b-hexahydro-2H-pyrano[3,2-c]quinoline hydrochloride;

(4aSR*,5RS*,10bSR*)-9-butyl-5-cyclohexyl-3,4,4a,5,6,10b-hexahydro-2H-pyrano[3,2-c]quinoline hydrochloride:

(4aSR*,5RS*,10bSR*)-5,9-dicyclohexyl-3,4,4a,5,6,10b-hexahydro-2H-pyrano[3,2-c]quinoline hydrochloride;

(4aSR*,5RS*,10bSR*)-5-cyclohexyl-9-phenoxy-3,4,4a,5,6,10b-hexahydro-2H-pyrano[3,2-c]quinoline hydrochloride;

(4aSR*,5RS*,10bSR*)-5-cyclohexyl-9-(isopentyloxy)-3,4,4a,5,6,10b-hexahydro-2H-pyrano[3,2-c]quinoline hydrochloride;

(4aSR*,5SR*,10bSR*)-5-cyclohexyl-9-(isopentyloxy)-3,4,4a,5,6,10b-hexahydro-2H-pyrano[3,2-c]quinoline hydrochloride;

(3aSR*,4RS*,9bSR*)-8-butoxy-4-cyclohexyl-2,3,3a,4,5,9b-hexahydrofuro[3,2-c]quinoline hydrochloride;

(4aSR*,5RS*,10bSR*)-5-cyclohexyl-9-propoxy-3,4,4a,5,6,10b-hexahydro-2H-pyrano[3,2-c]quinoline hydrochloride;

(3aSR*,4RS*,9bSR*)-4-cyclohexyl-8-propoxy-2,3,3a,4,5,9b-hexahydrofuro[3,2-c]quinoline hydrochloride;

(3aSR*,4RS*,9bSR*)-4-cyclohexyl-8-(isopentyloxy)-2,3,3a,4,5,9b-hexahydrofuro[3,2-c]quinoline hydrochloride;

(3aSR*,4RS*,9bSR*)-propyl 4-cyclohexyl-2,3,3a,4,5,9b-hexahydrofuro[3,2-c]quinoline-8-carboxylate hydrochloride;

(3aSR*,4SR*,9bSR*)-propyl 4-cyclohexyl-2,3,3a,4,5,9b-hexahydrofuro[3,2-c]quinoline-8-carboxylate hydrochloride;

(4aSR*,5RS*,10bSR*)-5-cyclohexyl-9-phenyl-3,4,4a,5,6,10b-hexahydro-2H-pyrano[3,2-c]quinoline hydrochloride;

(3aSR*,4RS*,9bSR*)-4-cyclohexyl-8-(trifluoromethoxy)-2,3,3a,4,5,9b-hexahydrofuro[3,2-c]quinoline hydrochloride;

N-((4aSR*,5RS*,10bSR*)-5-cyclohexyl-3,4,4a,5,6,10b-hexahydro-2H-pyrano[3,2-c]quinolin-9-yl)acetamide hydrochloride;

N-((3aSR*,4RS*,9bSR*)-4-cyclohexyl-2,3,3a,4,5,9b-hexahydrofuro[3,2-c]quinolin-8-yl)acetemide hydrochloride;

(4aSR*,5RS*,10bSR*)-propyl 5-cyclohexyl-3,4,4a,5,6,10b-hexahydro-2H-pyrano[3,2-c]quinoline-9-carboxylate hydrochloride;

(3aSR*,4RS*,9bSR*)-8-butoxy-4-cyclohexyl-6-fluoro-2,3,3a,4,5,9b-hexahydrofuro[3,2-c]quinoline hydrochloride;

(3aSR*,4RS*,9bSR*)-4-cyclohexyl-8-(2-morpholinoethoxy)-2,3,3a,4,5,9b-hexahydrofuro[3,2-c]quinoline hydrochloride;

(3aSR*,4RS*,9bSR*)-8-butoxy-4-cyclohexyl-7-fluoro-2,3,3a,4,5,9b-hexahydrofuro[3,2-c]quinoline hydrochloride;

(3aSR*,4RS*,9bSR*)-4-cyclohexyl-8-phenyl-2,3,3a,4,5,9b-hexahydrofuro[3,2-c]quinoline hydrochloride;

(4aSR*,4RS*,10bSR*)-9-butoxy-5-cyclohexyl-8-fluoro-3,4,4a,5,6,10b-hexahydro-2H-pyrano[3,2-c]quinoline hydrochloride;

(3aSR*,4RS*,9bSR*)-4-cyclohexyl-8-nitro-2,3,3a,4,5,9b-hexahydrofuro[3,2-c]quinoline hydrochloride;

(4aSR*,5RS*,10-bSR*)-5-cyclohexyl-9-iodo-3,4,4a,5,6,10b-hexahydro-2H-pyrano[3,2-c]quinoline hydrochloride;

(4aSR*,5RS*,10bSR*)-ethyl 5-cyclohexyl-3,4,4a,5,6,10b-hexahydro-2H-pyrano[3,2-c]quinoline-8-carboxylate hydrochloride;

(4aSR*,5RS*,10bSR*)-ethyl 5-cyclohexyl-3,4,4a,5,6,10b-hexahydro-2H-pyrano[3,2-c]quinoline-10-carboxylate hydrochloride;

(4aSR*,5RS*,10bSR*)-9-butoxy-5-(piperidin-4-yl)-3,4,4a,5,6,10b-hexahydro-2H-pyrano[3,2-c]quinoline;

N-((4aSR*,5RS*,10bSR*)-5-cyclohexyl-3,4,4a,5,6,10b-hexahydro-2H-pyrano[3,2-c]quinolin-9-yl)benzamide hydrochloride;

(3aSR*,4RS*,9bSR*)-4-cyclohexyl-8-phenoxy-2,3,3a,4, 5,9b-hexahydrofuro[3,2-c]quinoline hydrochloride;
(4aSR*,5RS*,10bSR*)-5-cyclohexyl-9-ethyl-3,4,4a,5,6, 10b-hexahydro-2H-pyrano[3,2-c]quinoline hydrochloride;
(4aSR*,5RS*,10bSR*)-9-phenoxy-5-(tetrahydro-2H-pyran-4-yl)-3,4,4a,5,6,10b-hexahydro-2H-pyrano[3,2-c]quinoline hydrochloride;
(4aSR*,5RS*,10bSR*)-methyl 5-cyclohexyl-3,4,4a,5,6, 10b-hexahydro-2H-pyran[3,2-c]quinoline-9-carboxylate hydrochloride;
(4aSR*,5RS*,10bSR*)-9-(4-chlorophenoxy)-5-cyclohexyl-3,4,4a,5,6,10b-hexahydro-2H-pyrano[3,2-c]quinoline hydrochloride;
(4aSR*,5RS*,10bSR*)-5-cyclopentyl-9-phenoxy-3,4,4a, 5,6,10b-hexahydro-2H-pyrano[3,2-c]quinoline hydrochloride;
(4aSR*,5RS*,10bSR*)-5-cyclohexyl-9-p-tolyl-3,4,4a,5, 6,10b-hexahydro-2H-pyrano[3,2-c]quinoline hydrochloride;
4-((4aSR*,5RS*,10bSR*)-5-cyclohexyl-3,4,4a,5,6,10b-hexahydro-2H-pyrano[3,2-c]quinolin-9-yl)phenol hydrochloride;
(4aSR*,5RS*,10bSR*)-5-cyclohexyl-9-pentyl-3,4,4a,5,6, 10b-hexahydro-2H-pyrano[3,2-c]quinoline;
(4aSR*,5RS*,10bSR*)-5-cyclohexyl-9-pentyl-3,4,4a,5,6, 10b-hexahydro-2H-pyrano[3,2-c]quinoline hydrochloride;
(4aSR*,5SR*,10bSR*)-5-cyclohexyl-9-pentyl-3,4,4a,5,6, 10b-hexahydro-2H-pyrano[3,2-c]quinoline hydrochloride;
(4aSR*,5RS*,10bSR*)-5-cyclohexyl-9-(piperidin-1-ylsulfonyl)-3,4,4a,5,6,10b-hexahydro-2H-pyrano[3,2-c]quinoline hydrochloride;
(4aSR*,5RS*,10bSR*)-9-pentyl-5-(tetrahydro-2H-pyran-4-yl)-3,4,4a,5,6,10b-hexahydro-2H-pyrano[3,2-c]quinoline hydrochloride;
(4aSR*,5RS*,10bSR*)-5-cyclohexyl-9-morpholino-3,4, 4a,5,6,10b-hexahydro-2H-pyrano[3,2-c]quinoline hydrochloride;
(4aSR*,5RS*,10bSR*)-5-adamantyl-9-phenoxy-3,4,4a,5, 6,10b-hexehydro-2H-pyrano[3,2-c]quinoline hydrochloride;
(4aSR*5RS*,10bSR*)-9-(2-chlorophenoxy)-5-cyclohexyl-3,4,4a,5,6,10b-hexahydro-2H-pyrano[3,2-c]quinoline hydrochloride;
(4aSR*,5RS*,10bSR*)-5-cyclohexyl-9-(2-morpholinoethoxy)-3,4,4a,5,6,10b-hexahydro-2H-pyrano[3,2-c]quinoline;
(4aSR*,5RS*,10bSR*)-propyl 5-adamantyl-3,4,4a,5,6, 10b-hexahydro-2H-pyrano[3,2-c]quinoline-9-carboxylate hydrochloride;
(4aSR*,5RS*,10bSR*)-methyl 5-cyclohexyl-7-methyl-3, 4,4a,5,6,10b-hexahydro-2H-pyrano[3,2-c]quinoline-8-carboxylate hydrochloride;
(4aSR*,5RS*,10bSR*)-ethyl 5-cyclohexyl-3,4,4a,5,6, 10b-hexahydro-2H-pyrano[3,2-c]quinoline-7-carboxylate hydrochloride;
(4aSR*,5RS*,10bSR*)-9-phenoxy-5-(tetrahydro-2H-thiopyran-4-yl)-3,4,4a,5,6,10b-hexahydro-2H-pyrano[3, 2-c]quinoline hydrochloride;
(4aSR*,5RS*,10bSR*)-methyl 5-cyclopentyl-7-methyl-3,4,4a,5,6,10b-hexahydro-2H-pyrano[3,2-c]quinoline-8-carboxylate hydrochloride;
(4aSR*,5RS*,10bSR*)-ethyl 5-cyclopentyl-3,4,4a,5,6, 10b-hexahydro-2H-pyrano[3,2-c]quinoline-8-carboxylate hydrochloride;
(4aSR*,5RS*,10bSR*)-ethyl 5-cyclopentyl-3,4,4a,5,6, 10b-hexahydro-2H-pyrano[3,2-c]quinoline-10-carboxylate hydrochloride;
(3aSR*,4RS*,9bSR*)-ethyl 4-cyclopentyl-2,3,3a,4,5,9b-hexahydrofuro[3,2-c]quinoine-7-carboxylate hydrochloride;
(3aSR*,4RS*,9bSR*)-ethyl 4-cyclopentyl-2,3,3a,4,5,9b-hexahydrofuro[3,2-c]quinoline-9-carboxylate hydrochloride;
1-((4aSR*,5RS*,10bSR*)-5-cyclohexyl-3,4,4a,5,6,10b-hexahydro-2H-pyrano[3,2-c]quinolin-9-yl)-3-cyclopropylthiourea hydrochloride;
(4aSR*,5RS*,10bSR*)-5-cyclopentyl-3,4,4a,5,6,10b-hexahydro-2H-pyrano[3,2-c]quinoline-9-carbonitrile hydrochloride;
(4aSR*,5RS*,10bSR*)-5-cyclopentyl-9-(piperidin-1-ylsulfonyl)-3,4,4a,5,6,10b-hexahydro-2H-pyrano[3,2-c]quinoline hydrochloride;
(3aSR*,4RS*,9bSR*)-4-cyclopentyl-8-(piperidin-1-ylsulfonyl)-2,3,3a,4,5,9b-hexahydrofuro[3,2-c]quinoline;
(4aSR*,5RS*,10bSR*)-5-cyclopentyl-N,N-dimethyl-3,4, 4a,5,6,10b-hexahydro-2H-pyrano[3,2-c]quinoline-9-sulfonamide hydrochloride;
(4aSR*5RS*,10bSR*)-5-cyclopentyl-N,N-diethyl-3,4, 4a,5,6,10b-hexahydro-2H-pyrano[3,2-c]quinoline-9-sulfonamide hydrochloride;
(3aSR*,4RS*,9bSR*)-4-cyclohexyl-2,3,3a,4,5,9b-hexahydrofuro[3,2-c]quinolin-8-ol hydrochloride;
(3aSR*,4RS*,9bSR*)-4-cyclohexyl-8-pentyl-2,3,3a,4,5, 9b-hexahydrofuro[3,2-c]quinoline hydrochloride;
(3aSR*,4RS*,9bSR*)-8-pentyl-4-(tetrahydro-2H-pyran-4-yl)-2,3,3a,4,5,9b-hexahydrofuro[3,2-c]quinoline hydrochloride;
(3aSR*,4RS*,9bSR*)-8-(4-chlorophenoxy)-4-cyclohexyl-2,3,3a,4,5,9b-hexahydrofuro[3,2-c]quinoline;
(3aSR*,4RS*,9bSR*)-8-(4-chlorophenoxy)-4-cyclohexyl-2,3,3a4,5,9b-hexahydrofuro[3,2-c]quinoline hydrochloride;
(3aSR*,4RS*,9bSR*)-8-(benzyloxy)-4-cyclohexyl-2,3, 3a,4,5,9b-hexahydrofuro[3,2-c]quinoline hydrochloride;
(4aSR*,5RS*,10bSR*)-5-cyclohexyl-N-propyl-3,4,4a,5, 6,10b-hexahydro-2H-pyrano[3,2-c]quinoline-9-sulfonamide;
(4aSR*,5RS*,10bSR*)-5-cyclohexyl-9-(4-fluorobenzyloxy)-3,4,4a,5,6,10b-hexahydro-2H-pyrano[3,2-c]quinoline hydrochloride;
(3aSR*,4RS*,9bSR*)-4-cyclohexyl-8-(4-fluorobenzyloxy)-2,3,3a,4,5,9b-hexahydrofuro[3,2-c]quinoline hydrochloride;
(3aSR*,4RS*,9bSR*)-4-cyclohexyl-8-(3,4-dichlorophenoxy)-2,3,3a,4,5,9b-hexahydrofuro[3,2-c]quinoline hydrochloride;
(4aSR*,5RS*,10bSR*)-5-cyclohexyl-9-(3,4-dichlorophenoxy)-3,4,4a,5,6,10b-hexahydro-2H-pyrano[3,2-c]quinoline hydrochloride;
(3aSR*,4RS*,9bSR*)-ethyl 4-cyclohexyl-2,3,3a,4,5,9b-hexahydrofuro[3,2-c]quinoline-8-carboxylate hydrochloride;
(3aSR*,4RS*,9bSR*)-8-pentyl-4-(tetrahydro-2H-thiopyran-4-yl)-2,3,3a,4,5,9b-hexahydrofuro[3,2-c]quinoline hydrochloride;
(3aSR*,4RS*,9bSR*)-8-(2-chlorophenoxy)-4-cyclohexyl-2,3,3a,4,5,9b-hexahydrofuro[3,2-c]quinoline hydrochloride;

(3aSR*,4RS*,9bSR*)-4-cyclohexyl-N-phenyl-2,3,3a,4,5,9b-hexahydrofuro[3,2-c]quinolin-8-amine hydrochloride;

(4aSR*,5RS*,10bSR*)-5-cyclohexyl-9-ethoxy-3,4,4a,5,6,10b-hexahydro-2H-pyrano[3,2-c]quinoline hydrochloride;

N-((3aSR*,4RS*,9bSR*)-4-cyclohexyl-2,3,3a,4,5,9b-hexahydrofuro[3,2-c]quinolin-8-yl)benzamide hydrochloride;

(4aSR*,5RS*,10bSR*)-9-(isopentyloxy)-5-(piperidin-4-yl)-3,4,4a,5,6,10b-hexahydro-2H-pyrano[3,2-c]quinoline hydrochloride;

(4aSR*,5RS*,10bSR*)-9-(isopentyloxy)-5-(tetrahydro-2H-pyran-4-yl)-3,4,4a,5,6,10b-hexahydro-2H-pyrano[3,2-c]quinoline hydrochloride;

(3aSR*,4RS*,9bSR*)-4-cyclohexyl-6-(isopentyloxy)-2,3,3a,4,5,9b-hexahydrofuro[3,2-c]quinoline;

(3aSR*,4RS*,9bSR*)-4-cyclohexyl-8-morpholino-2,3,3a,4,5,9b-hexahydrofuro[3,2-c]quinoline hydrochloride;

(4aSR*,5RS*,10bSR*)-9-methoxy-5-(piperidin-4-yl)-3,4,4a,5,6,10b-hexahydro-2H-pyrano[3,2-c]quinoline hydrochloride;

(4aSR*,5RS*,10bSR*)-5-cyclopentyl-9-(isopentyloxy)-3,4,4a,5,6,10b-hexahydro-2H-pyrano[3,2-c]quinoline hydrochloride;

3-((3aSR*,4RS*,9bSR*)-4-cyclohexyl-2,3,3a,4,5,9b-hexahydrofuro[3,2-c]quinolin-8-yloxy)propan-1-amine hydrochloride;

1-((4aSR*,5RS*,10bSR*)-5-cyclohexyl-3,4,4a,5,6,10b-hexahydro-2H-pyrano[3,2-c]quinolin-9-yl)-3-(2,3-dichlorophenyl)urea hydrochloride;

(4aSR*,5RS*,10bSR*)-9-methoxy-5-(1-phenethylpiperidin-4-yl)-3,4,4a5,6,10b-hexahydro-2H-pyrano[3,2-c]quinoline hydrochloride;

(4aSR*,5RS*,10bSR*)-5-(1-(4-chlorobenzyl)piperidin-4-yl)-9-methoxy-3,4,4a,5,6,10b-hexahydro-2H-pyrano[3,2-c]quinoline hydrochloride;

(4aSR*,5RS*,10bSR*)-5-(1-ethylpiperidin-4-yl)-9-(isopentyloxy)-3,4,4a5,6,10b-hexahydro-2H-pyrano[3,2-c]quinoline hydrochloride;

4-((4aSR*,5RS*,10bSR*)-5-cyclohexyl-3,4,4a,5,6,10b-hexahydro-2H-pyrano[3,2-c]quinolin-9-yloxy)butan-1-amine hydrochloride;

3((4aSR*,5RS*,10bSR*)-5-cyclohexyl-3,4,4a,5,6,10b-hexahydro-2H-pyrano[3,2-c]quinolin-9-yloxy)propan-1-amine hydrochloride;

(4aSR*,5RS*,10bSR*)-5-cyclohexyl-9-(methylthio)-3,4,4a,5,6,10b-hexahydro-2H-pyrano[3,2-c]quinoline hydrochloride;

(4aS,5R,10bS)-9-(isopentyloxy)-5-(tetrahydro-2H-pyran-4-yl)-3,4,4a,5,6,10b-hexahydro-2H-pyrano[3,2-c]quinoline hydrochloride;

(4SR*,5RS*,10bSR*)-5-cyclohexyl-9-(isopentyloxy)-6-methyl-3,4,4a,5,6,10b-hexahydro-2H-pyrano[3,2-c]quinoline.

9. A process for the preparation of a compound of general formula (Ia) and/or (Ib):

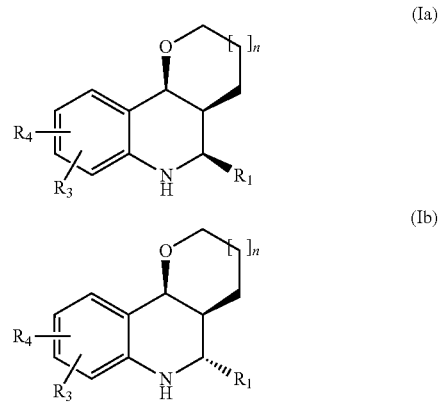

where $R_1$, $R_3$, $R_4$ and n have the same meaning as in claim 1, the process comprising the multicomponent reaction in an organic solvent and in the presence of a protic or Lewis acid between compounds of general formula (II), (III) and (IV):

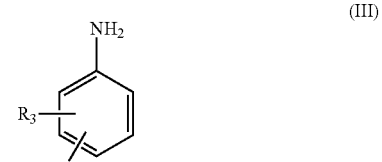

10. A pharmaceutical composition comprising a compound of claim 1 or a pharmaceutically acceptable salt thereof, and at least a pharmaceutically acceptable carrier, additive, adjuvant or vehicle.

* * * * *

UNITED STATES PATENT AND TRADEMARK OFFICE
CERTIFICATE OF CORRECTION

PATENT NO. : 9,193,738 B2
APPLICATION NO. : 14/374081
DATED : November 24, 2015
INVENTOR(S) : José-Luis Diaz-Fernández et al.

It is certified that error appears in the above-identified patent and that said Letters Patent is hereby corrected as shown below:

ON THE TITLE PAGE

Title Page, Foreign Patent Documents: "WO2005/063736" should be --WO2005/063735--.

Title Page, Other Publications, Extended European Search Report: "EP 12362020.1" should be --EP 12382020.1--.

IN THE CLAIMS

Column 67, Line 35: "represents e" should be --represents a--.

Column 67, Line 54: "$NR_5R_8$" should be --$NR_5R_6$--.

Column 89, Line 4: "-3((" should be -- -3-((--.

Signed and Sealed this
Twenty-sixth Day of January, 2016

Michelle K. Lee
*Director of the United States Patent and Trademark Office*